(12) United States Patent
Salituro et al.

(10) Patent No.: US 8,580,802 B2
(45) Date of Patent: Nov. 12, 2013

(54) PYRROLO[2,3-D]PYRIMIDINES AS INHIBITORS OF JANUS KINASES

(75) Inventors: Francesco Salituro, Marlboro, MA (US); Luc Farmer, Foxboro, MA (US); Tiansheng Wang, Concord, MA (US); Jian Wang, Newton, MA (US); Randy Bethiel, Lexington, MA (US); Marion Wannamaker, Stow, MA (US); Gabriel Martinez-Botella, Wayland, MA (US); John Duffy, Northborough, MA (US); Alexander Aronov, Watertown, MA (US); David Lauffer, Stow, MA (US); Albert Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 855 days.

(21) Appl. No.: 11/528,779

(22) Filed: Sep. 28, 2006

(65) Prior Publication Data

US 2007/0207995 A1     Sep. 6, 2007

Related U.S. Application Data

(60) Provisional application No. 60/722,561, filed on Sep. 30, 2005.

(51) Int. Cl.
| | | |
|---|---|---|
| *C07D 487/04* | (2006.01) | |
| *C07D 295/192* | (2006.01) | |
| *A61K 31/519* | (2006.01) | |
| *A61K 31/5377* | (2006.01) | |
| *A61K 31/496* | (2006.01) | |
| *A61P 25/28* | (2006.01) | |
| *A61P 35/00* | (2006.01) | |

(52) U.S. Cl.
USPC ... 514/265.1; 544/280; 544/122; 514/252.16; 514/234.2

(58) Field of Classification Search
USPC ...................... 544/280; 514/265.1
See application file for complete search history.

(56) References Cited

U.S. PATENT DOCUMENTS

2005/0137201 A1* 6/2005 Aronov et al. ............... 514/249
2005/0153989 A1* 7/2005 Grotzfeld et al. .......... 514/260.1

FOREIGN PATENT DOCUMENTS

| WO | 99/65908 A | 12/1999 |
| WO | 99/65909 A | 12/1999 |

OTHER PUBLICATIONS

Taylor et al.: "Synthesis of 4-Amino-5-cyanopyrrolo[2,3-d] pyrimidine, the Aglycone of Toyocamycin" J. Am. Chem. Soc., vol. 86, 1964, pp. 951-952, XP002412942, compound XIII.

* cited by examiner

*Primary Examiner* — Susanna Moore

(74) *Attorney, Agent, or Firm* — Lisa A. Dixon; Susan C. Kelly

(57) ABSTRACT

The present invention relates to compounds of the following structural formula:

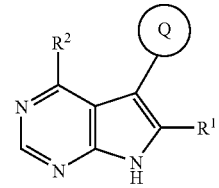

(I)

which are useful as inhibitors of protein kinases, particularly of JAK family kinases. The invention also provides pharmaceutically acceptable compositions comprising said compounds and methods of using the compositions in the treatment of various disease, conditions, or disorders.

26 Claims, 9 Drawing Sheets

US 8,580,802 B2

PYRROLO[2,3-D]PYRIMIDINES AS INHIBITORS OF JANUS KINASES

CROSS-REFERENCE TO RELATED APPLICATIONS

This application claims priority to U.S. Provisional Patent Application 60/722,561, filed Sep. 30, 2005, the entire contents of which are incorporated herein by reference.

TECHNICAL FIELD OF THE INVENTION

The present invention relates to compounds useful as inhibitors of Janus kinases (JAK). The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The downstream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease. Accordingly, it would be desirable to develop compounds that are useful as inhibitors of JAK family kinases.

SUMMARY OF THE INVENTION

It has been found that compounds of this invention, and pharmaceutically acceptable compositions thereof, are effective as inhibitors of protein kinases, particularly the JAK family kinases. These compounds have the general formula I:

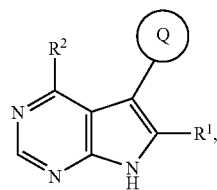

(I)

or a pharmaceutically acceptable salt thereof, wherein $R^1$, $R^2$ and Q are as defined below.

These compounds, and pharmaceutically acceptable compositions thereof, are useful for treating or lessening the severity of a variety of disorders, including proliferative disorders, cardiac disorders, neurodegenerative disorders, autoimmune disorders, conditions associated with organ transplantation, inflammatory disorders, or immunologically mediated disorders in a patient.

The compounds and compositions provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

Figure 1:
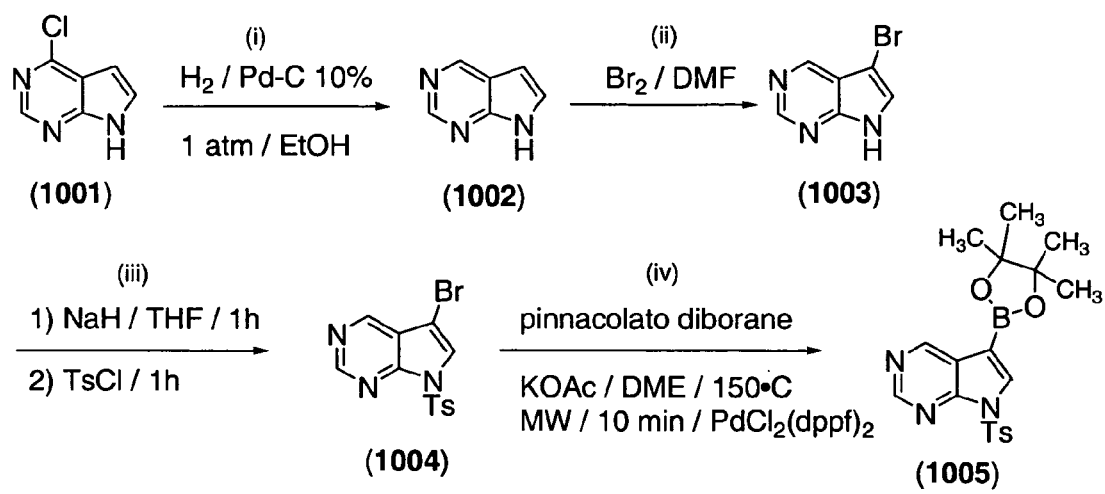
FIG. 1 is a scheme showing the synthesis of compound 1005 from compound 1001.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1120 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and In yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle", "heterocyclyl", "heterocycloaliphatic", or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Examples of heteroaryl rings include, but are not limited to, the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $J^Q$ $J^R$, $J^V$, $J^U$ and $J^X$ below. Other suitable substituents include: halogen; —R°;

—OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —OC(O)N(R°)$_2$; —OC(O)R°; —C(O)N(OR°) R°; —C(═NOR°) R°; —S(O)$_2$R°; —S(O)$_3$R°; —S(O)$_2$N(R°)$_2$; —S(O)R°; —NR°S(O)$_2$N(R°)$_2$; —NR°S(O)$_2$R°; —N(OR°)R°; —C(═NH)—N(R°)$_2$; or —(CH$_2$)$_{0-2}$NHC(O)R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, C(O)OH, C(O)O(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHC(O)O (alkyl), ═NNHS(O)$_2$ (alkyl), or ═NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, C(O)OH, C(O)O(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(═S)N(R$^+$)$_2$, —C(═NH)—N(R$^+$)$_2$, or —NR$^+$S(O)$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R+ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R+ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, C(O)OH, C(O)O(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

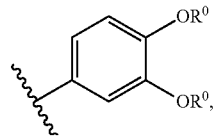

these two occurrences of R° are taken together with the oxygen atoms to which they are bound to form a fused 6-membered oxygen containing ring:

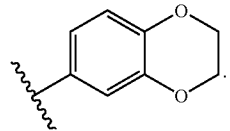 [SMILES: *c1ccc2c(c1)OCCO2]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —C(O)O—, —OC(O)—, —C(O)C(O)—, —C(O)—, —C(O)NR—, —C(═N—CN), —NRC(O)—, —NRC(O)O—, —S(O)$_2$NR—, —NRS(O)$_2$—, —NRC(O)NR—, —OC(O)NR—, —NRS(O)$_2$NR—, —S(O)—, or —S(O)$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

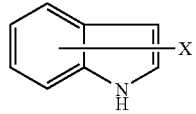

Figure a

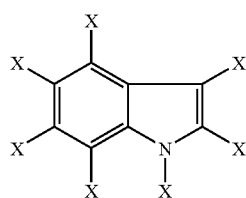

Figure b

This also applies to multiple ring systems fused to optional ring systems (which would be represented by dotted lines). For example, in Figure c, X is an optional substituent both for ring A and ring B.

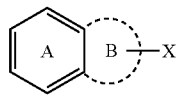

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

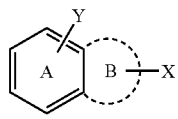

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

Description of Compounds of the Invention

The present invention features a compound of formula I:

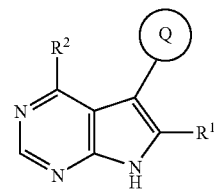

(I)

or a pharmaceutically acceptable salt thereof
wherein
R$^1$ is —(C$_{1-2}$ aliphatic)$_p$-R$^4$ wherein R$^1$ is optionally substituted with 1-3 occurrences of J;
R$^2$ is —(C$_{1-2}$ aliphatic)$_d$-R$^5$ wherein R$^2$ is optionally substituted with 1-3 occurrences of J;
R$^4$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NHC(=O)CH$_3$, or OH;
R$^5$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NHC(=O)CH$_3$, or OH;
J is halogen, OCH$_3$, OH, NO$_2$, NH$_2$, SCH$_3$, NCH$_3$, CN or unsubstituted C$_{1-2}$aliphatic, or two J groups, together with the carbon to which they are attached, form a cyclopropyl ring or C=O;
p and d are each independently 0 or 1;
Q is a 5-8 membered aromatic monocyclic ring having 0-3 heteroatoms selected from nitrogen, oxygen, or sulfur, or an 8-12 membered aromatic bicyclic ring having 0-6 heteroatoms selected from nitrogen, oxygen, or sulfur; wherein Q is optionally substituted with 1-10 occurrences of J$^Q$;
J$^Q$ is halogen, OCF$_3$, —(V$_m$)—R", —(V$_m$)—CN, —(V$_m$)—NO$_2$ or —(V$_m$)—(C$_{1-4}$ haloaliphatic), or two J$^Q$ groups, taken together with the atoms to which they are attached, form a 3-8 membered saturated, partially saturated, or unsaturated ring with 0-3 heteroatoms selected from O, N, or S, wherein said ring is optionally substituted with 0-4 occurrences of J$^U$;
V is a C$_{1-10}$ aliphatic, wherein up to three methylene units are replaced by G$^V$, wherein G$^V$ is selected from —NH—, —NR—, —O—, —S—, —C(O)O—, —OC(O)—, —C(O)C(O)—, —C(O)—, —C(O)NH—, —C(O)NR—, —C(=N—CN), —NHC(O)—, —NRC(O)—, —NHC(O)O—, —NRC(O)O—, —S(O)$_2$NH—, —S(O)$_2$NR—, —NHS(O)$_2$—, —NRS(O)$_2$—, —NHC(O)NH—, —NRC(O)NH—, —NHC(O)NR—, —NRC(O)NR, —OC(O)NH—, —OC(O)NR—, —NHS(O)$_2$NH—, —NRS(O)$_2$NH—, —NHS(O)$_2$NR—, —NRS(O)$_2$NR—, —S(O)—, or —S(O)$_2$—; and wherein V is optionally substituted with 1-6 occurrences of J$^V$;
R" is H or an optionally substituted group selected from C$_{1-6}$ aliphatic, C$_{3-10}$ cycloaliphatic, C$_{6-10}$ aryl, 5-10 membered heteroaryl, or 5-10 membered heterocyclyl; or two R" groups, or an R" group and an R group, on the same substituent or different substituents, together with the atom(s) to which they are attached, form an optionally substituted 3-8 membered heterocyclyl; wherein each optionally substituted R" group is independently and optionally substituted with 1-6 occurrences of $J^R$;

R is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of $J^X$;

each $J^V$, $J^U$, $J^X$, and $J^R$ are each independently selected from halogen, L, -(L$_n$)-R', -(L$_n$)-N(R')$_2$, -(L$_n$)-SR', -(L$_n$)-OR', -(L$_n$)-(C$_{3-10}$ cycloaliphatic), -(L$_n$)-(C$_{6-10}$ aryl), -(L$_n$)-(5-membered heteroaryl), -(L$_n$)-(5-10 membered heterocyclyl), oxo, $C_{1-4}$haloalkoxy, $C_{1-4}$haloalkyl, -(L$_n$)-NO$_2$, -(L$_n$)-CN, -(L$_n$)-OH, -(L$_n$)-CF$_3$, —C(O)OR', —C(O)OH, —C(O)R', —C(O)H, —OC(O)R', or —NC(O)R'; or any two $J^V$, $J^U$, $J^X$, or $J^R$ groups, on the same substituent or different substituents, together with the atom(s) to which each $J^V$, $J^U$, $J^X$, and $J^R$ group is bound, form a 5-7 membered saturated, unsaturated, or partially saturated ring;

R' is H or $C_{1-6}$ aliphatic; or two R' groups, or an R' group and an R group, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —NO$_2$, —CF$_3$, —CN, —C(O)OR*, —C(O)R*, OC(O)R*, or NHC(O)R*, wherein R* is H or an unsubstituted $C_{1-6}$ aliphatic;

L is a $C_{1-6}$ aliphatic wherein up to three methylene units are replaced by —NH—, —NR$^6$—, —O—, —S—, —C(O)O—, —OC(O)—, —C(O)C(O)—, —C(O)—, —C(O)NH—, —C(O)NR$^6$—, —C(=N—CN), —NHC(O)—, —NR$^6$C(O)—, —NHC(O)O—, —NR$^6$C(O)O—, —S(O)$_2$NH—, —S(O)$_2$NR$^6$—, —NHS(O)$_2$—, —NR$^6$S(O)$_2$—, —NHC(O)NH—, —NR$^6$C(O)NH—, —NHC(O)NR$^6$—, —NR$^6$C(O)NR$^6$, —OC(O)NH—, —OC(O)NR$^6$—, —NHS(O)$_2$NH—, —NR$^6$S(O)$_2$NH—, —NHS(O)$_2$NR$^6$—, —NR$^6$S(O)$_2$NR$^6$—, —S(O)—, or —S(O)$_2$—;

R$^6$ is selected from $C_{1-6}$ aliphatic, $C_{3-10}$ cycloaliphatic, $C_{6-10}$ aryl, 5-10 membered heteroaryl, or 5-10 membered heterocyclyl; or two R$^6$ groups, on the same substituent or different substituents, together with the atom(s) to which each R$^6$ group is bound, form a 3-8 membered heterocyclyl;

each of m and n is, independently, 0 or 1; provided that when R$^2$ is C$_1$, NH$_2$, or NCH$_3$, then Q is not optionally substituted phenyl; and when R$^1$ and R$^2$ are H, then Q is not

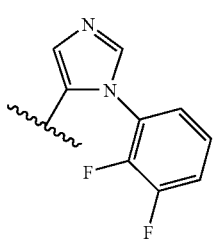
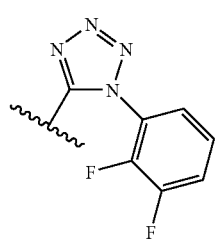

-continued

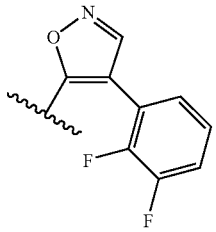
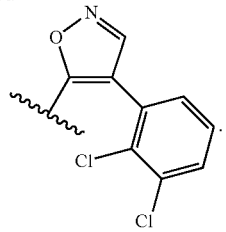

In one embodiment, when R$^1$ is C(=O)Et, then Q is not 4-OMe phenyl.

In another embodiment, Q is a 5-10 membered heteroaryl ring optionally substituted with 1-5 $J^Q$ groups. In a further embodiment, Q is a 5-6 membered heteroaryl ring optionally substituted with 1-3 $J^Q$ groups. In yet a further embodiment, Q is a 6-membered heteroaryl ring selected from pyridyl, pyrimidyl, pyrazinyl, triazinyl or pyridazinyl optionally substituted with 1-3 $J^Q$ groups.

In another embodiment, the invention features a compound having formula II-a:

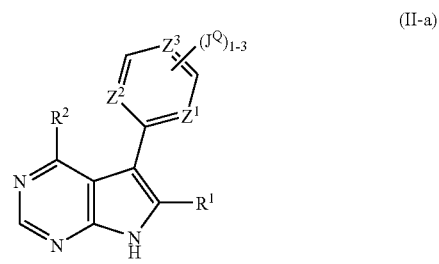

(II-a)

wherein each of R$^1$, R$^2$, and $J^Q$ is as defined for formula I; each of Z$^1$ and Z$^2$ is, independently, CH or N, wherein at least one of Z$^1$ or Z$^2$ is N; and Z$^3$ is C-$J^Q$ or N. In one embodiment, each of Z$^1$ and Z$^2$ is N. In a further embodiment, each of Z$^1$ and Z$^2$ is N and Z$^3$ is C-$J^Q$. In another embodiment, each of Z$^1$, Z$^2$, and Z$^3$ is N. In another embodiment, Z$^1$ is N, and each of Z$^2$ and Z$^3$ is CH. In yet another embodiment, each of Z$^1$ and Z$^3$ is N and Z$^2$ is CH.

The present invention also provides a compound of formula I or formula II-a wherein $J^Q$ is halo, —NO$_2$, —CN, —R", —V—R", —V—CN or —V—NO$_2$. In another embodiment, at least one $J^Q$ is —V—R". In a further embodiment, V is $C_{1-6}$alkyl, wherein two methylene units are replaced by G$^V$ and each G$^V$ is, individually, selected from —NH—, —NR—, —O—, —S—, —C(O)O—, —OC(O)—, —C(O)—, —C(O)NH—, —C(O)NR—, —NHC(O)— or —NRC(O)—. In a further embodiment, one G$^V$ is directly bonded to R". In yet another embodiment, one G$^V$ is directly bonded to Q.

In another embodiment of the invention, V is substituted with up to two $J^V$ groups, wherein each $J^V$ is, individually $C_{1-3}$alkyl or two $J^V$ groups, together with the carbon to which they are attached, form a 3-6 membered cycloalkyl ring. In a further embodiment, $J^V$ is selected from halogen, NH$_2$, NO$_2$, CN, OH, $C_{1-3}$alkyl, $C_{1-3}$haloalkyl, $C_{1-3}$haloalkoxy, —(C$_{1-3}$ alkyl)-O—(C$_{1-3}$alkyl), —(C$_{1-6}$alkyl)-OH, —O—(C$_{1-6}$alkyl), —NH—(C$_{1-6}$alkyl), —N(C$_{1-6}$alkyl)$_2$, —C(=O)O(C$_{1-6}$ alkyl), —C(=O)OH, —C(=O)(C$_{1-6}$alkyl), —C(=O)H, —OC(=O)(C$_{1-6}$alkyl), —NC(=O)(C$_{1-6}$-alkyl), $C_{1-6}$alkyl-CN, or oxo. In yet a further embodiment, $J^V$ is selected from C₁₋₆alkyl, CF₃, —(C₁₋₃alkyl)CF₃, —O—(C₁₋₆ alkyl), —CH₂O—(C₁₋₃alkyl), —C(=O)(C₁₋₆alkyl), —C(=O)OH, or —C(=O)O(C₁₋₆alkyl).

The present invention also provides a compound of formula I or formula II-a wherein each occurrence of $J^Q$ is independently selected from R", —CH₂R", halogen, CN, NO₂, —C(O)R", —C(O)R⁹R", —N(R')R", —CH₂N(R')R", —OR", —CH₂OR", —SR", —CH₂SR", —C(O)OR", —NR'C(O)R", —NR'C(O)R⁹R", —NR'C(O)OR", —NR'C(O)OR⁹R", —C(O)N(R')R", —C(O)N(R')R⁹R", —C(O)NHR⁹OR", —C(O)N(R')R⁹OR", —S(O)₂N(R')R", —S(O)₂N(R')R⁹R", —C(O)N(R')R⁹N(R')R", —OR⁹OR", —OR⁹N(R')R", —NR"C(R')(R⁸)R", —NR'C(R')(R⁸)C(O)OR", —N(R')R⁹R", —N(R')R⁹R", —N(R')R⁹N(R')R", —N(R') R⁹OR", —NR'C(R')(R⁸)R", —NR'CH₂C(O)N(R')R", or —NR'C(R')(R⁸)C(O)N(R')R", wherein a) R⁸ is H, C₁₋₆ alkyl, CF₃, CH₂CF₃, CH₂CN, or CH₂OR'; or R⁸ and R', taken together with the atom(s) to which they are attached, form a 3-8 membered ring having 0-3 heteroatoms selected from O, N, or S optionally substituted with 0-4 occurrences of $J^V$, or b) R⁹ is C₁₋₆aliphatic; wherein each R⁸ and R⁹ are independently and optionally substituted with 1-4 occurrences of $J^V$; or two $J^Q$ groups, taken together with the atoms to which they are attached, form a 3-8 membered saturated, partially saturated or unsaturated ring with 0-3 heteroatoms selected from O, N, or S optionally substituted with 0-4 occurrences of $J^V$.

In a further embodiment of $J^Q$, R" is selected from hydrogen, a C₁-C₆aliphatic group, optionally substituted with up to six occurrences of R⁷, or R" is a ring selected from:

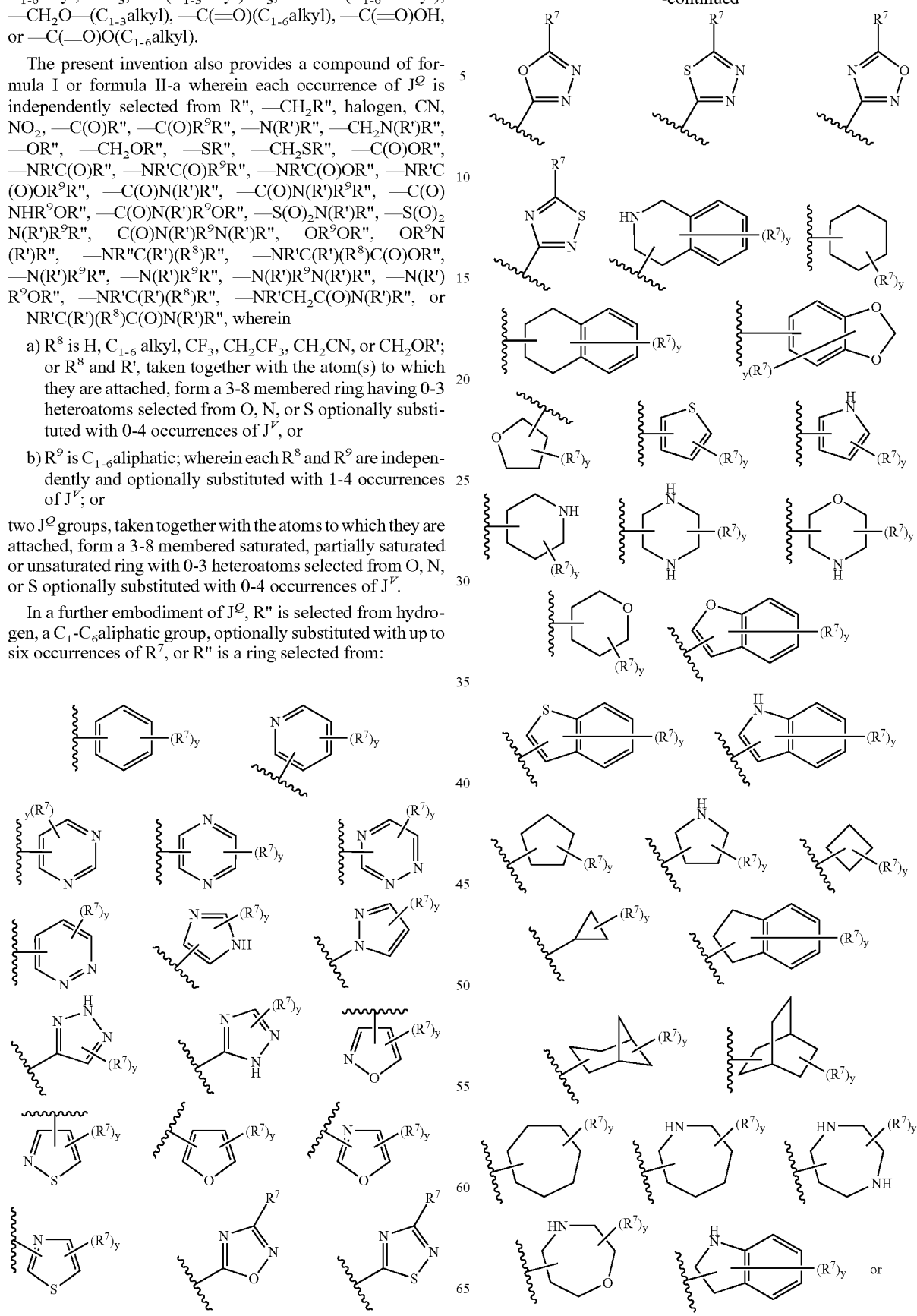

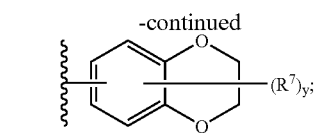

or two occurrences of R', or R' and R", taken together with the nitrogen atom to which they are bound, form an optionally substituted 3-10-membered monocyclic or bicyclic heterocyclic ring selected from:

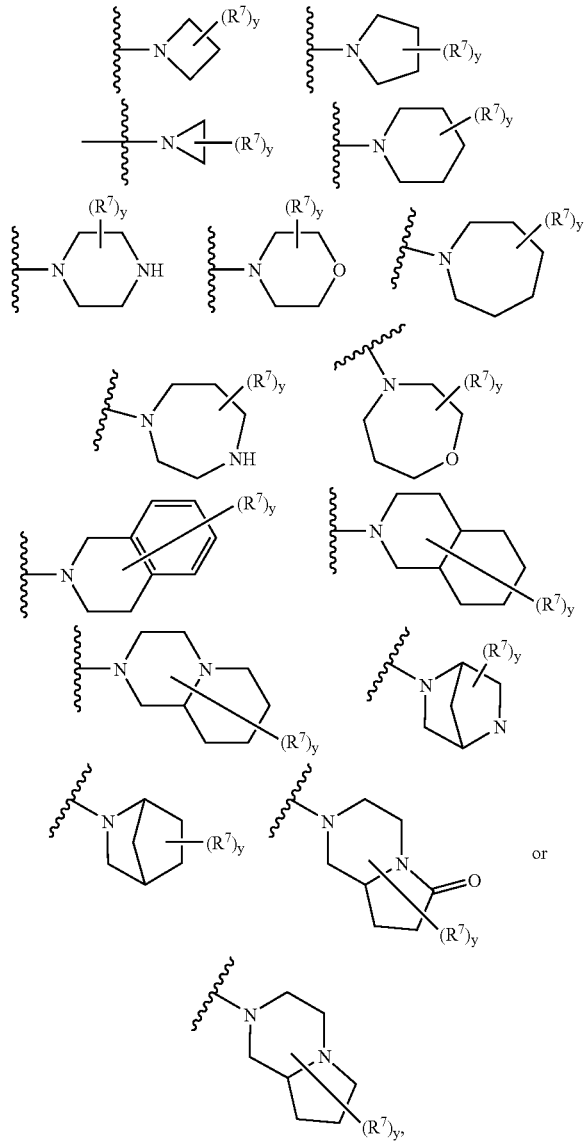

wherein y is 0, 1, 2, or 3, and each occurrence of $R^7$ is independently R', —$CH_2R'$, halogen, —$CH_2CH$, —CN, —$NO_2$, —$N(R')_2$, —$CH_2N(R')_2$, —OR', —$CH_2OR'$, —SR', —$CH_2SR'$, —C(O)OR', —C(O)R', —$NR^9C(O)R'$, —$NR^9C(O)OR'$, —$C(O)N(R')_2$, —$S(O)_2N(R')_2$, —$NR^9S(O)_2R'$, —$C(O)NR^9(CH_2)_2N(R^9)R'$, —$C(O)NR^9(CH_2)_3N(R^9)R'$, —$C(O)NR^9(CH_2)_4N(R^9)R'$, —$O(CH_2)_2OR'$, —$O(CH_2)_3OR'$, —$O(CH_2)_4OR'$, —$O(CH_2)_2N(R^9)R'$, —$O(CH_2)_3N(R^9)R'$, —$O(CH_2)_4N(R^9)R'$, —$NR^9CH(CH_2OH)R'$, —$NR^9CH(CH_2CH_2OH)R'$, —$NR^9(CH_2)R'$, —$NR^9(CH_2)_2R'$, —$NR^9(CH_2)_3R'$, —$NR^9(CH_2)_4R'$, —$NR^9(CH_2)N(R^9)R'$, —$NR^9(CH_2)_2N(R^9)R'$, —$NR^9(CH_2)_3N(R^9)R'$, —$NR^9(CH_2)_4N(R^9)R'$, —$NR^9(CH_2)OR'$, —$NR^9(CH_2)_2OR'$, —$NR^9(CH_2)_3OR'$, or —$NR^9(CH_2)_4OR'$; wherein $R^9$ is H or $R^6$.

In another embodiment of the invention, $J^Q$ is selected from —N(R')R", —NR'C(O)R', —NR'C(O)$R^9$R", —NR'C(O)OR", —NR'C(O)OR$^9$R", —NR'CH($R^8$)R", —NR'CH($R^8$)C(O)OR", —N(R')$R^9$R", —N(R')$R^9$R", —N(R')$R^9$N(R')R", —N(R')$R^9$OR", —NR'CH($R^8$)R", —NR'$CH_2$C(O)N(R')R", or —NR'CH($R^8$)C(O)N(R')R".

The present invention also features a compound having formula II-b:

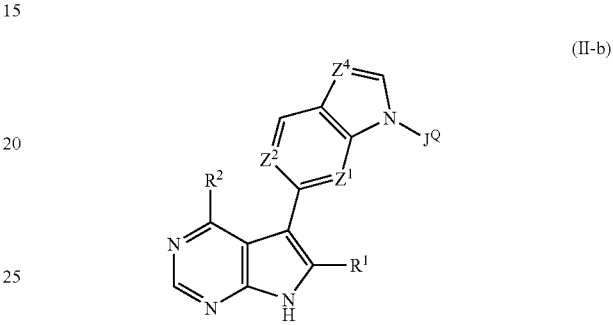

wherein each of $Z^1$, $Z^2$, and $Z^4$ is, independently, CH or N, and wherein at least one of $Z^1$ or $Z^2$ is N.

In one embodiment, each of $Z^1$ and $Z^2$ is N.

In one embodiment, $J^Q$ is

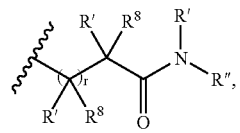

wherein $R^8$ is optionally substituted with up to two occurrences of $J^V$.

In one embodiment, r is 0 and $R^1$, $R^8$, and the intervening carbon together are:

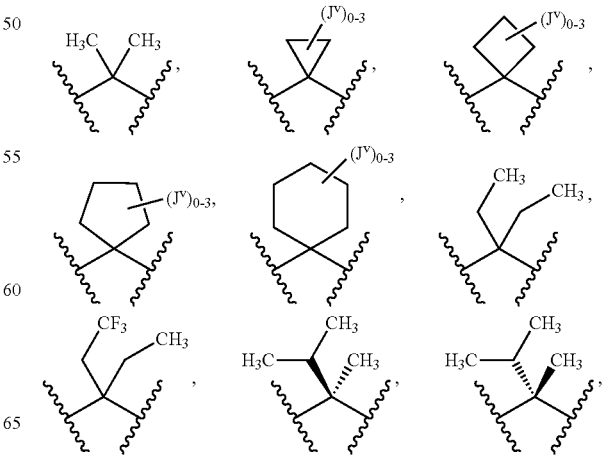

-continued

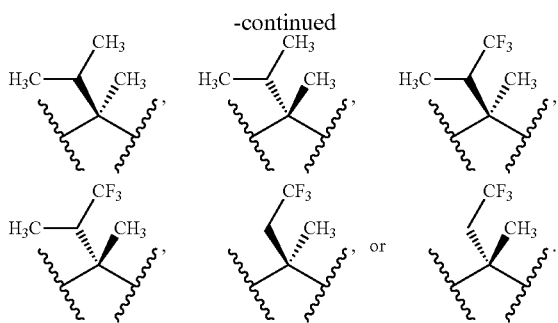

In yet another embodiment, $J^Q$ is

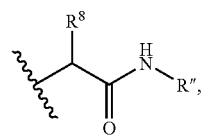

wherein
$R^8$ is optionally substituted with up to two occurrences of $J^V$.

The present invention also provides a compound of formula I, formula II-a, or formula II-b, wherein p is 0. In one embodiment, $R^1$ is H, halogen, CN, $NO_2$, $CF_3$, $CH_3$, $OCH_3$, or OH. In another embodiment, $R^1$ is H, halogen, or $CF_3$. In yet another embodiment, $R^1$ is H.

The present invention also provides a compound of formula I, formula II-a, or formula II-b, wherein d is 0. In one embodiment, $R^2$ is H, halogen, CN, $NO_2$, $CF_3$, $CH_3$, $OCH_3$, or OH. In another embodiment, $R^2$ is H, halogen, or $CF_3$. In yet another embodiment, $R^2$ is H.

The present invention also provides a compound of formula I, formula II-a, or formula II-b, wherein $R^1$ and $R^2$ are H.

The present invention also features a compound having formula III:

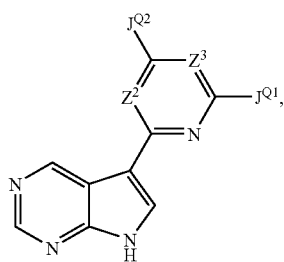

(III)

wherein
$Z^2$ is CH or N;
$Z^3$ is C-$J^{Q3}$ or N;
$J^{Q1}$ is —N(R')R", —CH$_2$N(R')R", —NR'C(O)R', —NR'C(O)R$^9$R", —NR'C(O)OR", —NR'C(O)OR$^9$R", —NR'C(R')(R$^8$)R", —NR'C(R')(R$^8$)C(O)OR", —N(R')R$^9$R", —N(R')R$^9$R", —N(R')R$^9$N(R')R", —N(R')R$^9$OR", —NR'C(R')(R$^8$)R", —NR'CH$_2$C(O)N(R')R", or —NR'CR'(R$^8$)C(O)N(R')R";
$J^{Q2}$ is hydrogen, —C(O)OH, —C(O)OR", —C(O)OR$^9$R", —C(O)R", —C(O)R$^9$R", —C(O)NHR", —C(O)N(R)R", —C(O)NHR$^9$OR", —C(O)NHR$^9$R", —C(O)N(R)R$^9$R", —OH, —OR", —CN, or —R";

wherein
a) $R^8$ is H, $C_1$—alkyl, $CF_3$, $CH_2CF_3$, $CH_2CN$, or $CH_2OR'$; or $R^8$ and R', taken together with the atom(s) to which they are attached, form a 3-8 membered ring having 0-3 heteroatoms selected from O, N, or S, wherein $R^8$ or said ring is optionally substituted with 0-4 occurrences of $J^V$;
b) $R^9$ is $C_{1-6}$aliphatic; or $R^9$ and R or R', taken together with the atom(s) to which they are attached, form a 3-8 membered ring having 0-3 heteroatoms selected from O, N, or S, wherein $R^9$ or said ring is optionally substituted with 0-4 occurrences of $J^V$; and
$J^{Q3}$ is hydrogen, halo, or $NO_2$.

In one embodiment of compounds having formula III, $Z^2$ is CH. In another embodiment, $Z^2$ is N. In a further embodiment, $Z^3$ is C-$J^{Q3}$ and $J^{Q3}$ is hydrogen. In yet a further embodiment, $Z^3$ is C-$J^{Q3}$ and $J^{Q3}$ is F. In another embodiment, $Z^3$ is N. In yet another embodiment, both $Z^2$ and $Z^3$ are N.

In another embodiment, $J^{Q2}$ is hydrogen. In another embodiment, $J^{Q2}$ is —C(O)OH, —C(O)OR", —C(O)R", —C(O)NHR", —C(O)N(R)R", —C(O)N(R)R$^9$R", —CN, or —R", wherein $J^{Q2}$ is optionally substituted with up to two occurrences of $J^V$.

In another embodiment $J^{Q1}$ is:

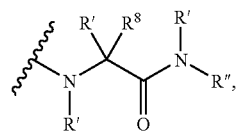

wherein
$R^8$ is optionally substituted with up to two occurrences of $J^V$.
In a further embodiment, $J^{Q1}$ is:

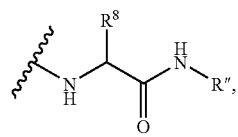

wherein
$R^8$ is optionally substituted with up to two occurrences of $J^V$.
In a further embodiment of compounds having formula III, $J^{Q1}$ is as defined directly above and $J^{Q2}$ is hydrogen.

In another embodiment of compounds having formula III, $J^{Q1}$ is

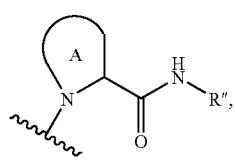

wherein
Ring A is optionally substituted with up to two occurrences of $J^V$. In a further embodiment, Ring A is selected from:

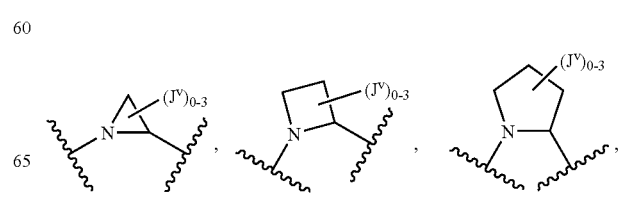

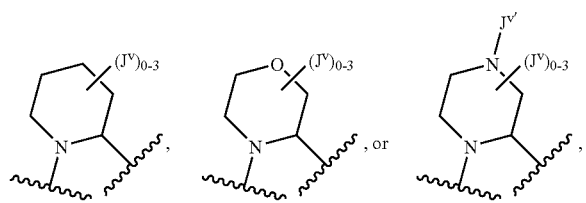

wherein $J^{V'}$ is H or $J^V$. In yet a further embodiment of a compound of formula III, $J^{Q1}$ is as defined directly above and $J^{Q2}$ is hydrogen.

In another embodiment of compounds having formula III, $J^{Q1}$ is

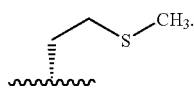

In a further embodiment of compounds having formulae II-a, II-b, or III, $R^8$ is selected from

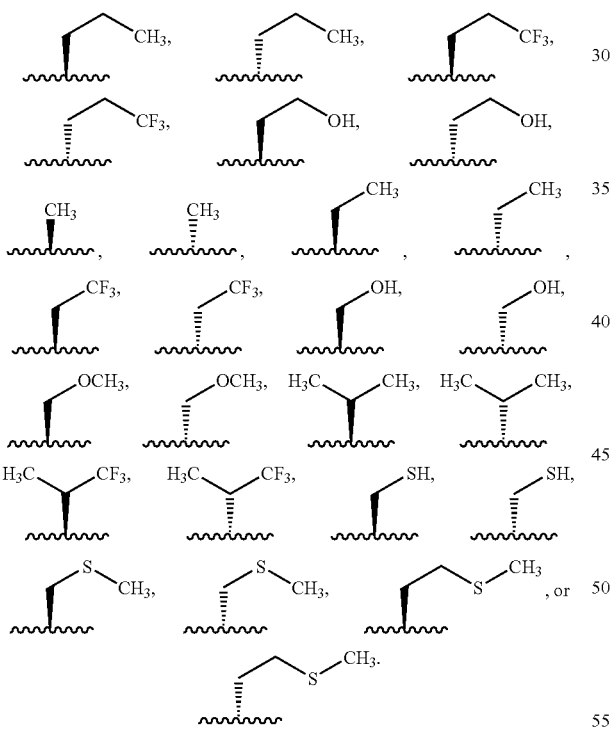

In a further embodiment of compounds having formulae II-a, II-b or III, R', $R^8$, and the intervening carbon are:

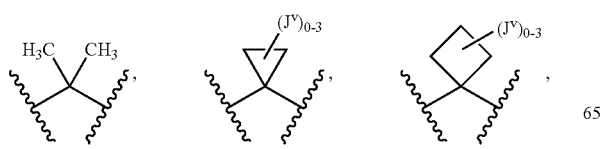

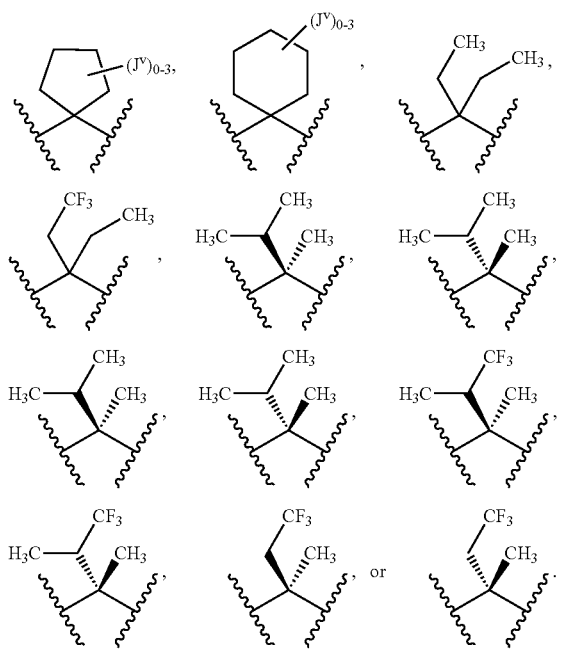

In another embodiment of compounds having formulae II-a, II-b or III, R" is $CH_3$, $CH_2CH_3$ or $CH_2CH_2CH_3$, $CF_3$, $CH_2CF_3$, or $CH_2CH_2CF_3$.

In another aspect, the invention features a compound selected from the group of compounds listed in Table 1.

TABLE 1

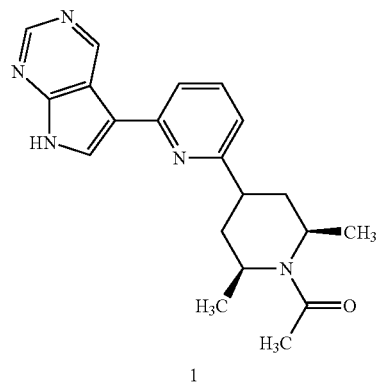 [SMILES: CC(=O)N1[C@H](C)CC(c2cccc(-c3c[nH]c4ncncc34)n2)C[C@@H]1C]

1

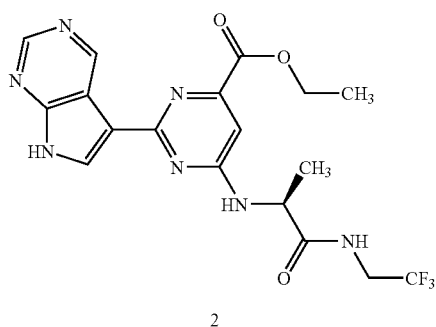 [SMILES: CCOC(=O)c1cc(N[C@@H](C)C(=O)NCC(F)(F)F)nc(-c2c[nH]c3ncncc23)n1]

2

TABLE 1-continued
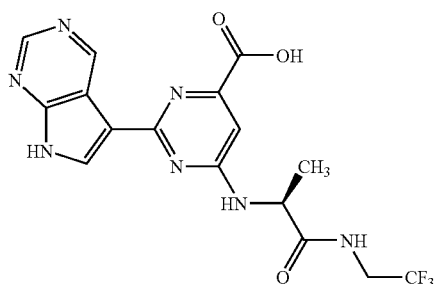
3
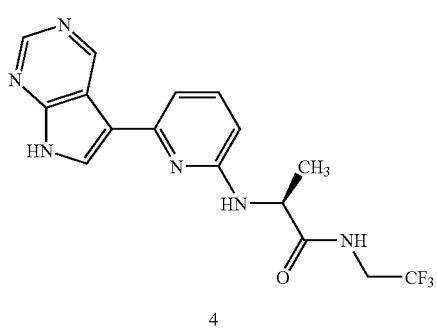 [SMILES: C[C@H](Nc1cccc(-c2c[nH]c3ncncc23)n1)C(=O)NCC(F)(F)F]
4
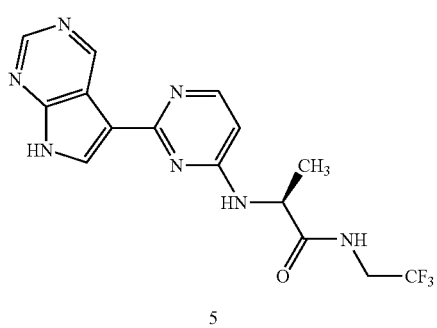 [SMILES: C[C@H](Nc1ccnc(-c2c[nH]c3ncncc23)n1)C(=O)NCC(F)(F)F]
5
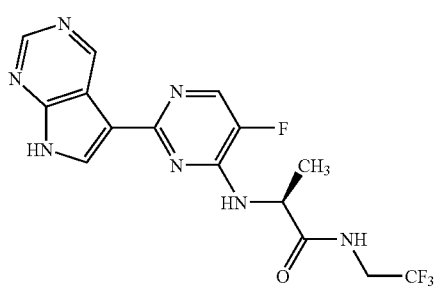
6
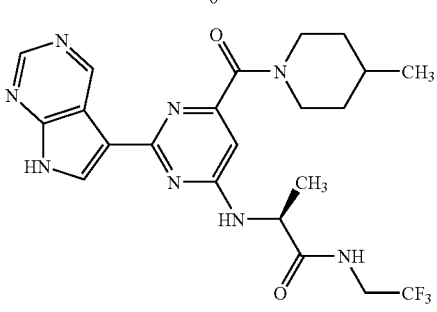
7
TABLE 1-continued
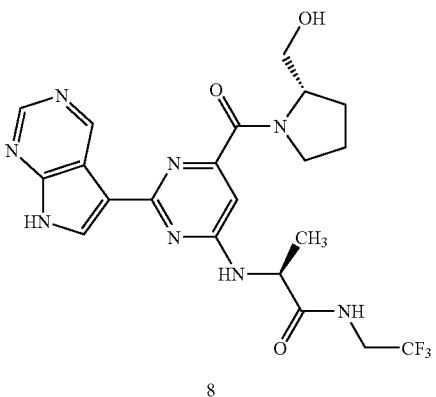 [SMILES: C[C@H](Nc1cc(C(=O)N2CCC[C@H]2CO)nc(-c2c[nH]c3ncncc23)n1)C(=O)NCC(F)(F)F]
8
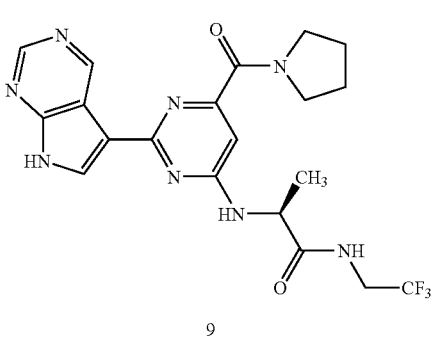 [SMILES: C[C@H](Nc1cc(C(=O)N2CCCC2)nc(-c2c[nH]c3ncncc23)n1)C(=O)NCC(F)(F)F]
9
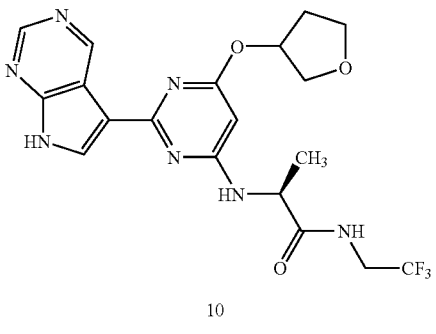 [SMILES: C[C@H](Nc1cc(OC2CCOC2)nc(-c2c[nH]c3ncncc23)n1)C(=O)NCC(F)(F)F]
10
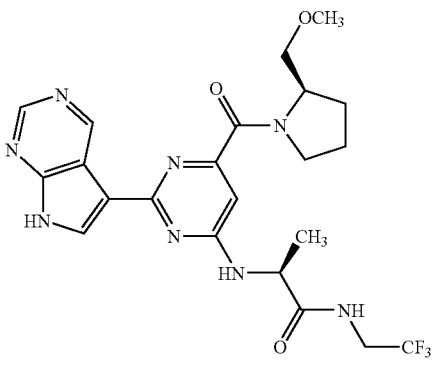
11

TABLE 1-continued
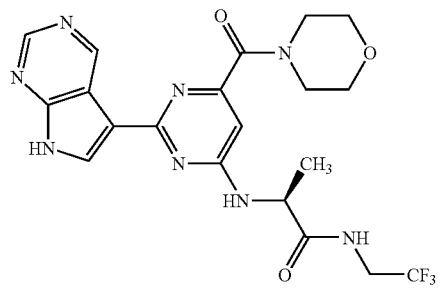
12
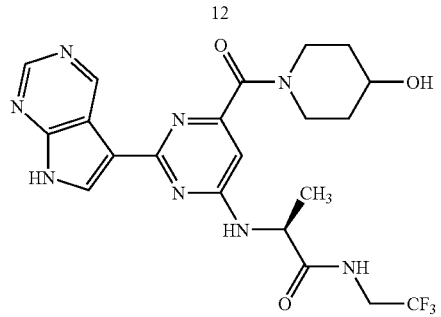
13
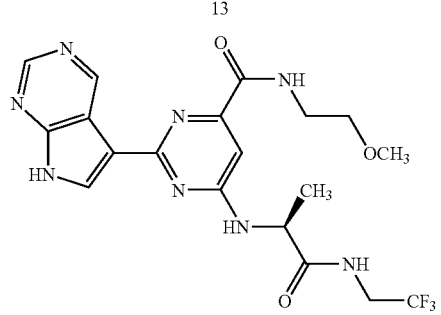
14
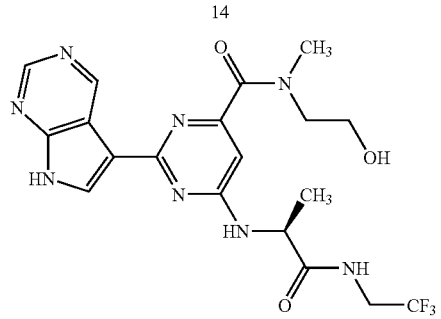
15
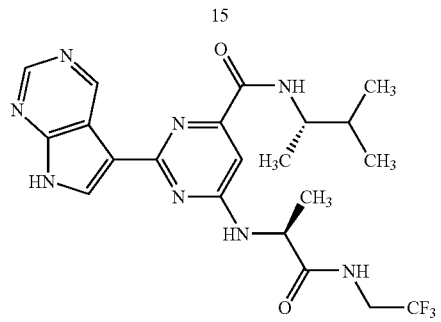
16
TABLE 1-continued
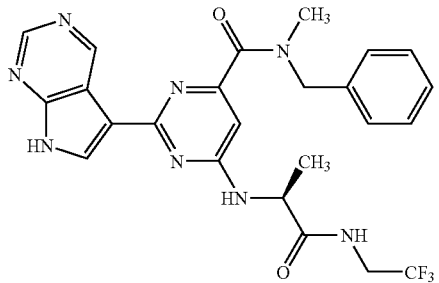
17
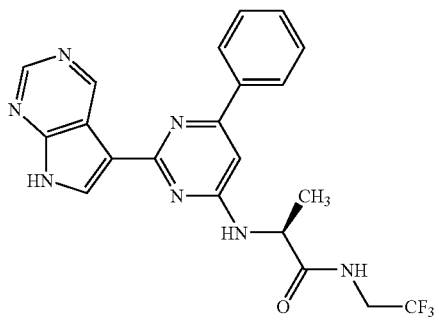
18
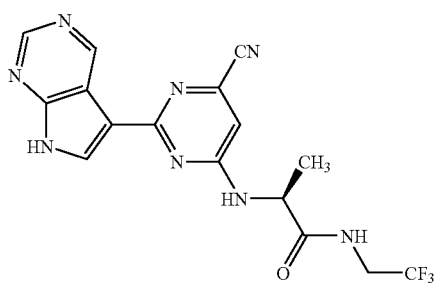
19
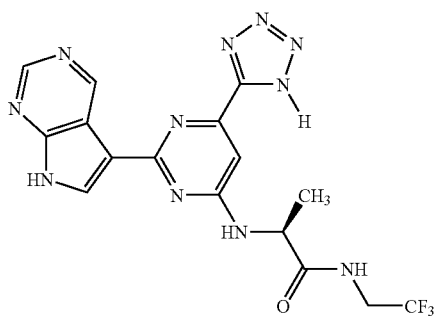
20

TABLE 1-continued
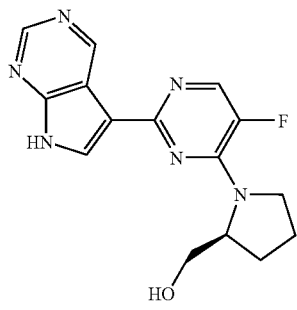
21
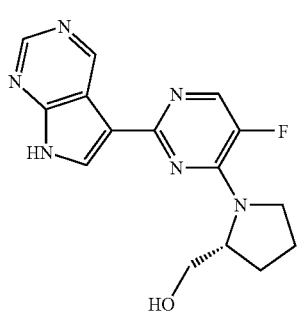
22
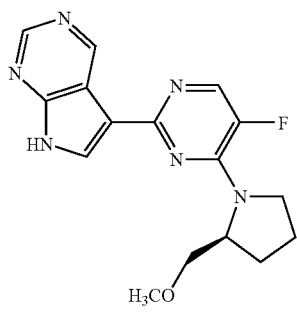
23
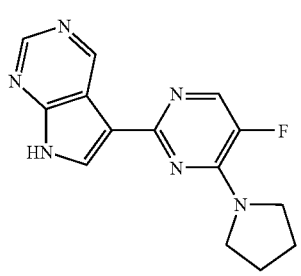
24
TABLE 1-continued
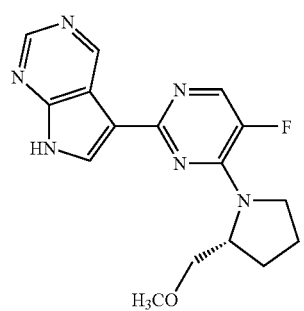
25
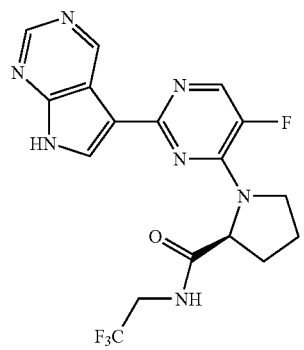
26
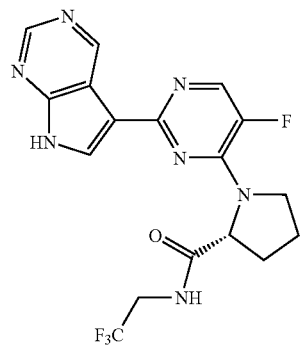
27
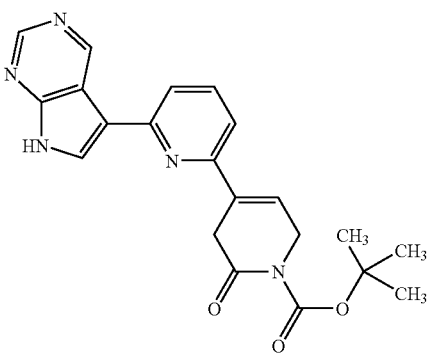
28

TABLE 1-continued
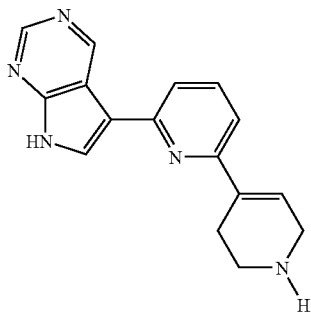
29
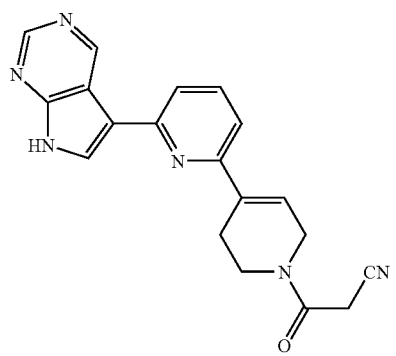
30
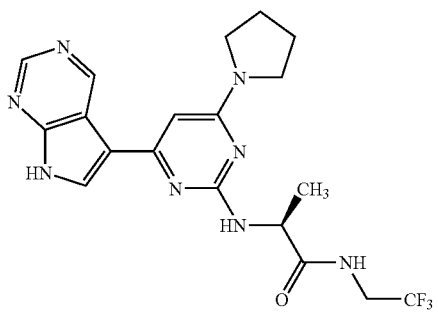
31
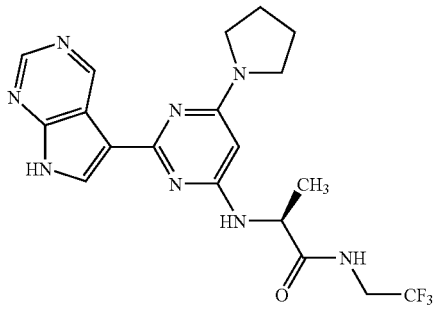
32
TABLE 1-continued
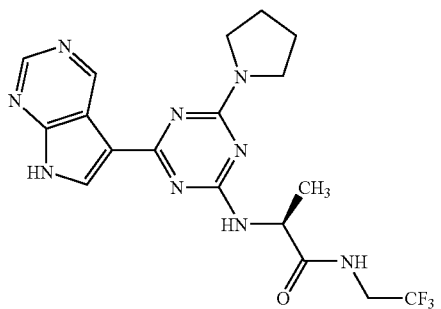
33
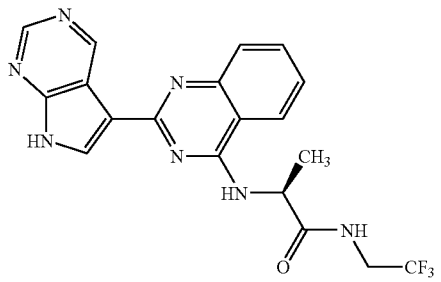
34
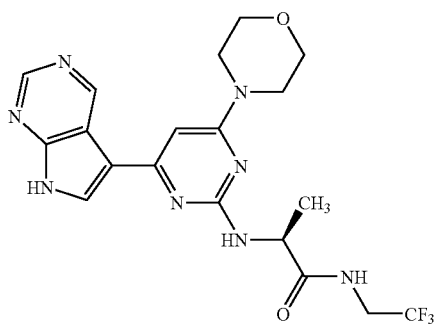
35
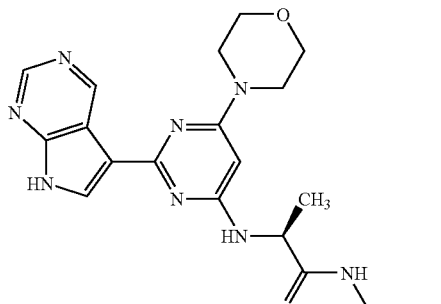
36

TABLE 1-continued
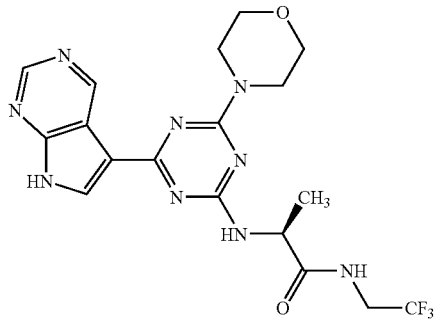
37
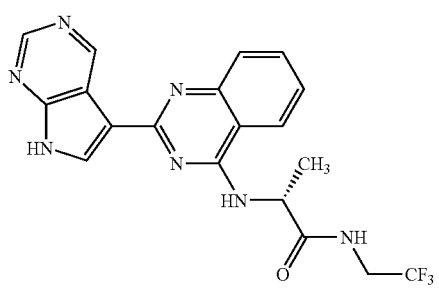
38
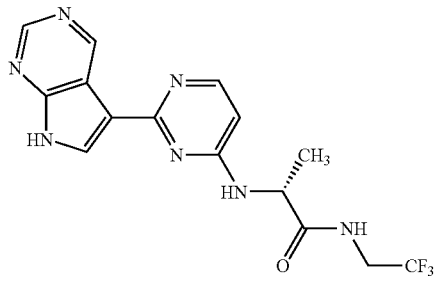
39
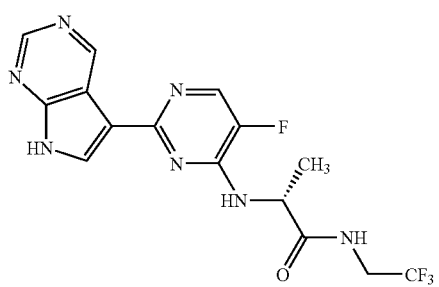
40
TABLE 1-continued
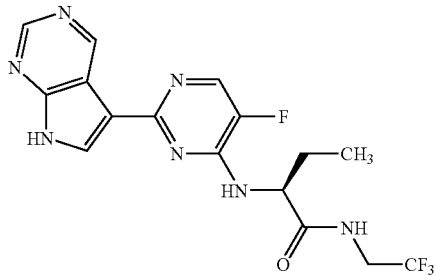
41
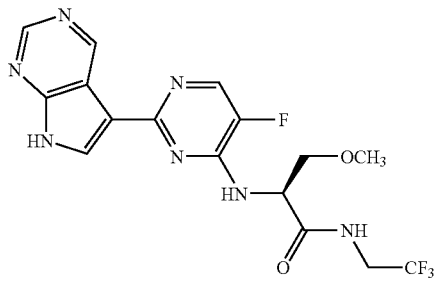
42
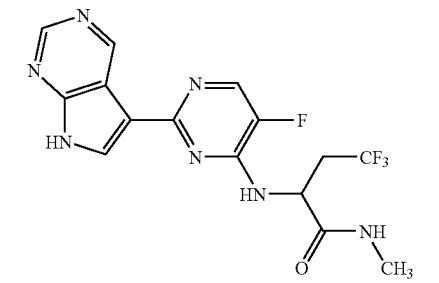
43
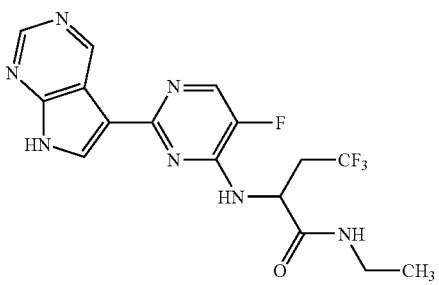
44
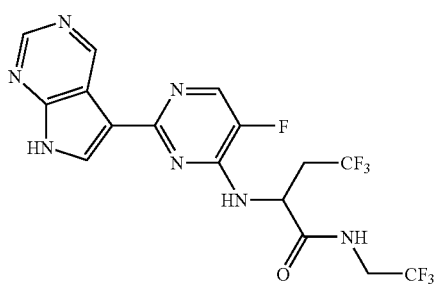
45

TABLE 1-continued
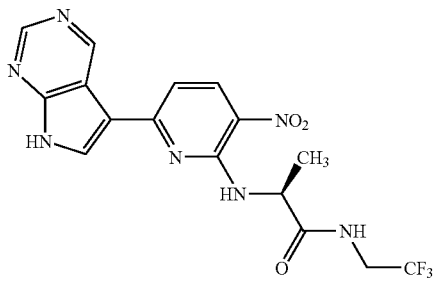
46
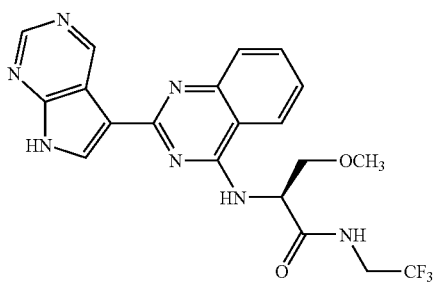
47
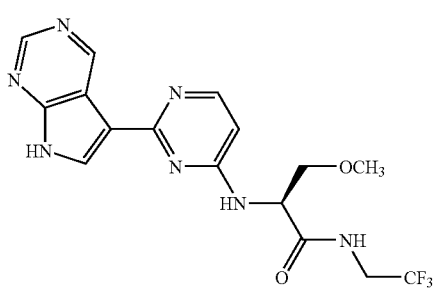
48
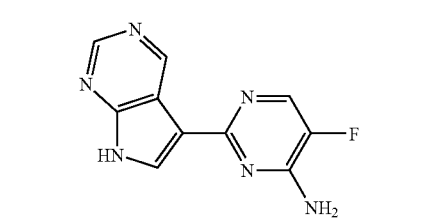
49
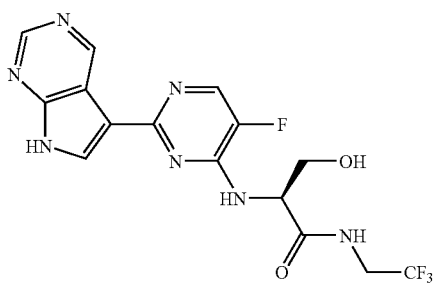
50
TABLE 1-continued
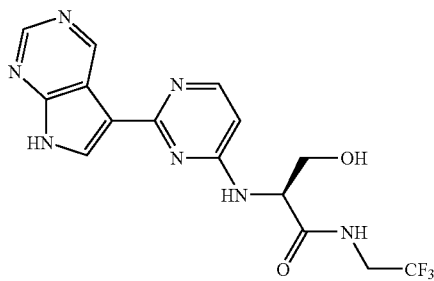
51
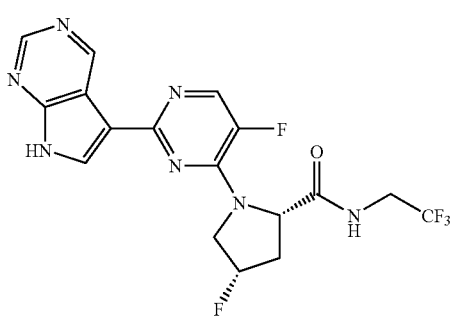
52
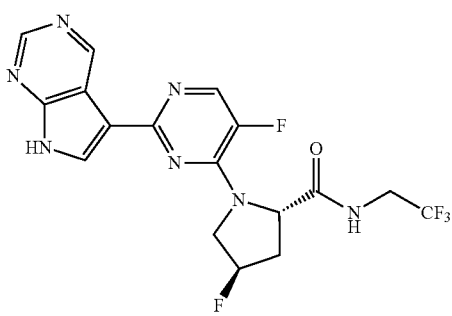
53
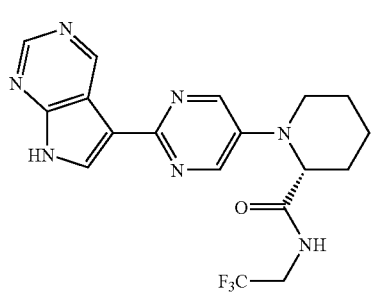
54

TABLE 1-continued
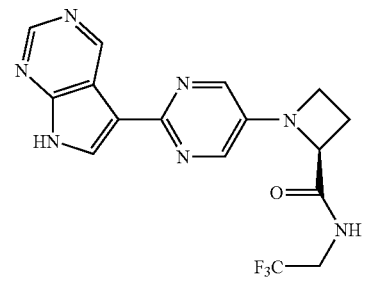
55
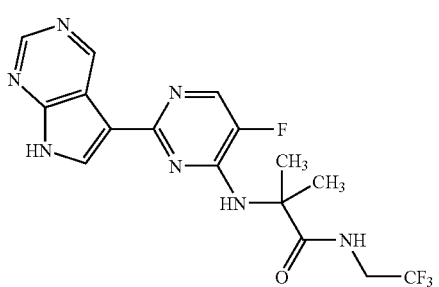
56
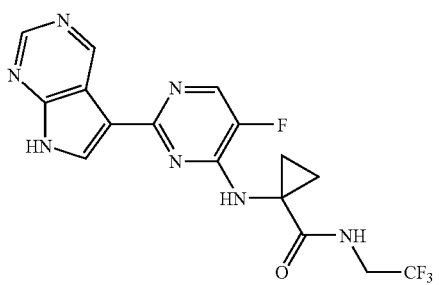
57
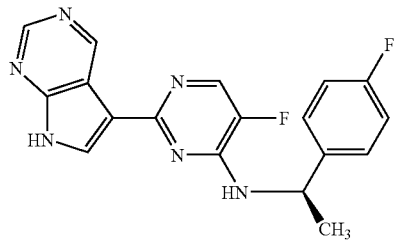
58
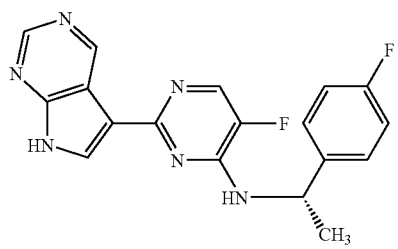
59
TABLE 1-continued
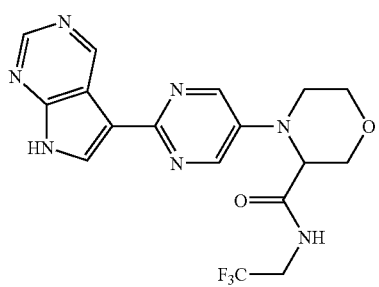
60
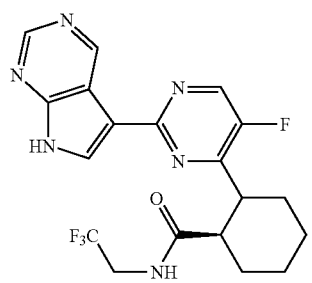
61
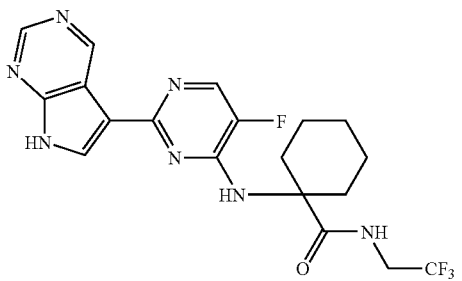
62
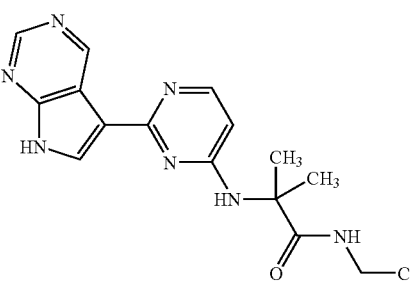
63

TABLE 1-continued
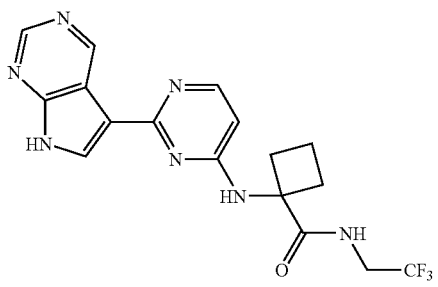
64
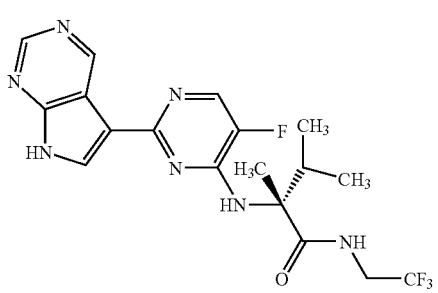
65
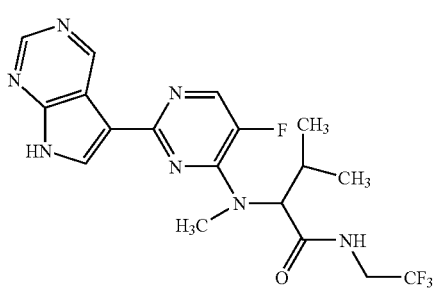
66
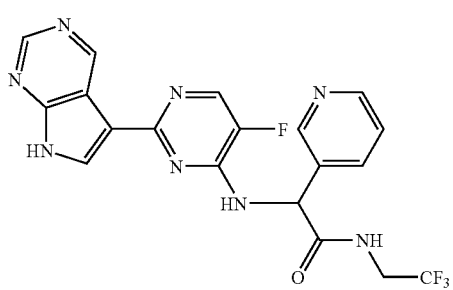
67
TABLE 1-continued
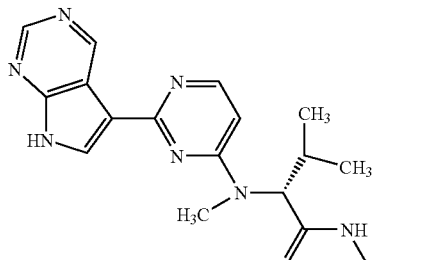
68
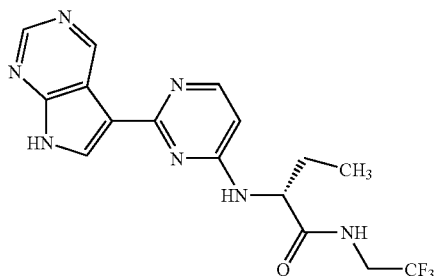
69
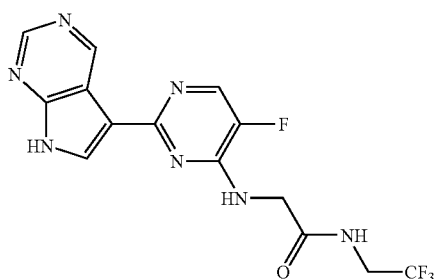
70
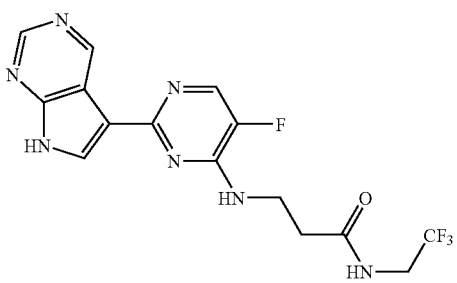
71
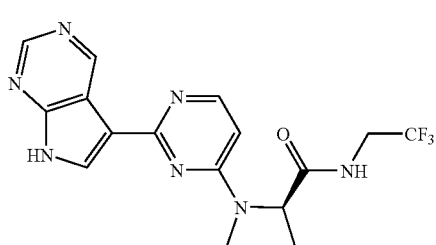
72

TABLE 1-continued
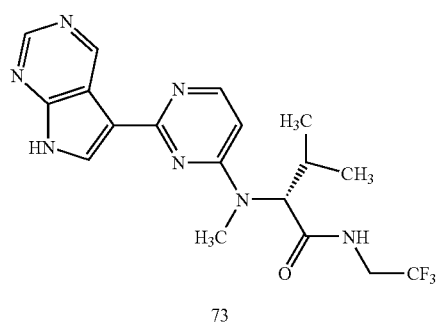
73
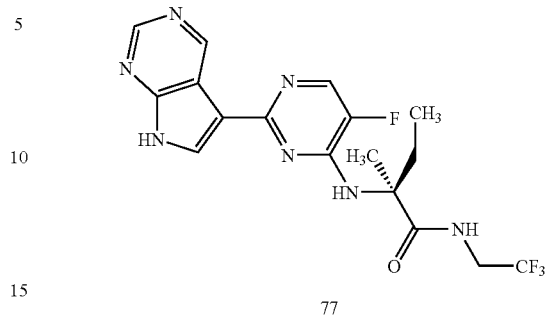
77
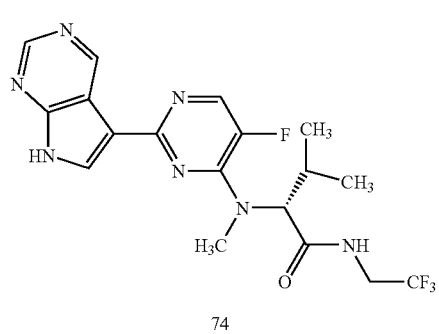 [SMILES: CC(C)[C@H](C(=O)NCC(F)(F)F)N(C)c1nc(-c2c[nH]c3ncncc23)ncc1F]
74
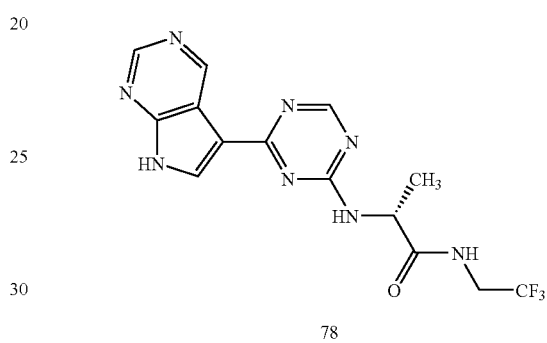
78
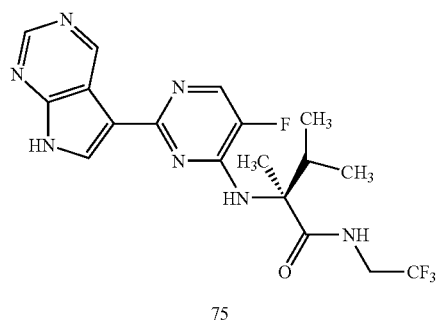 [SMILES: CC(C)[C@](C)(Nc1nc(-c2c[nH]c3ncncc23)ncc1F)C(=O)NCC(F)(F)F]
75
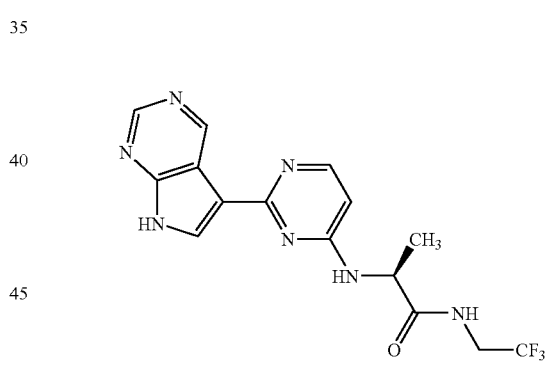
79
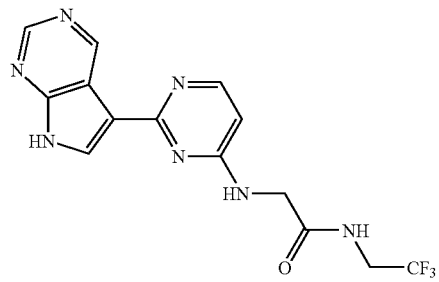
76
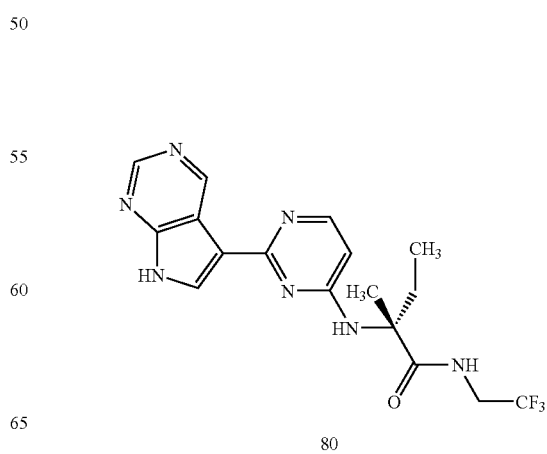
80

TABLE 1-continued
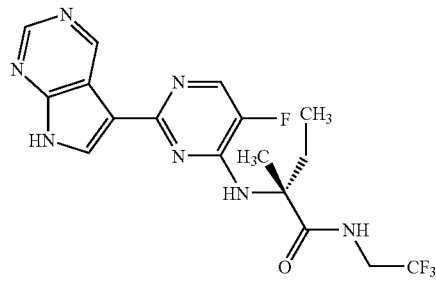
81
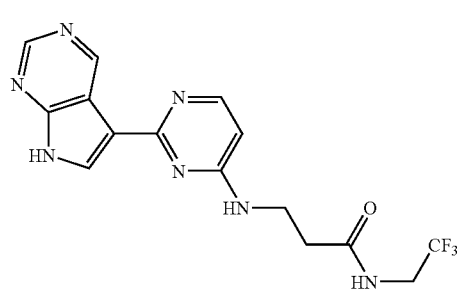
82
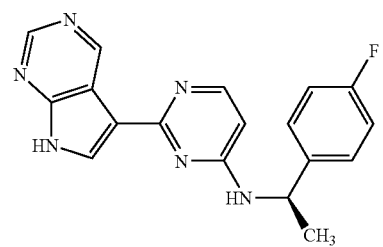
83
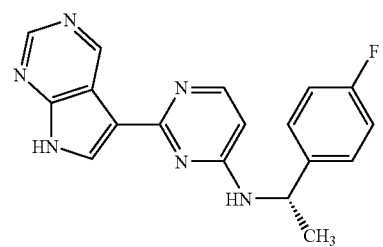
84
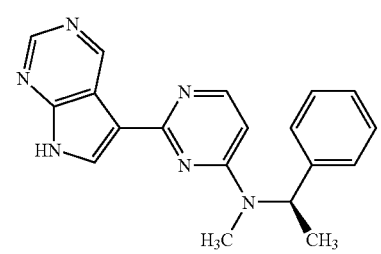
85
TABLE 1-continued
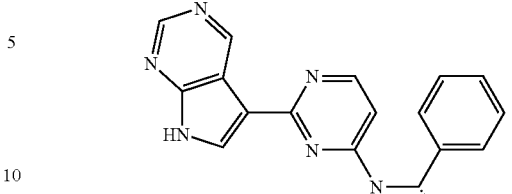
86
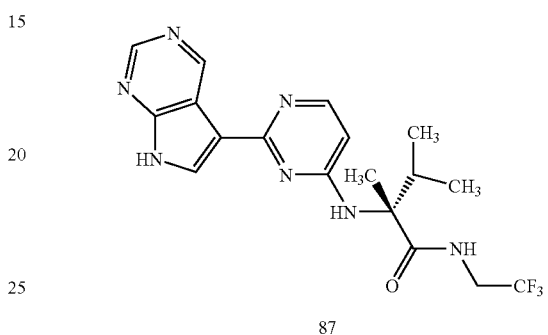
87
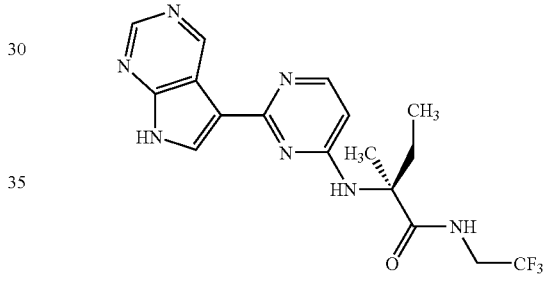
88
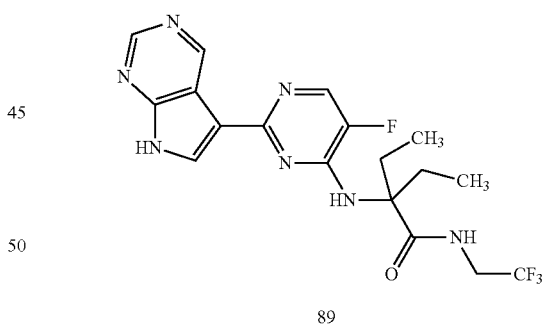
89
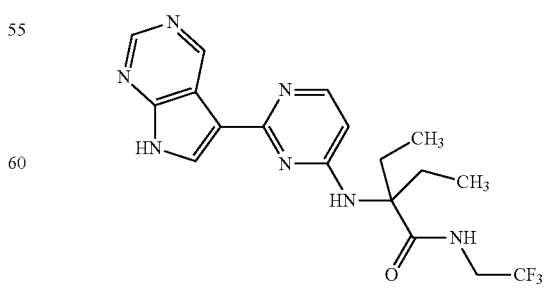
90

TABLE 1-continued
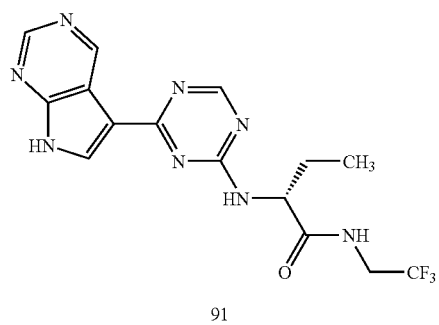 [SMILES: CC[C@@H](Nc1ncnc(-c2c[nH]c3ncncc23)n1)C(=O)NCC(F)(F)F]
91
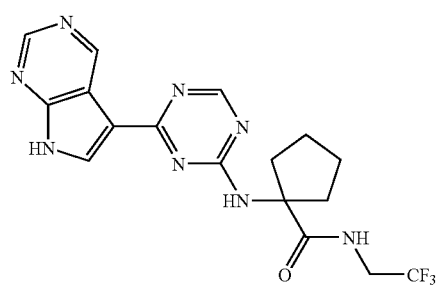
92
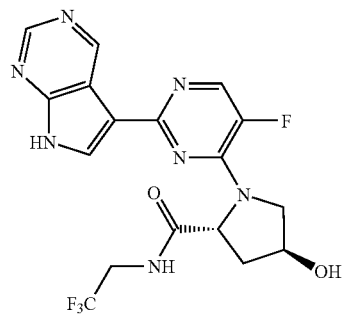
93
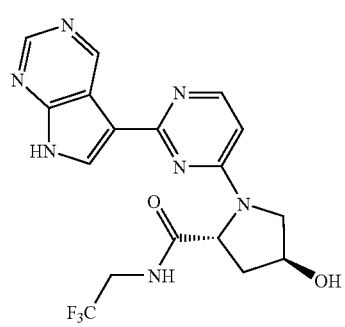
94
TABLE 1-continued
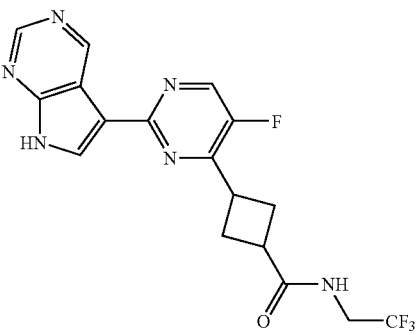
95
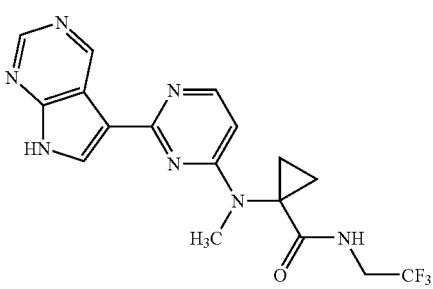
96
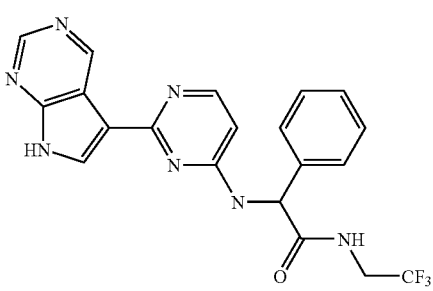
97
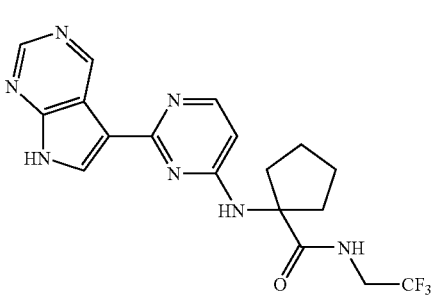
98

TABLE 1-continued
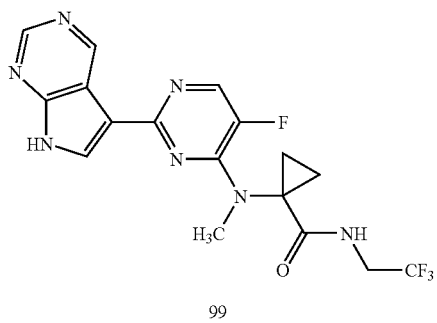 [SMILES: CN(c1nc(-c2c[nH]c3ncncc23)ncc1F)C1(C(=O)NCC(F)(F)F)CC1]
99
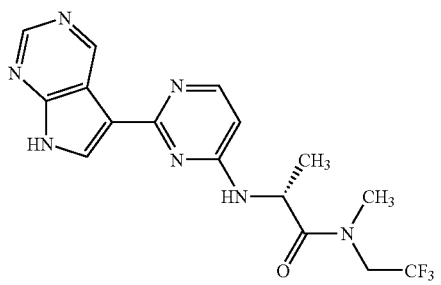
103
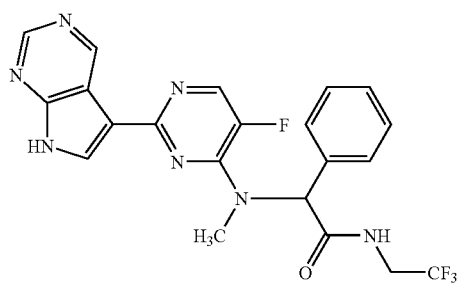
100
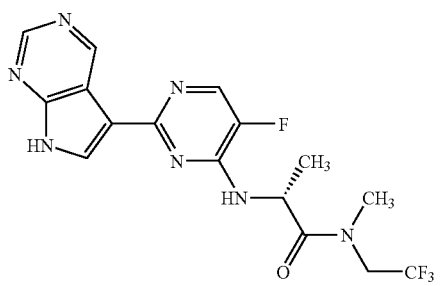
104
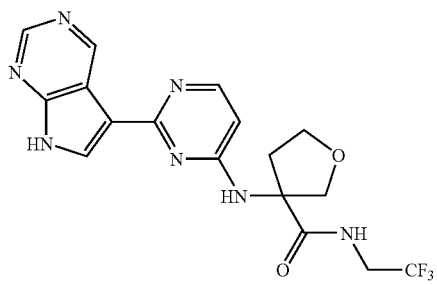
101
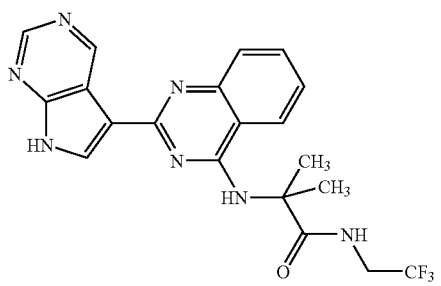
105
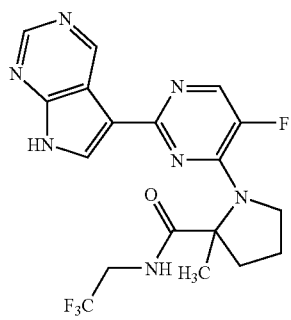
102
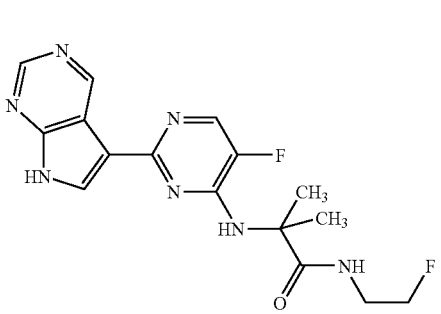
106

TABLE 1-continued

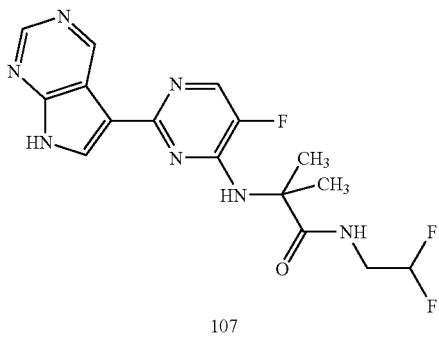 [SMILES: CC(C)(Nc1nc(-c2c[nH]c3ncncc23)ncc1F)C(=O)NCC(F)F]

107

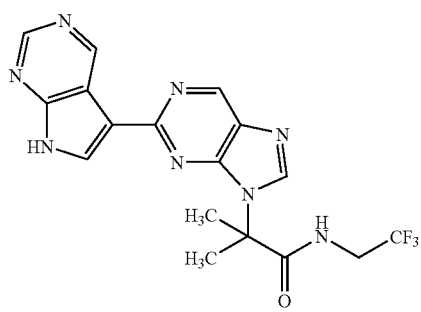

108

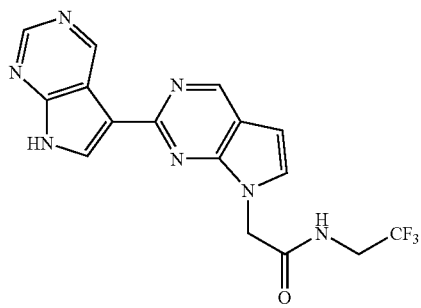

109

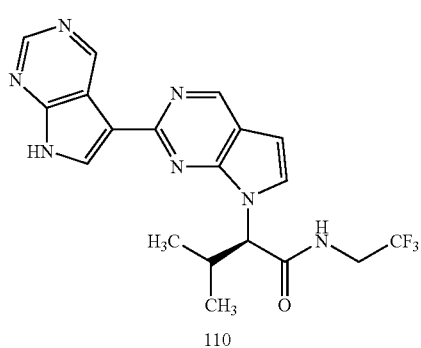 [SMILES: CC(C)[C@H](C(=O)NCC(F)(F)F)n1ccc2cnc(-c3c[nH]c4ncncc34)nc21]

110

TABLE 1-continued

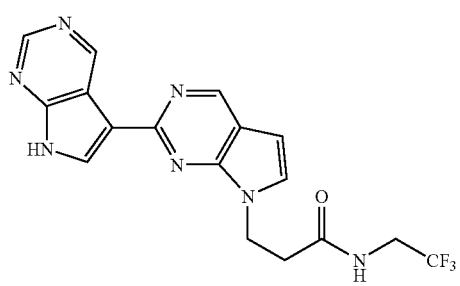

111

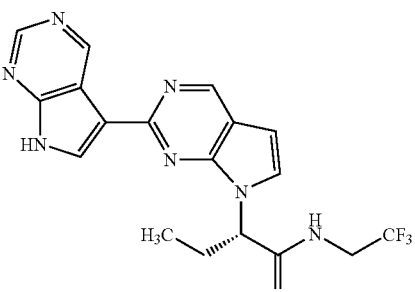

112

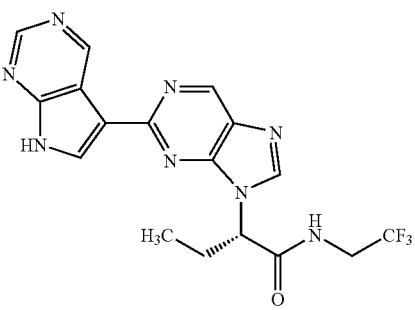

113

Formulation and Administration of Compounds of the Invention

In another embodiment, the invention provides a pharmaceutical composition comprising a compound of formulae I, II-a, II-b, or III.

In a further embodiment, the composition additionally comprises a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly a JAK family kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a JAK family kinase.

Pharmaceutically acceptable salts are well known in the art. For example, S. M. Berge et al., describe pharmaceutically acceptable salts in detail in *J. Pharmaceutical Sciences* 66: 1-19, 1977, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{-alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980); *Remington: The Science and Practice of pharmacy*, 21st edition, 2005, ed. D. B. Troy, Lippincott Williams & Wilkins, Philadelphia; and *Encyclopedia of Pharmaceutical Technology*, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly JAK family activity, between a sample comprising a compound of this invention and a JAK kinase and an equivalent sample comprising JAK kinase in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™ (imatinib mesylate), adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of Compounds and Compositions of the Invention

In another embodiment, the invention provides a method of inhibiting JAK kinase activity in a biological sample, comprising contacting said biological sample with a compound or composition of the invention.

In another embodiment, the invention provides a method of inhibiting JAK kinase activity in a patient, comprising administering to said patient a compound or composition of the invention.

In another embodiment, the invention comprises a method of treating or lessening the severity of a JAK-mediated condition or disease in a patient. The term "JAK-mediated disease", as used herein means any disease or other deleterious condition in which a JAK family kinase, in particular JAK2 or JAK3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas.

In another embodiment, the invention provides a method of treating or lessening the severity of a disease of condition selected from a proliferative disorder, a cardiac disorder, a neurodegenerative disorder, an autoimmune disorder, a condition associated with organ transplant, an inflammatory disorder, an immune disorder or an immunologically mediated disorder, comprising administering to said patient a compound or composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In one embodiment, the disease or disorder is allergic or type I hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection.

In another embodiment, a compound or composition of this invention may be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML or juvenile myelomonocytic leukemia.

The term "biological sample", as used herein, means a sample outside a living organism, and includes, without limitation, cell cultures or extracts thereof; biopsied material obtained from a mammal or extracts thereof; and blood, saliva, urine, feces, semen, tears, or other body fluids or extracts thereof.

Inhibition of kinase activity, particularly JAK kinase activity, in a biological sample is useful for a variety of purposes that are known to one of skill in the art. Examples of such purposes include, but are not limited to, blood transfusion, organ-transplantation, biological specimen storage, and biological assays.

In certain embodiments of the present invention an "effective amount" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like.

In an alternate embodiment, the methods of this invention comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylacetic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

Preparation of Compounds of the Invention

The compounds of this invention may be prepared in general by methods known to those skilled in the art for analogous compounds or by those methods depicted in the Examples below.

The following definitions describe terms and abbreviations used herein:

| | |
|---|---|
| Ac | acetyl |
| atm | atmosphere |
| ATP | adenosine triphosphate |
| Boc | tert-butoxycarbonyl |
| BSA | bovine serum albumin |
| Bu | butyl |
| DCM | dichloromethane |
| DIEA | diisopropylethylamine (also DIPEA) |
| DME | 1,2-Dimethoxyethane |
| DMF | dimethylformamide |
| DMSO | dimethyl sulfoxide |
| dppf | 1,1'-bis(diphenylphosphino)-ferrocene |
| DTT | dithiothreitol |
| EDC | 1-Ethyl-3-(3-dimethylaminopropy)carbodiimide hydrochloride |
| Et | ethyl |
| EtOAc | ethyl acetate |
| Glu | glutamic acid or glutamyl |
| HBTU | O-benzotriazol-1-yl-N,N,N',N'-tetramethyluronium hexafluorophosphate |
| HEPES | 4-(2-hydroxyethyl)-1-piperazineethanesulfonic acid |
| HOBT | hydroxybenzotriazole |
| Me | methyl |
| MW | microwave |
| NMP | N-methylpyrrolidone |
| Ph | phenyl |
| rt | room temperature |
| R.T. | retention time |
| TFA | trifluoacetic acid |
| THF | tetrahydrofuran |
| Ts | toluenesulfonyl |
| Tyr | tyrosine or tyrosyl |

EXAMPLES

Example 1a

Preparation of 5-(4,4,5,5-tetramethyl-1,3,2-dioxaborolan-2-yl)-7-tosyl-7H-pyrrolo[2,3-d]pyrimidine (Compound 1005)

As shown in FIG. 1—step i, 4-chloro-7H-pyrrolo[2,3-d] pyrimidine (compound 1001) (130 mg, 0.847 mmol) was dissolved in 3 mL of methanol and hydrogenated under 1 atm of hydrogen over Pd—C 10% for 16 hours. Concentration to dryness provided 100 mg (98%) of 7H-pyrrolo[2,3-d]pyrimidine [compound 1002, $^1$H-NMR (CD$_3$OD): δ 9.4 (s, 1H); 9.1 (s, 1H); 7.9 (s, 1H); 7.1 (s, 1H)].

As shown in FIG. 1—steps ii & iii, bromine (134 mg, 0.839 mmol) in DMF (2 mL) was added to a solution of compound 1002 (100 mg, 0.839 mmol) in 3 mL of DMF and the reaction mixture was stirred at rt for 2 hours. The mixture was then poured into ice-water and treated with aqueous sodium thiosulfate and potassium carbonate. The aqueous phase was extracted with EtOAc, washed with brine, dried with MgSO$_4$ and concentrated to give 120 mg of compound 1003 as a solid residue that was used directly for the next step. Sodium hydride (32 mg, 1.22 mmol) was added to a stirred solution of compound 1003 (120 mg, 0.61 mmol) in 3 mL of dry THF at 0° C. The reaction mixture was stirred at rt for 1 hour. Toluene sulfonyl chloride (128 mg, 0.67 mmol) was added to the reaction mixture, which was then stirred at rt for an additional 1 hour. The volatiles were removed in vacuo and the residue diluted with ice-water, neutralized with saturated NH$_4$Cl aqueous solution and extracted with EtOAc (3×). The combined organics were washed with brine, dried (Na$_2$SO$_4$) and concentrated in vacuo to a solid, which was purified by chromatography (silica gel, 30% EtOAc/hexanes) to provide 143 mg (67% yield; 2 steps) of 5-bromo-7-tosyl-7H-pyrrolo[2,3-d]pyrimidine [compound 1004, $^1$H-NMR (DMSO-d$_6$): δ 9.1 (d, 2H); 8.3 (s, 1H); 8.0 (d, 2H); 7.5 (d, 2H); 2.4 (s, 3H)].

As shown in FIG. 1—step iv, a mixture of compound 1004 (140 mg, 0.40 mmol), 4,4,5,5-tetramethyl-1,3,2-dioxaborolane dimer (121 mg, 0.477 mmol), PdCl$_2$ dppf$_2$ (16 mg, 0.02 mmol) and potassium acetate (117 mg, 1.19 mmol) in 2 mL of DME were microwaved at 150° C. for 10 minutes. The reaction mixture was filtered through a short pad of silica gel with 30% EtOAc-70% hexanes as eluent to provide, after concentration to dryness, 158 mg (98%) of 5-(4,4,5,5-tetramethyl-1,3,2-dioxaborolan-2-yl)-7-tosyl-7H-pyrrolo[2,3-d]pyrimidine, compound 1005: ESMS M+1=317.07.

Example 1b

Preparation of (S)-2-(5-fluoro-2-(7H-pyrrolo[2,3-d] pyrimidin-5-yl)pyrimidin-4-ylamino)-N-(2,2,2-trifluoroethyl)propanamide (Compound 6)

Figure 2:
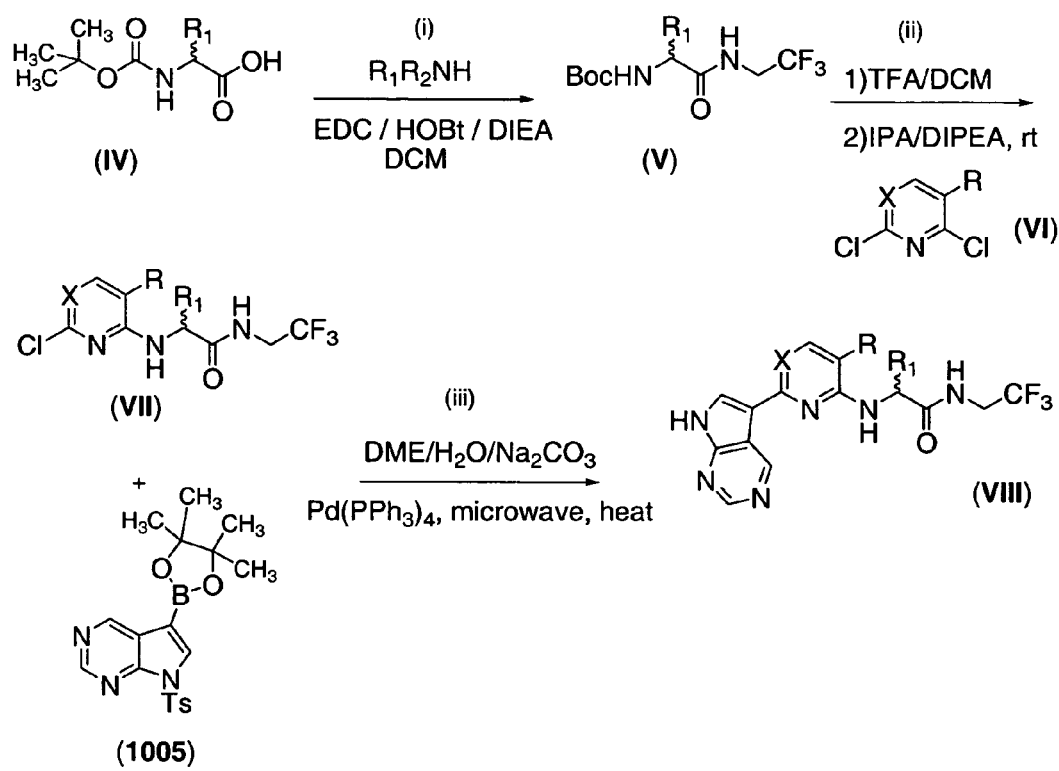
FIG. 2 is a scheme showing the synthesis of a compound of formula VIII from a compound of formula IV.

As shown in FIG. 2—step i), to a stirred solution of the compound of formula IV, where R is a methyl group with the S-configuration (Boc-L-alanine, compound 1006, 3.8 g, 0.02 mol), EDC (4.63 g, 0.024 mol), HOBt (4.0 g, 0.026 mol), DIEA (10.5 mL, 0.06 mol) in 100 mL of DCM was added trifluoroethylamine HCl (2.92 g, 0.022 mol). The reaction mixture was stirred for 16 hours. The volatiles were removed in vacuo and the resulting residue dissolved in EtOAc, washed successively with 0.5N HCl, saturated aqueous solution of NaHCO$_3$, and brine. The organics were dried (Na$_2$SO$_4$) and concentrated in vacuo to give a compound of formula V, where R$^1$ is CH$_3$ (tert-butyl(S)-1-(2,2,2-trifluoroethylcarbamoyl)ethylcarbamate, compound 1007) as a white solid (5.4 g, 98% yield), $^1$H-NMR (CDCl$_3$): δ 6.9 (bs, 1H); 4.9 (bs, 1H); 4.1 (bs, 1H); 3.8 (bs, 2H); 1.4 (s, 9H); 1.3 (d, 3H).

As shown in FIG. 2—step ii, compound 1007 (5.32 g, 0.0197 mol) was treated with a 1:1 mixture of DCM/TFA at rt for 45 min. Concentration to dryness gave intermediate amine, (S)-2-amino-N-(2,2,2-trifluoroethyl)propanamide, as the TFA salt, which was used directly in the next reaction. Accordingly, a mixture of a compound of formula VI, where R is fluoro(5-fluoro-2,4-dichloropyrimidine, compound 1008, 3.28 g, 0.0197 mol), the crude amine TFA salt from directly above (5.25 g, 0.0197 mol), and DIEA (10.27 mL, 0.059 mol) were stirred in isopropanol at rt for 16 hours. The reaction mixture was concentrated in vacuo, the residue dissolved in EtOAc, and the organics washed successively with 0.5N HCl, a saturated aqueous solution of NaHCO$_3$, and brine. The organics were dried (Na$_2$SO$_4$) and concentrated in vacuo to give a crude oil that was purified by silica gel chromatography (50% EtOAc/hexanes) to produce compound 1009 (a compound of formula VII, wherein R is fluoro, R$^1$ is CH$_3$, and X is N (4.21 g, 71% yield), $^1$H-NMR (DMSO-d$_6$): δ 9.7 (d, 1H); 8.7 (t, 1H); 4.4 (q, 1H); 4.0-3.8 (m, 2H); 1.3 (d, 3H).

As shown in FIG. 2—step iii, a mixture of compound 1005 (30 mg, 0.075 mmol), compound 1009 (23 mg, 0.075 mmol), Pd(Ph$_3$P)$_4$ (9 mg, 0.0078 mmol), and sodium carbonate 2M (115 uL, 0.23 mmol) in 1 mL of DME were microwaved at 150° C. for 10 minutes. The reaction mixture was filtered through a short pad of silica gel using 30% EtOAc-70% hexanes as eluent to provide, after concentration to dryness, a crude intermediate tosylate that was used directly for the next step. The crude intermediate was dissolved in 1 mL of dry methanol and 200 uL of 25% sodium methoxide in methanol was added. The reaction mixture was stirred at 60° C. for 1 hour and quenched with 6N HCl (154 uL). After drying the reaction mixture under a flow of nitrogen, the product was purified by reversed-phase HPLC (gradient: 10-60% MeCN/water with 0.5% TFA) to provide 19.6 mg (68%) of compound 6 (a compound of formula VIII, wherein R=F, R$^1$=CH$_3$ with the S-configuration, and X=N).

Example 2

Preparation of (S)-2-(2-(7H-pyrrolo[2,3-d]pyrimidin-5-yl)pyrimidin-4-ylamino)-N-(2,2,2-trifluoroethyl) propanamide (Compound 5)

The title compound was prepared using the procedure of Example 1b, with the procedural change of replacing 5-fluoro-2,4-dichloropyrimidine (compound 1008) with 2,4-dichloropyrimidine. Accordingly, compound 5 (a compound of formula VIII, where R=H, R$^1$=Me, and X=N) was isolated (10.8 mg, 40% yield).

Example 3

Preparation of (S)-2-(6-(7H-pyrrolo[2,3-d]pyrimidin-5-yl)pyridin-2-ylamino)-N-(2,2,2-trifluoroethyl)propanamide (Compound 4)

The title compound was prepared using the procedure of Example 1b, with the procedural change of replacing 5-fluoro-2,4-dichloropyrimidine (compound 1008) with 1,6-dibromopyridine. Accordingly, compound 4 (a compound of formula VIII, where R=H, R$^1$=Me, and X=CH) was isolated (12.4 mg, 45% yield).

Example 4

Preparation of 1-((2S,6R)-4-(6-(7H-pyrrolo[2,3-d]pyrimidin-5-yl)pyridin-2-yl)-2,6-dimethylpiperazin-1-yl)ethanone (Compound 1)

The title compound was prepared using the procedure of Example 1b, with the procedural change of replacing (S)-2-amino-N-(2,2,2-trifluoroethyl)propanamide with 1-(2,6-dimethylpiperazin-1-yl)ethanone and 5-fluoro-2,4-dichloropyrimidine (compound 1008) with 1,6-dibromoropyridine. Accordingly, compound I with the following structure was isolated (50 mg, 75% yield):

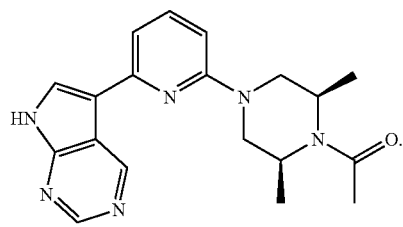 [SMILES: CC(=O)N1[C@H](C)CN(c2cccc(-c3c[nH]c4ncncc34)n2)C[C@@H]1C]

Example 5

Preparation of ((S)-1-(5-fluoro-2-(7H-pyrrolo[2,3-d]pyrimidin-5-yl)pyrimidin-4-yl)pyrrolidin-2-yl) methanol (Compound 21)

The title compound was prepared using the procedure of Example 1b, with the procedural change of replacing (S)-2-amino-N-(2,2,2-trifluoroethyl)propanamide with (S)-pyrrolidinol.

Example 6

Preparation of ((R)-1-(5-fluoro-2-(7H-pyrrolo[2,3-d]pyrimidin-5-yl)pyrimidin-4-yl)pyrrolidin-2-yl) methanol (Compound 22)

The title compound was prepared using the procedure of Example 1b, with the procedural change of replacing (S)-2-amino-N-(2,2,2-trifluoroethyl)propanamide with (R)-pyrrolidinol.

Example 7

Preparation of 5-(5-fluoro-4-((S)-2-(methoxymethyl) pyrrolidin-1-yl)pyrimidin-2-yl)-7H-pyrrolo[2,3-d] pyrimidine (Compound 23)

The title compound was prepared using the procedure of Example 1b, with the procedural change of replacing (S)-2-amino-N-(2,2,2-trifluoroethyl)propanamide with (S)-methoxymethyl pyrrolidine.

Example 8

Preparation of 5-(5-fluoro-4-(pyrrolidin-1-yl)pyrimidin-2-yl)-7H-pyrrolo[2,3-d]pyrimidine (Compound 24)

The title compound was prepared using the procedure of Example 1b, with the procedural change of replacing (S)-2-amino-N-(2,2,2-trifluoroethyl)propanamide with pyrrolidine.

Example 9

Preparation of 5-(5-fluoro-4-((R)-2-(methoxymethyl)pyrrolidin-1-yl)pyrimidin-2-yl)-7H-pyrrolo[2,3-d]pyrimidine (Compound 25)

The title compound was prepared using the procedure of Example 1b, with the procedural change of replacing (S)-2-amino-N-(2,2,2-trifluoroethyl)propanamide with (R)-methoxymethyl pyrrolidine.

Example 10

Preparation of (S)-1-(5-fluoro-2-(7H-pyrrolo[2,3-d]pyrimidin-5-yl)pyrimidin-4-yl)-N-(2,2,2-trifluoroethyl)pyrrolidine-2-carboxamide)

The title compound was prepared using the procedure of Example 1b, with the procedural change of replacing tert-butyl(S)-1-(2,2,2-trifluoroethylcarbamoyl)ethylcarbamate with (S)-1-(tert-butoxycarbonyl)pyrrolidine-2-carboxylic acid. Accordingly, the following compound was isolated (9.5 mg, 45%):

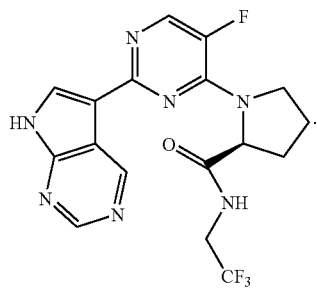 [SMILES: O=C(NCC(F)(F)F)[C@@H]1CCCN1c1nc(-c2c[nH]c3ncncc23)ncc1F]

Example 11

Preparation of (R)-1-(5-fluoro-2-(7H-pyrrolo[2,3-d]pyrimidin-5-yl)pyrimidin-4-yl)-N-(2,2,2-trifluoroethyl)pyrrolidine-2-carboxamide)

The title compound was prepared using the procedure of Example 1b, with the procedural change of replacing tert-butyl(S)-1-(2,2,2-trifluoroethylcarbamoyl)ethylcarbamate with (R)-1-(tert-butoxycarbonyl)pyrrolidine-2-carboxylic acid. Accordingly, the following compound was isolated (9.2 mg, 38%):

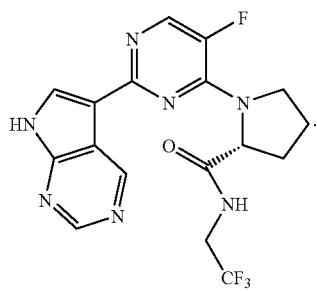 [SMILES: O=C(NCC(F)(F)F)[C@H]1CCCN1c1nc(-c2c[nH]c3ncncc23)ncc1F]

Example 12

Preparation of (R)-2-(2-(7H-pyrrolo[2,3-d]pyrimidin-5-yl)pyrimidin-4-ylamino)-N-(2,2,2-trifluoroethyl)propanamide (Compound 39)

The title compound was prepared using the procedure of Example 2, with the procedural change of using tert-butyl(R)-1-(2,2,2-trifluoroethylcarbamoyl)ethylcarbamate as the starting material to provide a compound of formula VIII, wherein R=H, $R^1$=Me, and X=N.

Example 13

Preparation of (R)-2-(5-fluoro-2-(7H-pyrrolo[2,3-d]pyrimidin-5-yl)pyrimidin-4-ylamino)-N-(2,2,2-trifluoroethyl)propanamide (Compound 40)

The title compound was prepared using the procedure of Example 1b, with the procedural change of using tert-butyl (R)-1-(2,2,2-trifluoroethylcarbamoyl)ethylcarbamate as the starting material to provide a compound of formula VIII, wherein R=F, $R^1$=Me, and X=N.

Example 14

Preparation of (S)-2-(5-fluoro-2-(7H-pyrrolo[2,3-d]pyrimidin-5-yl)pyrimidin-4-ylamino)-N-(2,2,2-trifluoroethyl)butanamide (Compound 41)

The title compound was prepared using the procedure of Example 1b, with the procedural change of using tert-butyl (S)-1-(2,2,2-trifluoroethylcarbamoyl)propylcarbamate as the starting material to provide a compound of formula VIII, wherein R=F, $R^1$=Et, and X=N.

Example 15

Preparation of (S)-2-(5-fluoro-2-(7H-pyrrolo[2,3-d]pyrimidin-5-yl)pyrimidin-4-ylamino)-N-(2,2,2-trifluoroethyl)-3-methoxypropanamide (Compound 42)

The title compound was prepared using the procedure of Example 1b, with the procedural change of using tert-butyl (S)-1-(2,2,2-trifluoroethylcarbamoyl)-2-methoxyethylcarbamate as the starting material to provide a compound of formula VIII, wherein R=F, $R_1$=CH$_2$OMe, and X=N.

Example 16

Preparation of (S)-2-(2-(7H-pyrrolo[2,3-d]pyrimidin-5-yl)pyrimidin-4-ylamino)-N-(2,2,2-trifluoroethyl)-3-methoxypropanamide (Compound 48)

The title compound was prepared using the procedure of Example 1b, with the procedural change of using tert-butyl (S)-1-(2,2,2-trifluoroethylcarbamoyl)-2-methoxyethylcarbamate as the starting material to provide a compound of formula VIII, wherein R=H, $R_1$=CH$_2$OMe, and X=N.

Example 17

Preparation of 2-(5-fluoro-2-(7H-pyrrolo[2,3-d]pyrimidin-5-yl)pyrimidin-4-ylamino)-4,4,4-trifluoro-N-methylbutanamide (Compound 43)

The title compound was prepared using the procedure of Example 1b, with the procedural change of using tert-butyl 1-(methylcarbamoyl)-3,3,3-trifluoropropylcarbamate as the starting material to provide a compound of formula VIII, wherein R=F, $R_1$=$CH_2CF_3$, and X=N.

Example 18

Preparation of 2-(5-fluoro-2-(7H-pyrrolo[2,3-d]pyrimidin-5-yl)pyrimidin-4-ylamino)-N-ethyl-4,4,4-trifluorobutanamide (Compound 44)

The title compound was prepared using the procedure of Example 1b, with the procedural change of using tert-butyl 1-(ethylcarbamoyl)-3,3,3-trifluoropropylcarbamate as the starting material to provide a compound of formula VIII, wherein R=F, $R_1$=$CH_2CF_3$ and X=N.

Example 19

Preparation of 2-(5-fluoro-2-(7H-pyrrolo[2,3-d]pyrimidin-5-yl)pyrimidin-4-ylamino)-4,4,4-trifluoro-N-(2,2,2-trifluoroethyl)butanamide (Compound 45)

The title compound was prepared using the procedure of Example 1b, with the procedural change of using tert-butyl 1-(2,2,2-trifluoroethylcarbamoyl)-3,3,3-trifluoropropylcarbamate as the starting material to provide a compound of formula VIII, wherein R=F, $R_1$=$CH_2CF_3$, and X=N.

Example 20

Preparation of 2-(5-fluoro-2-(7H-pyrrolo[2,3-d]pyrimidin-5-yl)pyrimidin-4-ylamino)-N-(2,2,2-trifluoroethyl)-2-methylpropanamide (Compound 56)

The title compound was prepared using the procedure of Example 1b, with the procedural change of replacing the tert-butyl(S)-1-(2,2,2-trifluoroethylcarbamoyl)ethylcarbamate with tert-butyl 2-(2,2,2-trifluoroethylcarbamoyl)propan-2-ylcarbamate. Accordingly, the following compound was isolated:

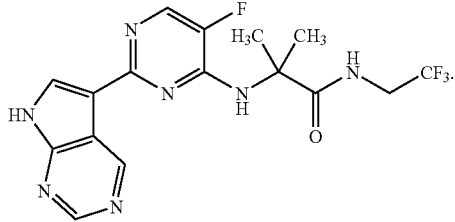 [SMILES: CC(C)(Nc1nc(-c2c[nH]c3ncncc23)ncc1F)C(=O)NCC(F)(F)F]

Example 21

Preparation of (S)-2-(6-phenyl-2-(7H-pyrrolo[2,3-d]pyrimidin-5-yl)pyrimidin-4-ylamino)-N-(2,2,2-trifluoroethyl)propanamide (Compound 18)

Figure 3:
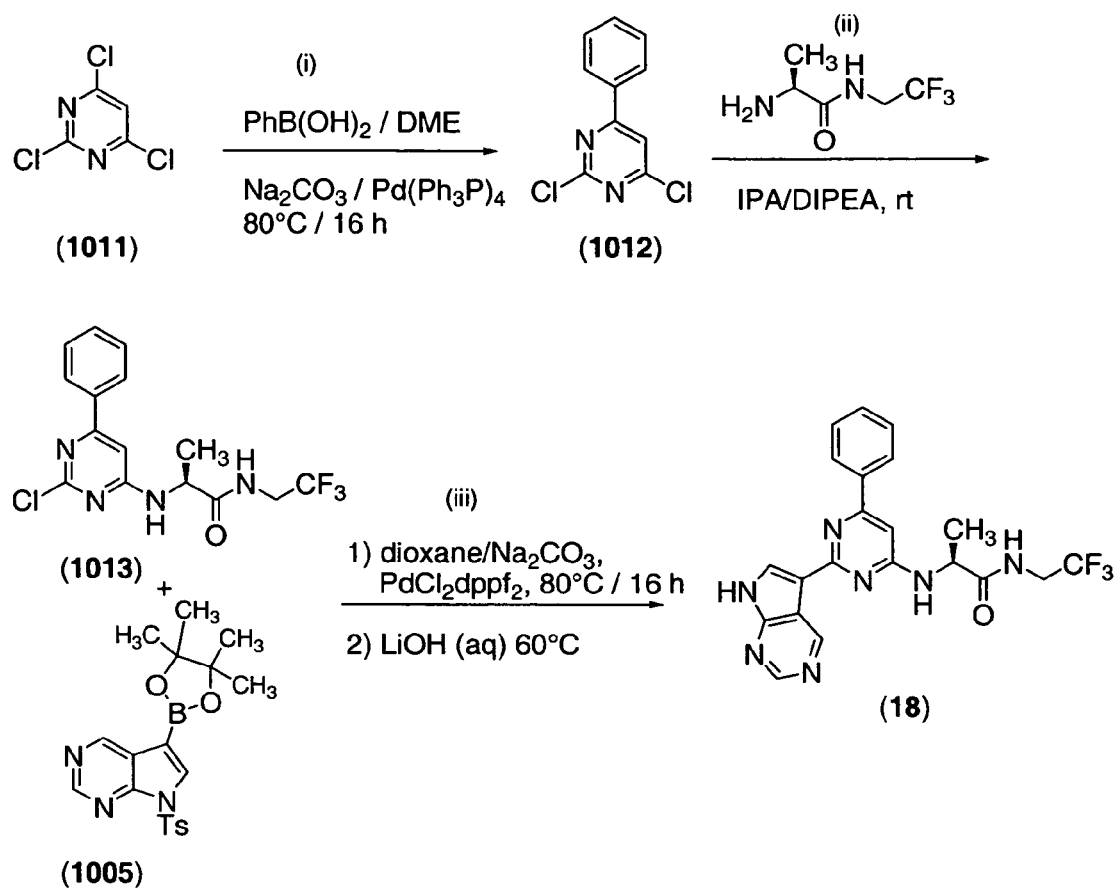
FIG. 3 is a scheme showing the synthesis of compound 18 from compound 1011.

As shown in FIG. 3—step i, a mixture of phenylboronic acid (1.22 g), 2,4,6-trichloropyrimidine (compound 1011), tetrakis(triphenylphosphine) palladium(0) and 2N sodium carbonate (15 mL) in DME (25 mL) was heated at 80° C. overnight. After cooling to rt, addition of water (30 mL), extraction with dichloromethane (3×20 mL), drying and evaporation, purification by column chromatography (SiO$_2$, 10-20% ethyl acetate in hexane) afforded the desired product, 6-phenyl-2,4-dichloropyrimidine (compound 1012) (0.544 g). As shown in FIG. 3—step ii, compound 1012 (0.34 g) was mixed with (S)-2-amino-N-(2,2,2-trifluoroethyl)propanamide (0.3 g) and diisopropylethylamine (0.63 mL) in isopropanol (5 mL) and the reaction mixture heated at 80° C. overnight. Evaporation gave a residue, which after aqueous workup and purification (SiO$_2$, 20% ethyl acetate/hexane) produced 2-(2-chloro-6-phenyl-pyrimidin-4-ylamino)-N-(2,2,2-trifluoro-ethyl)propionamide (compound 1013) (0.165 g). As shown in FIG. 3—step iii, compound 1013 (29 mg), 5-(4,4,5,5-Tetramethyl-[1,3,2]dioxaborolan-2-yl)-7-(toluene-4-sulfonyl)-7H-pyrrolo[2,3-d]pyrimidine (compound 1005), PdCl$_2$dppf$_2$ (7 mg), and potassium phosphate (32 mg) were heated in 1,4-dioxane (2 mL) at 80° C. overnight. To the reaction was added aqueous lithium hydroxide solution (2 mL). After heating at 60° C. for 1 h, water (20 mL) was added. Extraction with dichloromethane (3×), drying, evaporation and purification (SiO$_2$, 50-100% ethyl acetate/hexane) gave 3.7 mg of 2-[6-phenyl-2-(7H-pyrrolo[2,3-d]pyrimidin-5-yl)-pyrimidin-4-ylamino]-N-(2,2,2-trifluoro-ethyl)-propionamide (compound 18).

Example 22

Preparation of (S)-2-(4,6-dichloropyrimidin-2-ylamino)-N-(2,2,2-trifluoroethyl)propanamide (compound 1019) and (S)-2-(2,6-dichloropyrimidin-4-ylamino)-N-(2,2,2-trifluoroethyl)propanamide (Compound 1020)

Figure 4:
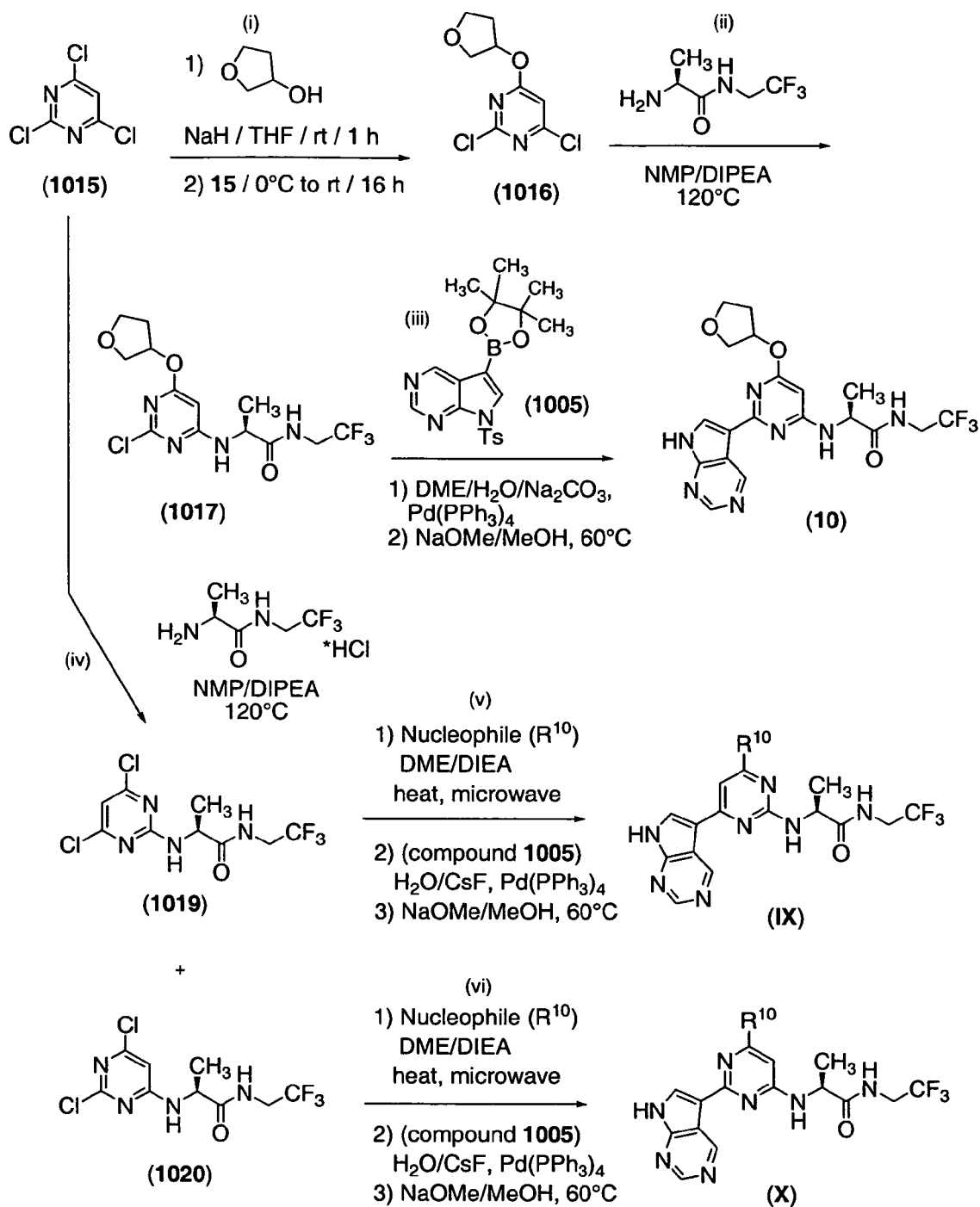
FIG. 4 is a scheme showing the syntheses of compound 10 and compounds having formulae IX and X from compound 1015.

As shown in FIG. 4—step i, to a solution of 3-hydroxytetrahydrofuran (446 mg, 5.00 mmol) in tetrahydrofuran (50 mL) at room temperature was added sodium hydride (60% w/w in mineral oil, 144 mg, 6.00 mmol). After stirring for 1 hour, the mixture was cooled to 0° C. and 2,4,6-trichloropyrimidine (compound 1015) (917 mg, 5.00 mmol) was added. The mixture was warmed to room temperature and stirred overnight. Cold water was added and the mixture extracted with ethyl acetate. The organic phase was dried over magnesium sulfate and concentrated. The residue was purified by silica gel chromatography (0-30% ethyl acetate in hexanes) to give a mixture of isomers, 2,4-dichloro-6-(tetrahydrofuran-3-yloxy)-pyrimidine (compound 1016) and its regioisomer 4,6-chloro-2-(tetrahydrofuran-3-yloxy)-pyrimidine (62:28, respectively, by $^1$H-NMR, 1.17 g, 100%), as a colorless oil.

As shown in FIG. 4—step ii, (S)-2-(2-chloro-6-(tetrahydrofuran-3-yloxy)pyrimidin-4-ylamino)-N-(2,2,2-trifluoroethyl)propanamide (compound 1017) was prepared according to the procedure of Example 1b.

As shown in FIG. 4—step iii, (S)-2-(6-(7H-pyrrolo[2,3-d]pyrimidin-5-yl)-4-(tetrahydrofuran-3-yloxy)pyridin-2-ylamino)-N-(2,2,2-trifluoroethyl)propanamide (compound 10) was prepared according to the procedure of Example 1b.

As shown in FIG. 4—step iv, to a solution of compound 1015 (1.83 g, 10.0 mmol) in ethanol (20 mL) at rt was added 2-amino-N-(2,2,2-trifluoro-ethyl)-propionamide HCl salt (1.03 g, 5.00 mmol) and diisopropylethylamine (1.94 g, 2.61 mL, 15.0 mmol). The mixture was stirred overnight, diluted with ethyl acetate, washed with brine, dried over magnesium sulfate, and concentrated. The residue was purified by silica gel chromatography (25-35% ethyl acetate in hexanes) to give 2-(4,6-dichloro-pyrimidin-2-ylamino)-N-(2,2,2-trifluoro-ethyl)-propionamide (compound 1019, 670 mg, 42% yield) and 2-(2,6-dichloro-pyrimidin-4-ylamino)-N-(2,2,2- trifluoro-ethyl)-propionamide (compound 1020, 760 mg, 48% yield), both as white solids.

Example 23

Preparation of (S)-2-(4-(pyrrolidin-1-yl)-6-(7H-pyrrolo[2,3-d]pyrimidin-5-yl)pyrimidin-2-ylamino)-N-(2,2,2-trifluoroethyl)propanamide (Compound 31)

As shown in FIG. 4—step v, to a solution of compound 1019 (31.7 mg, 0.100 mmol) in DME (0.50 mL) was added a nucleophilic amine (pyrrolidine, 10 μL, 0.11 mmol) and diisopropylethylamine (25.8 mg, 34.8 μL, 0.200 mmol). The mixture was heated at 160° C. with microwave for 5 min, followed by the addition of 5-(4,4,5,5-tetramethyl-[1,3,2]dioxaborolan-2-yl)-7H-pyrrolo[2,3-d]pyrimidine (compound 1005, 39.9 mg, 0.100 mmol) and a solution of CsF (30 mg, 0.20 mmol) in water (0.25 mL). The mixture was heated at 160° C. with microwave for 5 min. The reaction mixture was filtered through a short pad of silica gel using EtOAc/hexanes as eluent to provide, after concentration in vacuo, the crude intermediate tosylate. This intermediate was dissolved in 1 mL of dry methanol and 200 uL of 25% sodium methoxide in methanol was added. The reaction mixture was stirred at 60° C. for 1 hour and quenched with trifluoroacetic acid. Purification by reversed-phase HPLC gave 35.0 mg of 2-[4-pyrrolidin-1-yl-6-(7H-pyrrolo[2,3-d]pyrimidin-5-yl)-pyrimidin-2-ylamino]-N-(2,2,2-trifluoro-ethyl)-propionamide TFA salt (a compound of formula IX where $R^{10}$ is 1-pyrrolidine).

Example 24

Preparation of (S)-2-(6-(pyrrolidin-1-yl)-2-(7H-pyrrolo[2,3-d]pyrimidin-5-yl)pyrimidin-4-ylamino)-N-(2,2,2-trifluoroethyl)propanamide (Compound 32)

As shown in FIG. 4—step vi, the title compound was prepared according to the procedure of Example 23 using compound 1020 as the starting material to provide the title compound (a compound of formula X, where $R^{10}$ is 1-pyrrolidine).

Example 25

Preparation of (S)-2-(4-(pyrrolidin-1-yl)-6-(7H-pyrrolo[2,3-d]pyrimidin-5-yl)-1,3,5-triazin-2-ylamino)-N-(2,2,2-trifluoroethyl)propanamide (Compound 33)

Figure 5:
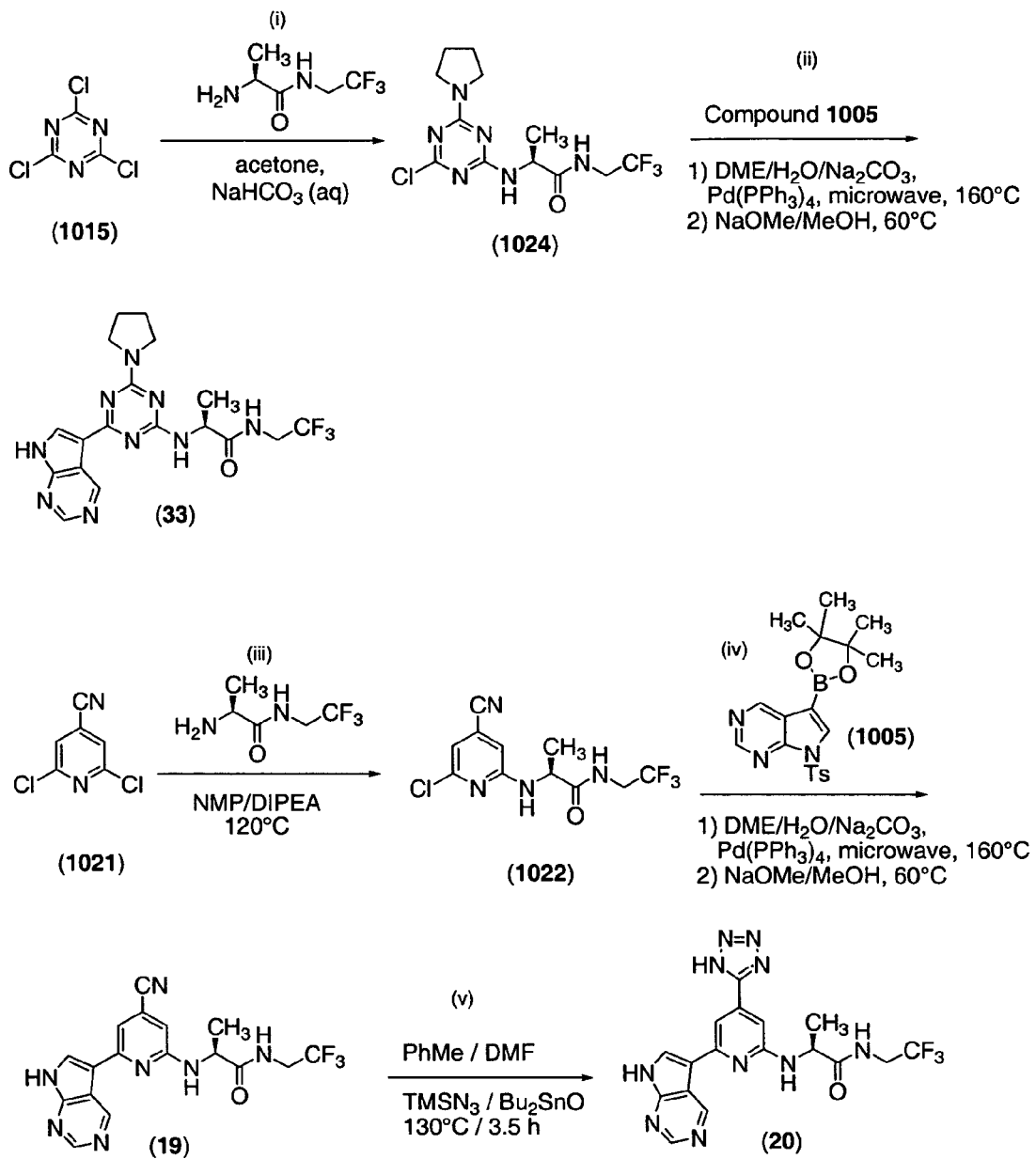
FIG. 5 is a scheme showing the syntheses of compounds 33 and 20 from cyanuric chloride and 4-cyano-2,6-dichloropyridine, respectively.

As shown in FIG. 5—step i, to a mixture of 2-amino-N-(2,2,2-trifluoro-ethyl)-propionamide HCl salt (103 mg, 1.00 mmol), acetone (1.0 mL), and aqueous sodium bicarbonate (1.0 mL) was cooled to 0° C. and cyanuric chloride (compound 1015) (184 mg, 1.00 mmol) was added. The mixture was stirred for 0.5 hours and extracted with ethyl acetate. The organic phase was dried over magnesium sulfate and concentrated. The residue was purified by silica gel chromatography (0-45% ethyl acetate in hexanes) to produce 2-(4,6-dichloro-[1,3,5]triazin-2-ylamino)-N-(2,2,2-trifluoroethyl)-propionamide (compound 1024, 154 mg, 97% yield) as a white solid.

Using the procedure of Example 23, compound 1024 was sequentially reacted with pyrrolidine and compound 1005 to produce compound 33.

Example 26

Preparation of (S)-2-(6-morpholino-2-(7H-pyrrolo[2,3-d]pyrimidin-5-yl)pyrimidin-4-ylamino)-N-(2,2,2-trifluoroethyl)propanamide (Compound 36)

The title compound was prepared according to the procedure of Example 23 by sequentially reacting compound 1024 with morpholine and compound 1005.

Example 27

Preparation of (S)-2-(4-morpholino-6-(7H-pyrrolo[2,3-d]pyrimidin-5-yl)-1,3,5-triazin-2-ylamino)-N-(2,2,2-trifluoroethyl)propanamide (Compound 37)

The title compound was prepared according to the procedure of Example 24 by sequentially reacting compound 1020 with morpholine and compound 1005.

Example 28

Preparation of (S)-2-(4-cyano-6-(7H-pyrrolo[2,3-d]pyrimidin-5-yl)pyridin-2-ylamino)-N-(2,2,2-trifluoroethyl)propanamide (Compound 19)

As shown in FIG. 5—step iii, 4-cyano-2,6-dichloropyridine (compound 1021) (346 mg, 2.0 mmol), (S)-2-amino-N-(2,2,2-trifluoroethyl)propanamide (761 mg, 2.1 mmol), 2 mL of DIEA, and 1 mL of NMP was placed in a sealed tube. The reaction mixture was stirred at 120° C. for 2 hours and concentrated to dryness. The residue was dissolved in DCM and washed with saturated aqueous $NaHCO_3$ solution. The organics were dried ($Na_2SO_4$) and concentrated in vacuo to give a residue that was purified by silica gel chromatography (50% EtOAc/50% hexanes) to provide 135 mg of compound 1022 (60% yield). As shown in FIG. 5—step iv, compound 1022 (31 mg, 0.1 mmol), compound 1005 (52 mg, 0.12 mmol), $Pd(Ph_3P)_4$ (6.4 mg), and $Na_2CO_3$ 2M (150 uL) in DME was heated at 160° C. for 15 minutes under microwave irradiation. The reaction mixture was filtered through a short pad of silica gel using EtOAc/hexanes as the eluent to provide, after concentration in vacuo, the crude intermediate tosylate. This intermediate was dissolved in 1 mL of dry methanol and 200 uL of 25% sodium methoxide in methanol was added. The reaction mixture was stirred at 60° C. for 1 hour and quenched with 6N HCl (154 uL). The volatiles were removed in vacuo and the product purified by silica gel chromatography (20% EtOAc/hexane, 100% EtOAc, and 5% MeOH/DCM) to provide 9 mg (19% yield) of compound 19.

Example 29

Preparation of (S)-2-(6-(7H-pyrrolo[2,3-d]pyrimidin-5-yl)-4-(1H-tetrazol-5-yl)pyridin-2-ylamino)-N-(2,2,2-trifluoroethyl)propanamide (Compound 20)

As shown in FIG. 5—step v, to a solution of(S)-2-(4-cyano-6-(7H-pyrrolo[2,3-d]pyrimidin-5-yl)pyridin-2-ylamino)-N-(2,2,2-trifluoroethyl)propanamide (compound 19, 4.5 mg, 0.012 mmol) in 1 mL of toluene was added azidotrimethylsilane (150 uL) and dibutyltin oxide (10 mg). The reaction flask was sealed and the reaction mixture heated for 3.5 hours at 130° C. The mixture was concentrated in vacuo followed by reversed-phase HPLC purification (0-70%

MeCN/water (0.1% TFA) gradient over 20 minutes) to provide compound 20 (2.8 mg, 44% yield).

Example 30

Preparation of Compounds of Formula XI

Figure 6:
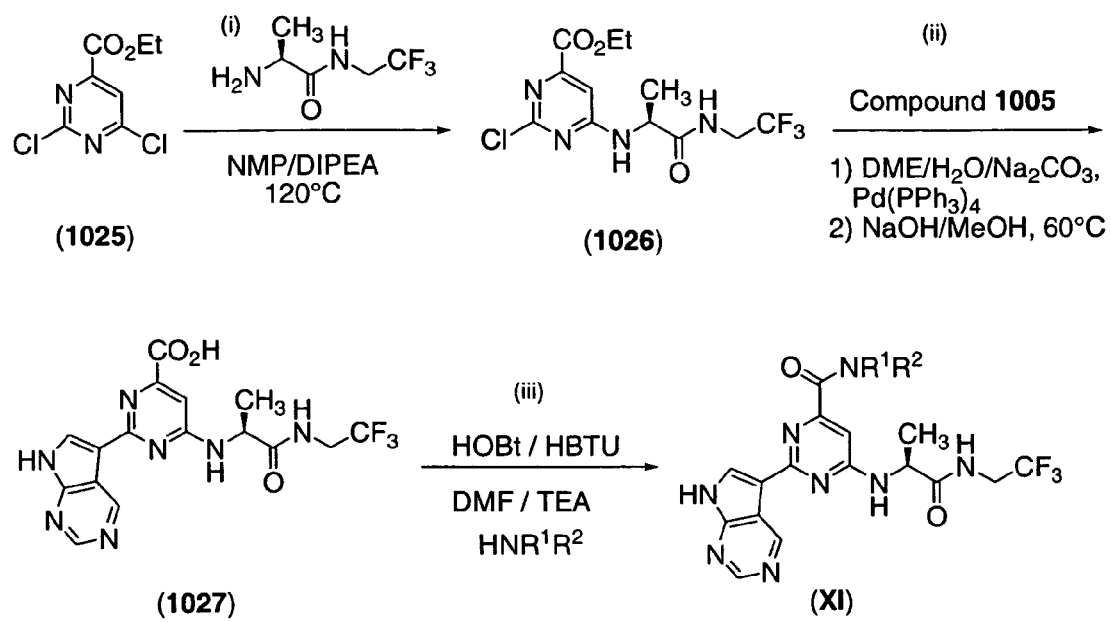
FIG. 6 is a scheme showing the synthesis of a compound of formula XI from compound 1025.

As shown in FIG. 6—step i, compound 1026 was prepared using the procedure of Example 28, with ethyl 2,6-dichloropyrimidine-4-carboxylate (compound 1025) instead of 4-cyano-2,6-dichloropyridine as the starting material. As shown in FIG. 6, step ii, compound 1005 and compound 1026 were reacted using the procedure of Example 28, followed by saponification of the ethyl ester with methanolic sodium hydroxide to provide 6-((S)-1-(2,2,2-trifluoroethylcarbamoyl)ethylamino)-2-(7H-pyrrolo[2,3-d]pyrimidin-5-yl)pyrimidine-4-carboxylic acid (compound 1027). A representative example for the preparation of compounds having formula XI is as follows. As shown in FIG. 6, step iii, to a solution of 6-((S)-1-(2,2,2-trifluoroethylcarbamoyl)ethylamino)-2-(7H-pyrrolo[2,3-d]pyrimidin-5-yl)pyrimidine-4-carboxylic acid (5 mg) in 1.0 mL DMF was added (S)-pyrrolidin-2-yl)methanol (1.5 mg), 1 drop of Et$_3$N, 4 mg of HBTU, 4 mg of HOBT. The reaction was stirred at room temperature for 2 hours. The reaction was diluted with 2 mL ethyl acetate and washed with water (2 mL×3). The organic layer was concentrated and purified by preparative reversed-phase HPLC to yield 3 mg (60% yield) of the compound of formula XI where NR$^1$R$^2$ is (S)-2-(hydroxymethyl)pyrrolidin-1-yl (compound 8).

Example 31

Preparation of 2-(7H-pyrrolo[2,3-d]pyrimidin-5-61)quinazolines

Compounds such as, for example, compound 38, can be prepared using the procedure of Example 1b (see FIG. 2), with 2,4-dichloroquinazoline as the starting material.

Example 32

Preparation of 3-(4-(6-(7H-pyrrolo[2,3-d]pyrimidin-5-yl)pyridin-2-yl)-5,6-dihydropyridin-1(2H)-yl)-3-oxopropanenitrile (Compound 30)

Figure 7:
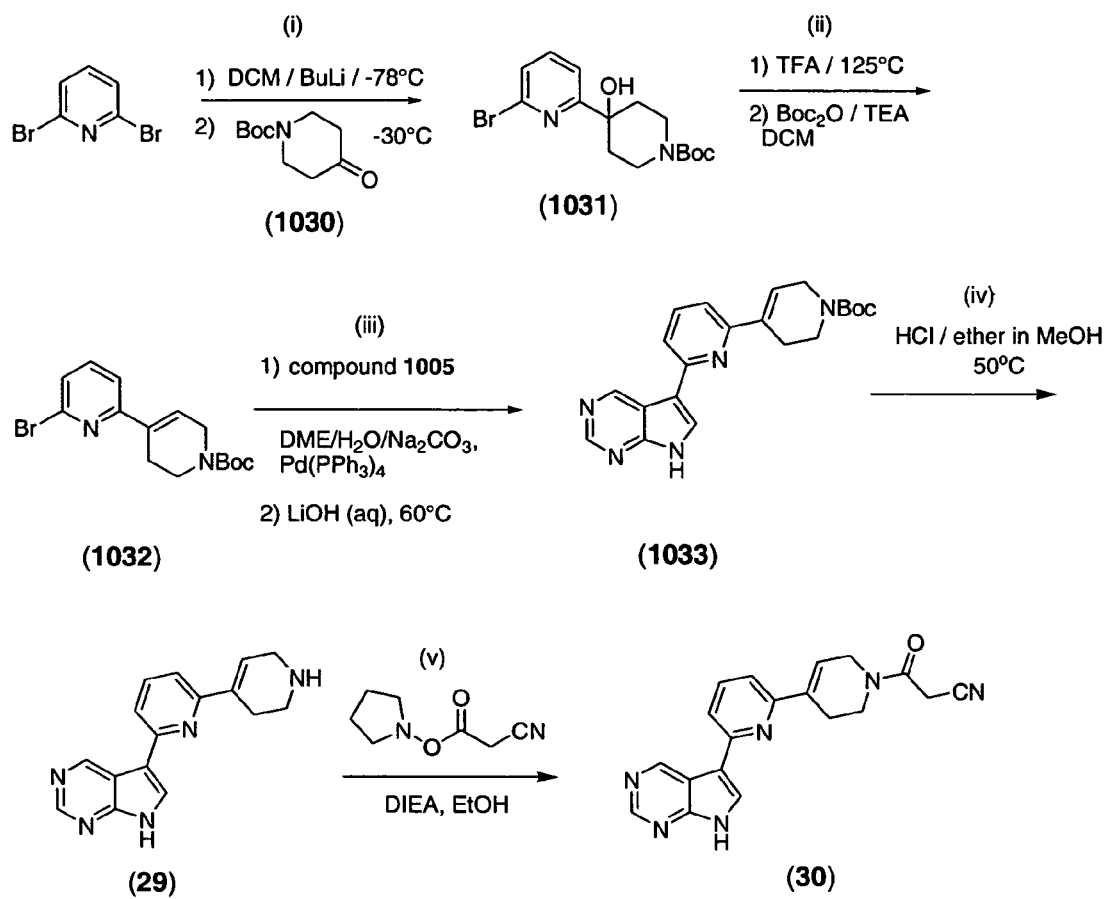
FIG. 7 is a scheme showing the syntheses of compounds 29 and 30 from 2,6-dibromopyridine.

As shown in FIG. 7—step i, to a solution of 2,6-dibromopyridine (4.738 g) in dichloromethane (80 mL) was added dropwise n-butyllithium (2.5 N, 8.9 mL) at or below −65° C., followed by stirring at this temperature for 20 min. 4-Oxopiperidine-1-carboxylic acid tert-butyl ester (compound 1030) (4.38 g) was added. After 15 min, the temperature was brought up to −30° C. and a saturated aqueous ammonium chloride solution (100 mL) was added. The organic and aqueous layers were separated, the aqueous layer extracted with dichloromethane (2×80 mL). The combined organics were evaporated to gave a residue which was triturated with hexane to give 6-bromo-4'-hydroxy-3',4',5',6'-tetrahydro-2'H-[2,4']bipyridinyl-1'-carboxylic acid tert-butyl ester (compound 1031) as a white solid (7.05 g).

As shown in FIG. 7—step ii, compound 1031 (2.0 g) was mixed with TFA (25 mL) in a sealed tube and heated at 128° C. for 2 days. Removal of the TFA gave a residue, which was dissolved in methanol (30 mL) and treated with triethylamine (2 mL) and di-tert-butyl dicarbonate (1.4 mL). After 1 hour, the volatiles were removed in vacuo and water (100 mL) was added. Extraction with dichloromethane (3×), concentration, and purification by chromatography (SiO$_2$, 20% ethyl acetate/hexane) gave 6-bromo-3',6'-dihydro-2'H-[2,4']bipyridinyl-1'-carboxylic acid, tert-butyl ester (compound 1032) (0.96 g).

As shown in FIG. 7—step iii, a mixture of compound 1032 (0.18 g), 5-(4,4,5,5-Tetramethyl-[1,3,2]dioxaborolan-2-yl)-7-(toluene-4-sulfonyl)-7H-pyrrolo[2,3-d]pyrimidine (compound 1005, 0.20 g), tetrakis(triphenylphosphine) palladium (50 mg), and 2N sodium carbonate (0.8 mL) in DME (5 mL) was heated at 90° C. overnight. Saturated aqueous lithium hydroxide (2 mL) was added and the reaction was heated at 60° C. for 1 hour. The reaction mixture was diluted with EtOAc and washed with brine. The organics were dried over sodium sulfate, concentrated, and purified by chromatography (SiO$_2$, 50% ethyl acetate/hexane) to afford 6-(7H-Pyrrolo[2,3-d]pyrimidin-5-yl)-3',6'-dihydro-2'H-[2,4']bipyridinyl-1'-carboxylic acid tert-butyl ester (compound 1033, 81.6 mg).

As shown in FIG. 7—step iv, a 2 NHCl-ether solution (3 mL) was added to compound 1033 (78 mg) in methanol (5 mL). The resulting mixture was heated at 50° C. for 40 min. Evaporation and trituration with ether gave 6-(7H-Pyrrolo[2,3-d]pyrimidin-5-yl)-1',2',3',6'-tetrahydro-[2,4']bipyridinyl hydrochloride (compound 29, 51 mg).

As shown in FIG. 7—step v, compound 29 (30 mg) and 2-cyano acetic acid, pyrrolidin-1-yl ester (47 mg) were mixed in ethanol (2 mL) and diisopropylethylamine (0.084 mL) was added. After stirring at rt for 12 hours, water (30 mL) was added. Extraction with dichloromethane (3×) and chromatographic purification (SiO$_2$, ethyl acetate) afforded 5.3 mg of 3-oxo-3-[6-(7H-pyrrolo[2,3-d]pyrimidin-5-yl)-3',6'-dihydro-2'H-[2,4']bipyridinyl-1'-yl]-propionitrile (compound 30).

Example 33

Preparation of (R)-2-(4-(7H-pyrrolo[2,3-d]pyrimidin-5-yl)-1,3,5-triazin-2-ylamino)-N-(2,2,2-trifluoroethyl)propanamide (Compound 78)

To a solution of 2,4-dichloro-1,3,5-triazine (298 mg, 2.0 mmol) in 4 mL THF and isopropanol(1:1 v:v) at −20° C. was added (R)-2-amino-N-(2,2,2-trifluoroethyl)propanamide (412 mg, 2.0 mmol, 1.0 equiv.), followed by the addition of N,N-isopropyl ethyl amine (516 mg, 4.0 mmol, 2.0 equiv.). The reaction was stirred at −20° C. for 20 minutes then was allowed to warm to room temperature. After 30 minutes, the reaction was poured into ethyl acetate and washed with water. The organic layer was concentrated. The oily residue was purified by chromatography (2:1 hexane/ethyl acetate) to produce 186 mg of (R)-2-(4-chloro-1,3,5-triazin-2-ylamino)-N-(2,2,2-trifluoroethyl)propanamide (compound 1034) (LC/MS: MS+1=284.1, MS−1=282.3, R.T.=1.5 min).

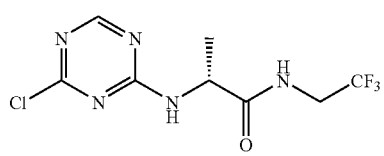

(1034)

(R)-2-(4-(7H-pyrrolo[2,3-d]pyrimidin-5-yl)-1,3,5-triazin-2-ylamino)-N-(2,2,2-trifluoroethyl)propanamide was prepared using the procedure of Example 1b and compounds 1034 and 1005 as starting materials.

Example 34

Preparation of (S)-2-(4-(7H-pyrrolo[2,3-d]pyrimidin-5-yl)-1,3,5-triazin-2-ylamino)-N-(2,2,2-trifluoroethyl)propanamide (Compound 79)

Using (S)-2-amino-N-(2,2,2-trifluoroethyl)propanamide as the starting material, (S)-2-(4-chloro-1,3,5-triazin-2-ylamino)-N-(2,2,2-trifluoroethyl)propanamide (compound 1035) was prepared by the same method as used in the preparation of compound 1034. (MS+1=284.1, MS−1=282.3).

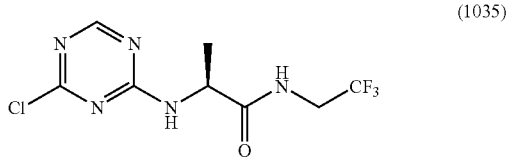 [SMILES: C[C@H](Nc1ncnc(Cl)n1)C(=O)NCC(F)(F)F]
(1035)

The title compound was prepared using the procedure of Example 1b with compounds 1035 and 1005 as starting materials.

Example 35

Preparation of 2-(2-(7H-pyrrolo[2,3-d]pyrimidin-5-yl)-9H-purin-9-yl)-N-(2,2,2-trifluoroethyl)-2-methylpropanamide (Compound 108)

Figure 8:
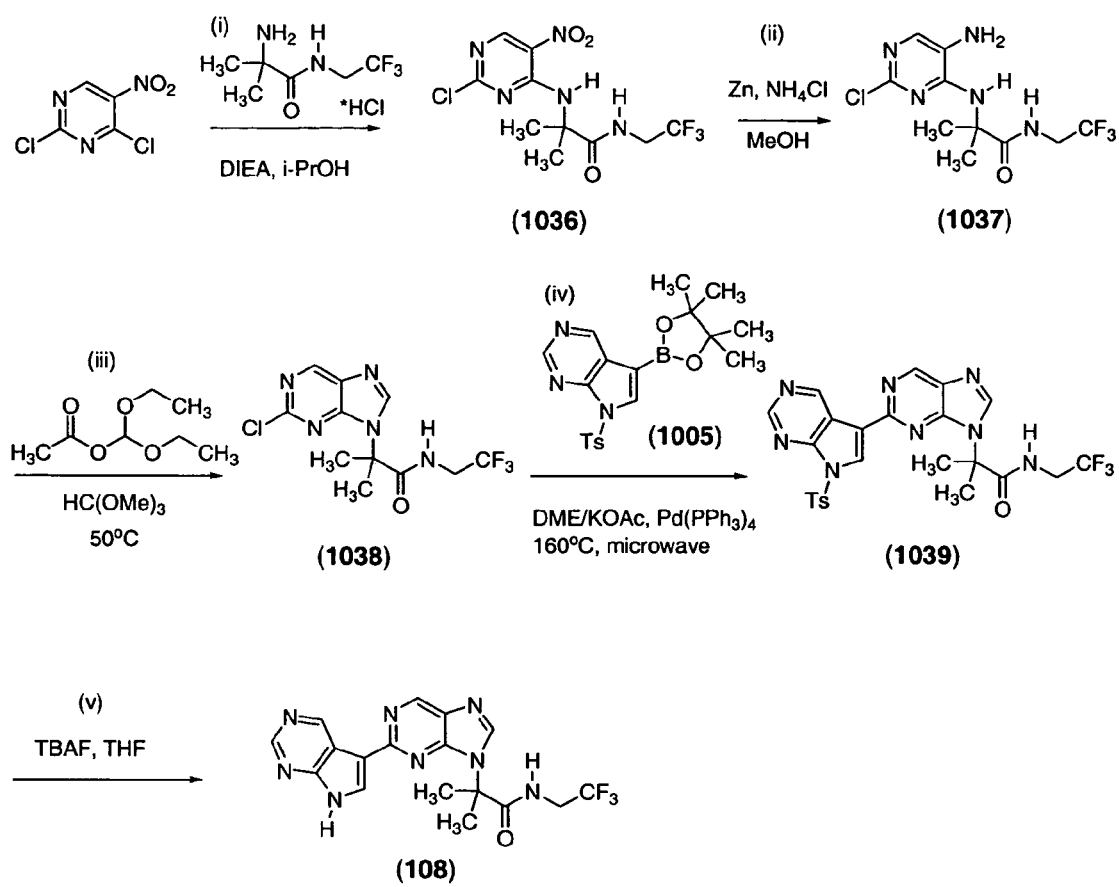
FIG. 8 is a scheme showing the synthesis of compound 108 from 5-nitro-2,4-dichloropyrimidine.

As shown in FIG. 8—step i, 5-nitro-2,4-dichloropyrimidine (500 mg, 2.58 mmol), 2-amino-N-(2,2,2-trifluoroethyl)-2-methylpropanamide hydrochloride (568 mg, 2.58 mmol), and diisopropylethylamine (1.3 mL, 7.5 mmol) were mixed together in isopropanol. After the resulting exotherm subsided, the mixture was concentrated and purified by silica gel chromatography (0-40% EtOAc/hexanes) to produce 409 mg of compound 1036 as an orange solid, ESMS (M+1)=341.9.

As shown in FIG. 8—step ii, compound 1036 (409 mg, 1.19 mmol) was dissolved in about 10 mL methanol and ammonium chloride (320 mg, 6 mmol) was added followed by the addition of Zinc dust (777 mg, 11.9 mmol). After the exotherm subsided, the reaction mixture was filtered through a pad of Celite™, which washed with methanol. Compound 1037 was recovered as a pale yellow solid after removal of the volatiles in vacuo, ESMS (M+1)=311.9.

As shown in FIG. 8—step iii, compound 1037 (115 mg, 0.49 mmol) was dissolved in 3 mL of methyl orthoformate and 1.5 ml of 4,4-diethoxybutan-2-one was added. The reaction mixture was microwaved for 20 minutes at 160° C. followed by removal of the volatiles in vacuo. The resulting crude product (compound 1038) was used as is in the next reaction.

As shown in FIG. 8—steps iv & v, compound 1038 (48 mg, 0.15 mmol), Pd(Ph$_3$P)$_4$ (17 mg, 0.015 mmol), and 1 mL of 2M of potassium acetate (aq) in 2 mL of DME were microwaved at 160° C. for 10 minutes. The crude mixture was diluted with EtOAc, washed with water, and dried over sodium sulfate. The volatiles were removed in vacuo and the resulting crude product purified by reversed-phase HPLC [CH$_3$CN/H$_2$O (0.1% TFA) gradient] to produce compound 1039 (15 mg, 0.026 mmol). Compound 1039 was subsequently treated with 0.32 mL of 1 M tetrabutylammonium fluoride (0.032 mmol) in 1 mL of THF at room temperature. After 1 hour, the volatiles were removed in vacuo and the product purified by reversed-phase HPLC (CH$_3$CN/H$_2$0 (0.1% TFA) gradient) to produce compound 108.

Example 36

Preparation of (R)-2-(2-(7H-pyrrolo[2,3-d]pyrimidin-5-yl)-7H-pyrrolo[2,3-d]pyrimidin-7-yl)-N-(2,2,2-trifluoroethyl)-3-methylbutanamide (Compound 110)

Figure 9:
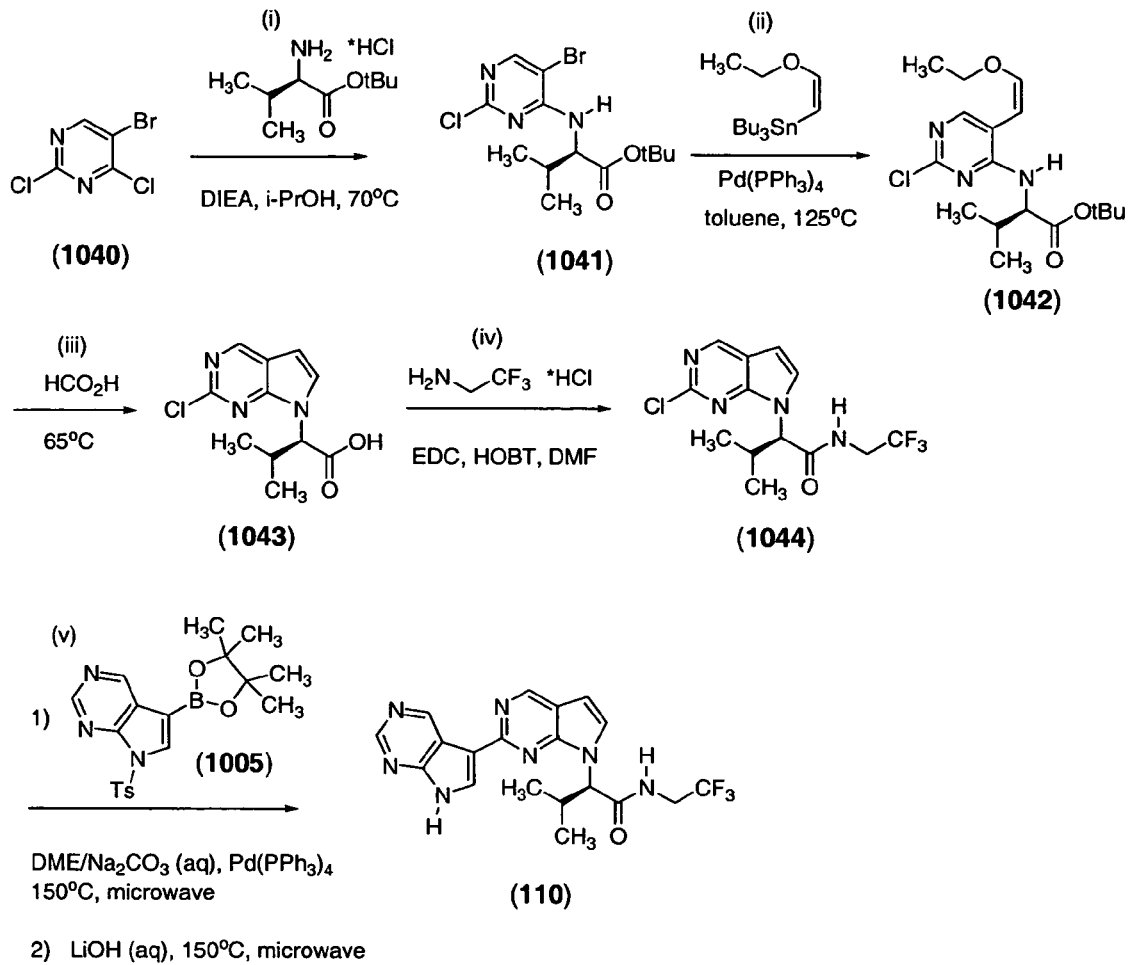
FIG. 9 is a scheme showing the synthesis of compound 110 from 5-bromo-2,4-dichloropyrimidine.

As shown in FIG. 9—step i, 5-bromo-2,4,dichloropyrimidine (compound 1040, 460 mg, 2.0 mmol) in about 20 mL of isopropanol was treated with D-valine, t-butyl ester, hydrochloride (420 mg, 2.0 mmol) and DIEA (0.7 mL, 4 mmol). The reaction mixture was stirred at rt for 16 hours, concentrated in vacuo, and purified by silica gel chromatography (10% EtOAc/hexanes) to afford 720 mg of compound 1041, along with 15% of the regioisomeric (R)-tert-butyl 2-(5-bromo-4-chloropyrimidin-2-ylamino)-3-methylbutanoate, ESMS (M+H)=365.5.

As shown in FIG. 9—step ii, compound 1041 (720 mg, 1.97 mmol, as the 85:15 regioisomeric mixture), tributyl((Z)-2-ethoxyvinyl)stannane (1.42 g, 3.9 mmol), Pd(Ph$_3$P)$_4$ (225 mg, 0.195 mmol), and 10 mL of toluene were placed in a sealed tube under an atmosphere of nitrogen and heated at 125° C. for 20 hours. The reaction mixture was cooled and the volatiles removed in vacuo. Purification by silica gel chromatography (10-15% EtOAc/hexanes) gave 376 mg of compound 1042 as an oil, ESMS (M+H)=357.

As shown in FIG. 9—step iii, compound 1042 (376 mg, 1.06 mmol) was dissolved in neat formic acid and heated at 65° C. for 1 hour. The reaction mixture was concentrated in vacuo to yield compound 1043 (267 mg) as a tan powder.

As shown in FIG. 9—step iv, compound 1043 (143 mg, 0.56 mmol), 2,2,2-trifluoroethylamine hydrochloride (83 mg, 0.62 mmol), HOBT (83 mg, 0.62 mmol), EDC (119 mg, 0.62 mmol), and DIEA (0.22 mL, 1.2 mmol) were dissolved in about 5 mL of DMF. After stirring at rt for 20 hours, the reaction mixture was diluted with EtOAc (about 25 mL) and washed with water (3×), 0.5 M HCl (aq) (1×) and brine (1×). The organics were dried over sodium sulfate and the volatiles removed in vacuo to give crude product, which was treated with ethyl ether/hexanes (approximately 1:1), filtered, and concentrated in vacuo to give compound 1044 (187 mg) as a viscous oil.

As shown in FIG. 9—step v, compound 1044 (45 mg, 0.13 mmol) was combined with 5-(4,4,5,5-tetramethyl-[1,3,2]dioxaborolan-2-yl)-7-(toluene-4-sulfonyl)-7H-pyrrolo[2,3-d]pyrimidine (compound 1005, 47 mg, 0.12 mmol), Pd(PPh$_3$)$_4$ (25 mg, 0.02 mmol), and 1 mL of 2M Na$_2$CO$_3$ in 2 mL of DME. The mixture was heated at 150° C. under microwave irradiation for 10 minutes. At this time, aqueous 1 M lithium hydroxide solution (2 mL) was added to the reaction mixture and microwave irradiation was continued at 150° C. for 10 min. The mixture was cooled and water (20 mL) was added. Purification by reversed-phase HPLC gave 27 mg of compound 110 as a yellow powder.

Example 37

NMR and Mass Spectrometry

Analytical data for certain compounds of the present invention was collected and recorded as follows: Proton nuclear magnetic resonance (NMR) was collected using a Bruker AMX 500 instrument and appropriate solvent. The liquid chromatography mass spectrometry (LC/MS) method used a Hypersil BDS C18 5 micron 2.1×50 mm column with a flow rate of 1.0 mL/min with an appropriate gradient. Mass spectrometer samples were analyzed on a MicroMass ZQ or Quattro II mass spectrometer operated in single MS mode with electrospray ionization. Samples were introduced into the mass spectrometer using flow injection (FIA) or chromatography. Mobile phase for mass spectrometer analysis consisted of acetonitrile-water mixtures or trifluoroacetic acid (TFA) in some instances. Table 2 below depicts exemplary mass spectral data (ESMS) and $^1$H-NMR data (NMR) for certain compounds of the invention, where the compound numbers in Table 2 correspond to the compounds depicted in Table 1:

TABLE 2

| Compound No. | ESMS (M+H) | $^1$H NMR<br>NMR peaks given as δ values |
|---|---|---|
| 1 | 351.20 | DMSO-d$_6$: 12.8(bs, 1H); 9.7(s, 1H); 9.0(s, 1H); 8.4(s, 1H); 7.7(dd, 1H); 7.2(d, 1H); 6.8(d, 1H); 4.3(bd, 4H); 3.1(bd, 2H); 2.1(s, 3H); 1.2(bs, 6H) |
| 2 | 438.00 | DMSO-d$_6$: 9.72(s, 1H); 8.90(s, 1H); 8.80(m, 1H); 8.32(s, 1H); 8.05(m, 1H); 7.10(m, 1H); 4.68(m, 1H); 4.35(q, H); 3.90(m, 2H); 1.42(d, 3H); 1.40(t, 3H) |
| 3 | 409.90 | DMSO-d$_6$: 9.70(s, 1H); 8.98(s, 1H); 8.80(m, 1H); 8.42(s, 1H); 8.12(m, 1H); 7.10(m, 1H); 4.68(m, 1H); 3.85(m, 2H); 1.34(d, 2H) |
| 4 | 365.00 | DMSO-d$_6$: 13.2(br s, 1H); 9.7(s, 1H); 9.0(s, 1H); 8.5(dd, 1H); 8.4(s, 1H); 7.4(dd, 1H); 7.15(d, 1H); 6.45(d, 1H); 4.4(m, 1H); 3.8-3.7(m, 2H); 1.35(d, 3H) |
| 5 | 366.00 | DMSO-d$_6$: 13.2(br s, 1H); 9.55(s, 1H); 9.25(br s, 1H); 9.05(m, 1H); 8.9(s, 1H); 8.6(s, 1H); 8.15(d, 1H); 6.7(d, 1H); 4.8(m, 1H); 3.9(m, 2H); 1.4(d, 3H) |
| 6 | 384.00 | DMSO-d$_6$: 13.2(br s, 1H); 9.6(s, 1H); 9.0(s, 1H); 8.7(dd, 1H); 8.3(s, 1H); 8.25(s, 1H); 7.9(d, 1H); 4.6(m, 1H); 3.9-3.7(m, 2H); 1.4(d, 3H) |
| 7 | 491.00 | DMSO-d$_6$: 9.60(s, 1H); 9.00(s, 1H); 8.82(m, 1H); 8.35(m, 1H); 8.00(m, 1H); 6.50(s, 1H); 4.66(m, 1H); 4.50(m, 1H); 3.90(m, 2H); 3.75 9m, 1H); 3.05(m, 1H); 2.85 9m, 1H); 1.78(m, 3H); 1.46(d, 3H); 1.12(m, 2H); 0.90(d, 3H) |
| 8 | | DMSO-d$_6$: 9.60(s, 1H); 9.00(s, 1H); 8.82(m, 1H); 8.45(m, 1H); 8.00(m, 1H); 6.66(s, 1H); 4.60(m, 1H); 4.45(m, 1H); 4.10(m, 1H); 3.90(m, 2H); 3.70-3.20(m, 4H); 1.80(m, 4H); 1.40(d, 3H) |
| 9 | 462.90 | |
| 10 | 451.20 | methanol-d$_4$: d 1.55(d, 3H), 2.08-2.39(m, 2H), 3.71-4.12(m, 7H), 4.41-4.50(m, 1H), 5.57-5.70(m, 1H), 6.66-6.73(m, 1H), 8.59(s, 1H), 9.11(s, 1H), 9.96(s, br., 1H) |
| 11 | 507.00 | |
| 12 | 478.90 | |
| 13 | 492.90 | DMSO-d$_6$: 9.60(s, 1H); 8.96(s, 1H); 8.80(m, 1H); 8.40(s, 1H); 8.00(m, 1H); 6.50(s, 1H); 4.70(m, 1H); 4.10-3.60(m, 5H); 3.25(m, 2H); 1.80(m, 2H); 1.38(d, 3H) |
| 14 | 466.90 | DMSO-d$_6$: 9.70(s, 1H); 8.92(s, 1H); 8.75 9m, 2H); 8.60(s, 1H); 8.02(s, 1H); 7.02(s, 1H); 4.70(m, 1H); 4.00-3.60(m, 10H); 1.42 9d, 3H) |
| 15 | 466.90 | DMSO-d$_6$: 9.58(s, 1H); 8.98(s, 1H); 8.80(m, 1H); 8.35(m, 1h); 8.00(m, 1H); 6.55(m, 1H); 4.70(m, 1H); 3.90(m, 3H); 3.60(m, 5H); 3.00(s, 3H); 1.41(d, 3H) |
| 16 | 479.00 | DMSO-d$_6$: 9.70 s, 1H); 8.92(s, 1H); 8.75(m, 2H); 8.32(m, 1H); 8.03(m, 1H); 7.05 9s, 1H); 4.70(m, 1H); 4.00-3.70(m, 4H); 1.85(m, 1H); 1.38(d, 3H); 1.20(d, 3h); 0.88(m, 6H) |
| 17 | 513.00 | |
| 18 | 442.10 | methanol-d$_4$: 9.86 & 8.65(2s, 1H), 9.27(s, 1H), 9.06(s, 1H), 9.03(s, 1H), 8.07(m, 1H), 7.88(d, 1H), 7.56(m, 2H), 7.01(d, 1H), 4.66(m, 1H), 3.98-3.84(m, 2H), 1.60(d, 3H) |
| 19 | 390.00 | DMSO-d$_6$: 12.5(s, 1H), 9.64(s, 1H); 8.80(s, 1H); 8.78(m, iH), 8.32(s, 1H), 7.55-7.62(m, 1H), 7.48(s, 1H), 7.34(d, 1H), 6.71(s, 1H), 4.49(m, 1H), 3.8-3.98(m, 2H), 1.41(d, 3H) |
| 20 | 433.00 | DMSO-d$_6$: 13.0(s, 1H), 9.75(s, 1H); 9.00(s, 1H), 8.66(t, 1H), 8.42(s, 1H), 7.69(s, 1H), 7.37(s, 1H), 7.15(s, 1H), 4.56(m, 1H), 3.88(m, 2H), 1.45(d, 3H) |
| 21 | 315.20 | DMSO-d$_6$: 13.05(br s, 1H); 9.65(s, 1H); 9.0(s, 1H); 8.4(s, 1H); 8.3(d, 1H); 4.45(m, 1H); 3.85(m, 1H); 3.75(m, 1H); 3.65(m, 1H); 3.45(m, 1H); 2.1-1.9(m, 4H) |
| 22 | 315.20 | DMSO-d$_6$: 13.05(br s, 1H); 9.65(s, 1H); 9.0(s, 1H); 8.4(s, 1H); 8.3(d, 1H); 4.45(m, 1H); 3.85(m, 1H); 3.75(m, 1H); 3.65(m, 1H); 3.45(m, 1H); 2.1-1.9(m, 4H) |
| 23 | 329.20 | DMSO-d$_6$: 13.0(br s, 1H); 9.6(s, 1H); 9.0(s, 1H); 8.3(s, 1H); 8.25(d, 1H); 4.55(m, 1H); 3.85(m, 1H); 3.7(m, 1H); 3.6(m, 1H); 3.4(m, 1H); 3.3(s, 3H); 2.1-1.95(m, 4H) |
| 24 | 285.20 | DMSO-d$_6$: 12.95(br s, 1H); 9.65(s, 1H); 9.0(s, 1H); 8.4(s, 1H); 8.3(d, 1H); 3.8(m, 4H); 2.0(m, 2H) |
| 25 | 285.20 | methanol-d$_4$: 9.8(s, 1H); 9.1(s, 1H); 8.5(s, 1H); 8.2(d, 1H); 4.7(m, 1H); 4.0(m, 1H); 3.75(m, 1H); 3.7(m, 1H); 3.5(m, 1H); 3.4(s, 3H); 2.25-2.05(m, 4H) |

TABLE 2-continued

| Compound No. | ESMS (M+H) | ¹H NMR NMR peaks given as δ values |
|---|---|---|
| 26 | 409.90 | DMSO-$d_6$: 13.05(br s, 1H); 9.6(s, 1H); 9.0(s, 1H); 8.75(m, 1H); 8.3(m, 2H); 4.8(d, 1H); 4.05-3.8(m, 4H); 2.3(m, 1); 2.05-1.9(m, 3H) |
| 27 | 410.00 | DMSO-$d_6$: 13.05(br s, 1H); 9.6(s, 1H); 9.0(s, 1H); 8.75(m, 1H); 8.3(m, 2H); 4.8(d, 1H); 4.05-3.8(m, 4H); 2.3(m, 1); 2.05-1.9(m, 3H) |
| 28 | 378.10 | CDCl$_3$: 11.42(br s, 1H), 9.89(s, 1H); 9.01(s, 1H), 7.93(s, 1H), 7.71-7.27(m, 3H), 6.75(br s, 1H), 4.20(br s, 2H), 3.77(br s, 2H), 2.78(m, 2H), 1.52(s, 9H) |
| 29 | 278.20 | methanol-$d_4$: 9.95(s, 1H), 9.18(s, 1H), 8.65(s, 1H), 7.92(d, 1H), 7.91(dd, 1H), 7.61(d, 1H), 6.83(br s, 2H), 3.99(br s, 2H), 3.58(dd, 2H), 3.10(m, 2H) |
| 30 | 345.20 | methanol-$d_4$: 9.80, 9.76(2s, 1H), 8.84, 8.80(2s, 1H), 8.15, 8.14(2s, 1H), 7.78-7.69(m, 2H), 7.44, 7.41(2d, 1H), 6.75(br s, 1H), 4.33, 4.27(br s, 2H), 4.02, 3.95(2s, 2H), 3.90, 3.76(2dd, 2H), 2.94, 2.83(2m, 2H) |
| 31 | 435.10 | methanol-$d_4$: 1.55(d, 3H), 1.99-2.18(m, 4H), 3.66-3.76(m, 4H), 3.91-4.01(m, 2H), 4.60(q, 1H), 6.49(s, 1H), 8.31(s, 1H), 8.95(s, 1H), 9.41(s, 1H) |
| 32 | 435.10 | methanol-$d_4$: 1.53(d, 3H), 2.04-2.14(m, 4H), 3.65-3.73(m, 4H), 3.95(q, 2H), 4.64(q, 1H), 6.50(s, 1H), 8.39(s, 1H), 9.04(s, 1H), 9.40(s, 1H) |
| 33 | 436.10 | methanol-$d_4$: 1.53(d, 3H), 2.01-2.12(m, 4H), 3.55-3.88(m, 4H), 3.90-4.01(m, 2H), 4.56-4.63(m, 1H), 8.68(s, 1H), 9.05(s, 1H), 9.77(s, 1H) |
| 34 | 416.00 | DMSO-$d_6$: 9.75(m, 1H); 9.00(m, 2H); 8.65(m, 2H); 7.95(m, 1H); 7.82(m, 1H); 7.70(m, 1H); 5.08(m, 1H); 3.95(m, 2H); 1.55(d, 3H) |
| 35 | 451.10 | methanol-$d_4$: 1.34-1.39(m, 4H), 1.65(d, 3H), 3.64-4.01(m, 6H), 4.57(q, 1H), 7.85(s, 1H), 8.74(s, 2H), 9.10(s, 2H) |
| 36 | 451.10 | major tautomer (76%), methanol-$d_4$: 1.52(d, 3H), 3.64-3.99(m, 10H), 4.56(q, 1H), 6.54(s, 1H), 8.38(s, 1H), 8.99(s, 1H), 9.42(s, 1H), 9.91(s, 1H) |
| 37 | 452.10 | major tautomer (68%), methanol-$d_4$: .50(d, 3H), 3.67-3.99(m, 10H), 4.44-4.57(m, 1H), 8.57(s, 1H), 9.02(s, 1H), 9.82(s, 1H) |
| 38 | 416.00 | DMSO-$d_6$: 9.70(s, 1H); 9.00(m, 2H); 8.78(m, 1H); 8.66(d, 1H); 8.03(m, 1H); 7.92(d, 1H); 7.76(m, 1H); 5.06(m, 1H); 3.95(m, 2H) |
| 39 | 366.00 | DMSO-$d_6$: 9.62(s, 1H); 9.30(bs, 1H); 9.05(bs, 1H); 9.00(s, 1H); 8.64(s, 1H); 8.22(d, 1H); 6.78(m, 1H); 4.92(m, 1H); 3.95(m, 2H); 1.42(d, 3H) |
| 40 | 384.00 | DMSO-$d_6$: 9.65(s, 1H); 8.96(s, 1H); 8.76(dd, 1H); 8.35(s, 1H); 8.30(d, 1H); 7.92(d, 1H); 4.63(m, 1H); 3.88 m, 2H) |
| 41 | 398.00 | DMSO-$d_6$: 9.56(s, 1H); 9.00(s, 1H); 8.80(dd, 1H); 8.38(s, 1H); 8.28(d, 1H); 7.80(m, 1H); 4.52(m, 1H); 3.90(m, 2H); 1.90(q, 2H); 1.00(t, 3H) |
| 42 | 414.10 | methanol-$d_4$: 3.43(s, 3H), 3.77-4.01(m, 4H), 4.83(t, 1H), 8.25(d, 1H), 8.49(s, 1H), 9.11(d, 1H), 9.79(d, 1H) |
| 43 | 384.10 | DMSO-$d_6$: 13.0(s, 1H), 9.55(s, 1H), 8.95(s, 1H), 8.35(s, 1H), 8.3(s, 1H), 8.2(q, 1H), 8.1(d, (1H), 5.05(t, 1H), 2.9(m, 2H), 2.6(s, 3H) |
| 44 | 398.10 | DMSO-$d_6$: 13.0(s, 1H), 9.6(s, 1H), 8.95(s, 1H), 8.35(s, 1H), 8.3(s, 2H), 8.05(d, 1H), 5.0(m, 1H), 2.85-3.2(m, 4H), 1.0(t, 3H) |
| 45 | 452.10 | DMSO-$d_6$: 13.0(s, 1H), 9.6(s, 2H), 8.95(s, 1H), 8.35(s, 1H), 8.3(s, 1H), 8.15(d, 1H), 5.1(q, 1H), 3.9(m, 2H), 3.0(m, 2H) |
| 46 | 410.00 | DMSO-$d_6$: 9.70(s, 1H); 9.10(m, 1H); 8.88(m, 2H); 8.66(m, 1H); 8.40(m, 1H); 7.38(m, 1H); 5.00(m, 1H); 3.90(m, 2H); 1.50(d, 3H) |
| 47 | 446.20 | methanol-$d_4$: 3.48(s, 3H), 3.83-4.08(m, 4H), 5.37(t, 1H), 7.78(dd, 1H), 7.90(d, 1H), 8.07(dd, 1H), 8.55(d, 1H), 8.79(s, 1H), 9.04(s, 1H), 9.76(s, 1H) |
| 48 | 396.10 | methanol-$d_4$: 3.42(s, 3H), 3.75-4.00(m, 4H), 4.98(s, br., 1H), 7.30(s, br., 1H), 8.38(s, 1H), 8.67(d, 1H), 9.01(s, 1H), 9.52(d, 1H) |
| 49 | 230.90 | methanol-$d_4$: 10.07(s, 1H), 9.32(s, 1H), 8.96(s, 1H), 8.50(d, 1H) |
| 50 | 399.90 | methanol-$d_4$: 9.86(s, 1H), 9.29(s, 1H), 8.93(s, 1H), 8.53(d, 1H), 5.03(dd, 1H), 4.11(ddd, 2H), 3.99-3.82(m, 2H) |
| 51 | 382.10 | methanol-$d_4$: 8.82(s, 1H), 8.31(s, 1H), 8.27(d, 1H), 7.71(d, 1H), 7.23(d, 1H), 4.67(dd, 1H), 3.99(d, 2H), 3.93-3.82(m, 2H) |
| 52 | 428.40 | DMSO-$d_6$: 13.5(br s, 1H); 9.6(s, 1H); 9.0(s, 1H); 8.65(dd, 1H); 8.35(m, 2H); 5.45(d, 1H); 4.9(m, 1H); 4.35-4.05(m, 2H); 3.9(m, 2H); 2.4(m, 1H); 2.05(s, 1H) |

TABLE 2-continued

| Compound No. | ESMS (M+H) | ¹H NMR NMR peaks given as δ values |
|---|---|---|
| 53 | 428.40 | DMSO-d$_6$: 12.8(br s, 1H); 9.6(s, 1H); 8.9(m, 2H); 8.35(m, 1H); 8.2(m, 1H); 5.5(d, 1H); 4.9(m, 1H); 4.4-3.8(m, 4H); 2.2-2.0(m, 2H) |
| 54 | 406.20 | methanol-d$_4$: 1.51-2.09(m, 6H), 2.39-2.46(m, 1H), 3.50-3.60(m, 1H), 3.86-4.06(m, 2H), 7.01-7.09(m, 1H), 8.25(d, 1H), 8.56(s, 1H), 9.02(s, 1H), 9.57(s, 1H) |
| 55 | 378.20 | methanol-d$_4$: 2.46-2.54(m, 1H), 2.77-2.86(m, 1H), 3.85-4.37(m, 4H), 5.05-5.11(m, 1H), 7.21(d, 1H), 7.42(d, 1H), 7.70(d, 1H), 8.36(d, 1H), 8.78(s, 1H), 9.11(s, 1H), 9.67(s, 1H) |
| 56 | 398.10 | DMSO-d$_6$: 13.09(s, 1H), 9.62(s, 1H), 9.01(s, 1H), 8.46(t, J = 6.2 Hz, 1H), 8.29(d, J = 3.8 Hz, 1H), 8.23(s, 1H), 7.66(s, 1H), 3.75(m, 2H), 1.58(s, 6H) |
| 57 | 396.10 | DMSO-d$_6$: 13.04(s, 1H), 9.54(s, 1H), 8.99(s, 1H), 8.61(t, J = 6.3 Hz, 1H), 8.40(s, 1H), 8.30(s, 1H), 8.29(s, 1H), 3.80(m, 2H), 1.55(t, 1.55 Hz, 2H), 1.17(t, 1.17 Hz, 2H) |
| 58 | 353.00 | DMSO-d$_6$: 13.1(br m, 1H), 9.53(s, 1H), 9.0(s, 1H), 8.37(s, 1H), 8.33(d, 1H), 8.25(d, 1H), 7.55(dd, 2H), 7.15(t, 2H), 5.5(setp, 1H), 1.57(d, 6H) |
| 59 | 353.00 | DMSO-d$_6$: 13.1(br m, 1H), 9.53(s, 1H), 9.0(s, 1H), 8.37(s, 1H), 8.33(d, 1H), 8.25(d, 1H), 7.55(dd, 2H), 7.15(t, 2H), 5.5(setp, 1H), 1.57(d, 6H) |
| 60 | 408.10 | methanol-d$_4$: 3.61-3.77(m, 3H), 3.86-4.03(m, 4H), 4.17-4.22(m, 1H), 4.34-4.37(m, 1H), 7.01(d, 1H), 8.25(d, 1H), 8.60(s, 1H), 9.03(s, 1H), 9.73(s, 1H) |
| 61 | 406.20 | methanol-d$_4$: 1.55-2.09(m, 5H), 2.39-2.46(m, 1H), 3.52-3.61(m, 1H), 3.86-4.06(m, 2H), 7.06(s, br., 1H), 8.25(s, 1H), 8.59(s, 1H), 9.03(s, 1H), 9.58(s, 1H) |
| 62 | 438.10 | DMSO-d$_6$: 13.13(s, 1H), 9.63(s, 1H), 9.03(s, 1H), 8.36(t, J = 6.3 Hz, 1H), 8.31(d, J = 3.8 Hz, 1H), 8.25(s, 1H), 7.08(s, 1H), 3.82-3.74(m, 2H), 2.50(qn, J = 1.8 Hz, DMSO-d6), 2.2(d, 2H), 2.01-1.97(m, 2H), 1.59(d, J = 4.3 Hz, 2H), 1.54(d, J = 9.8 Hz, 2H), 1.35(d, J = 9.4 Hz, 1H), 1.25(d, J = 12.8 Hz, 1H) |
| 63 | 380.10 | methanol-d$_4$: 9.78(s, 1H), 9.06(s, 1H), 8.63(s, 1H), 8.16(d, J = 6.9 Hz, 1H), 6.73(d, J = 6.3 Hz, 1H), 3.82(m, 2H), 1.72(s, 6H) |
| 64 | 392.10 | methanol-d$_4$: 9.76(s, 1H), 9.04(s, 1H), 8.56(s, 1H), 8.18(d, J = 6.9 Hz, 1H), 7.70(d, J = 8.2 Hz, 1H, Ar-p-TsOH), 7.22(d, J = 7.9 Hz, 1H, Ar-p-TSsOH), 6.75(d, J = 6.7 Hz, 1H), 3.85-3.82(m, 2H), 2.95(m, 2H), 2.37(m and s, 4.5H, CH3-TsOH and CH2 cyclobutyl), 2.15-2.12(m, 2H) |
| 65 | 426.50 | CD$_3$CN: 11.58(s, 1H), 9.80(s, 1H), 9.11(s, 1H), 8.49(s, 1H), 8.28(d, 1H), 7.34(m, 1H), 6.28(s, 1H), 4.2-4.6(s, 16H), 3.91(m, 1H), 3.69(m, 1H), 2.28(m, 1H), 1.64(s, 3H), 1.08(dd, 6H) |
| 66 | 426.50 | CD$_3$CN: 11.54(s, 1H), 9.78(s, 1H), 9.06(s, 1H), 8.52(s, 1H), 8.24(d, 1H), 7.27(m, 1H), 4.81(d, 1H), 3.90(m, 2H), 3.4-3.7(s, 18), 3.25(d, 3H), 2.49(m, 1H), 1.00(dd, 6H) |
| 67 | 447.40 | CD$_3$CN: 11.4(s, 1H), 9.67(d, 1H), 9.03(d, 1H), 8.76(m, 1H), 8.53(dd, 1H), 8.45(s, 1H), 8.16(d, 1H), 8.03(dd, 1H), 7.49(dd, 1H), 7.13(m, 1H) 5.25(d, 2H), 4.17(m, 2H) |
| 68 | 394.20 | methanol-d$_4$: 9.69(s, 1H), 9.00(s, 1H), 8.91(s, 1H), 8.52(s, 1H), 8.11(d, J = 7.2 Hz, 1H), 6.86(d, J = 6.0 Hz, 1H), 4.05-4.02(m, 1H), 3.88-3.85(m, 1H), 2.36(m, 1H), 1.13(d, J = 6.9 Hz, 6H) |
| 69 | 380.20 | methanol-d$_4$: 9.66(s, 1H), 9.00(s, 1H), 8.53(s, 1H), 8.11(d, J = 6.9 Hz, 1H), 6.80(d, J = 7.2 Hz, 1H), 4.05-4.00(m, 1H), 3.89-3.86(m, 1H), 2.08-2.05(m, 1H), 2.01-1.96(m, 1H), 1.12(t, J = 7.4 Hz, 3H) |
| 70 | 370.10 | DMSO-d$_6$: 9.58(s, 1H), 8.97(s, 1H), 8.76(t, J = 6.2 Hz, 1H), 8.29(d, J = 3.5 Hz, 1H), 8.11(s, 1H), 7.47(d, J = 8.0 Hz, 1H), 7.10(d, J = 7.9 Hz, 1H), 4.37(s, H), 4.17(d, J = 5.9 Hz, 2H), 3.95-3.88(m, 2H) |
| 71 | 384.10 | DMSO-d$_6$: 9.70(s, 1H), 9.04(s, 1H), 8.60(t, J = 6.2 Hz, 1H), 8.43(s, 1H), 8.27(d, J = 4.0 Hz, 1H), 7.47(d, J = 8.0 Hz, 1H), 7.10(d, J = 8.3 Hz, 1H), 3.94-3.87(m, 2H), 3.80(dd, J = 6.8, 12.7 Hz, 2H), 2.63(t, J = 6.9 Hz, 2H) |
| 72 | 392.10 | DMSO-d$_6$: 13.19(s, 1H), 9.54(s, 1H), 8.98(s, 2H), 8.60(s, 1H), 8.37(d, J = 6.9 Hz, 1H), 7.47(d, J = 8.0 Hz, 2H, 0.5 TsOH), 7.11(d, J = 8.0 Hz, 2H, 0.5 TsOH), 6.81(d, J = 6.6 Hz, 1H), 4.98(t, J = 7.5 Hz, 1H), 3.99-3.67(3xm, 5H), 2.35(bm, 1H), 2.29(s, 3H, 0.5 TsOH), 2.09-2.03(bm, 3H) |
| 73 | 408.20 | DMSO-d$_6$: 13.24(s, 1H), 9.66(s, 1H), 9.00(s, 1H), 8.83(bs, 1H), 8.70(s, 1H), 8.41(d, J = 7.0 Hz, 1H), 6.8(t, 1H), 5.35(bs, 1H), 3.95-3.90(m, 2H), 3.15(bs, 3H), 2.44(m, 1H), 1.03(bs, 3H), 0.85(d, J = 6.7 Hz, 3H) |

TABLE 2-continued

| Compound No. | ESMS (M+H) | $^1$H NMR NMR peaks given as δ values |
|---|---|---|
| 74 | 426.20 | DMSO-d$_6$: 13.26(s, 1H), 9.67(s, 1H), 9.07(s, 1H), 8.81(t, J = 6.3 Hz, 1H), 8.56(s, 1H), 8.38(d, J = 6.8 Hz, 1H), 4.79(d, J = 10.1 Hz, 1H), 3.97-3.90(m, 2H), 3.24(d, J = 4.7 Hz, 3H), 2.44-2.40(m, 1H), 1.03(d, J = 6.5 Hz, 3H), 0.90(d, J = 6.7 Hz, 3H) |
| 75 | 426.50 | CD$_3$CN: 11.6(s, 1H), 9.79(s, 1H), 9.10(s, 1H), 8.49(s, 1H), 8.26(d, 1H), 7.37(m, 1H), 6.32(s, 1H), 4.6-4.9(m, 8H), 3.89(m, 1H), 3.69(m, 1H), 2.25(m, 1H), 1.63(s, 3H), 1.08(dd, 6H) |
| 76 | 352.09 | DMSO-d$_6$: 13.20(s, 1H), 9.60(s, 1H), 9.32(d, J = 10.6 Hz, 1H), 9.03(s, 1H), 8.97(s, 1H), 8.63(s, 1H), 8.22(d, J = 6.6 Hz, 1H), 6.79(d, J = 6.0 Hz, 1H), 4.38(s, 2H), 4.01-3.90(m, 2H) |
| 77 | 412.40 | CD$_3$CN: 11.53(s, 1H), 9.78(d, 1H), 9.09(s, 1H), 8.51(d, 1H), 8.27(d, 1H), 7.0-7.7(m, 9H), 6.58(s, 1H), 3.28(m, 2H), 2.21(m, 1H), 2.05(m, 1H), 1.64(s, 3H), 0.92(t, 3H) |
| 78 | 367.10 | DMSO-d$_6$: 12.8(m, 1H); 9.85(s, 0.5H); 9.62(s, 0.5H); 8.95(m, 1H); 8.80-8.60(m, 1H); 8.55(m, 1H); 8.42(m, 1H); 8.25-8.15(m, 1H); 4.54(m, 1H); 3.80(m, 2H); 1.32(m, 3H) |
| 79 | 367.10 | DMSO-d$_6$: 12.8(m, 1H); 9.85(s, 0.5H); 9.62(s, 0.5H); 8.95(m, 1H); 8.80-8.60(m, 1H); 8.55(m, 1H); 8.42(m, 1H); 8.25-8.15(m, 1H); 4.54(m, 1H); 3.80(m, 2H); 1.32(m, 3H) |
| 80 | 394.20 | DMSO-d$_6$: 13.2(bs, 1H), 9.57(s, 1H), 8.98(bs, 2H), 8.61(bs, 2H), 8.23(d, J = 6.8 Hz, 2H), 6.76(s, 1H), 3.78(bs, 2H), 2.13-2.07(m, 1H), 1.97-1.93(m, 1H), 1.59(s, 3H), 0.88(t, J = 7.5 Hz, 3H) |
| 81 | 412.20 | DMSO-d$_6$: 13.35(s, 1H), 9.66(s, 1H), 9.10(s, 1H), 8.52(t, J = 6.3 Hz, 1H), 8.32-8.31(m, 2H), 7.57-7.55(m, 1H), 3.85-3.70(m, 2H), 2.20-2.16(m, 1H), 1.97-1.92(m, 1H), 1.56(s, 3H), 0.83(t, J = 7.5 Hz, 3H) |
| 82 | 366.20 | |
| 83 | 335.30 | DMSO-d$_6$: 9.39(s, H), 8.95(s, H), 8.60(s, H), 8.22(s, H), 7.70(d, J = 8.2 Hz, H), 7.51(d, J = 7.0 Hz, 2H), 7.24-7.20(m, 2H), 6.71(s, H), 5.58(s, H), 3.48(q, H), 1.60(d, J = 6.9 Hz, 3H) |
| 84 | 335.30 | DMSO-d$_6$: 9.39(s, H), 8.95(s, H), 8.60(s, H), 8.22(s, H), 7.70(d, J = 8.2 Hz, H), 7.51(d, J = 7.0 Hz, 2H), 7.24-7.20(m, 2H), 6.71(s, H), 5.58(s, H), 3.48(q, H), 1.60(d, J = 6.9 Hz, 3H) |
| 85 | 331.30 | |
| 86 | 331.30 | |
| 87 | 408.40 | CD$_3$CN: 10.11(s, 1H), 9.70(s, 1H), 8.83(s, 1H), 8.23(d, 1H), 8.10(d, 1H), 7.19(m, 1H), 6.46(d, 1H), 5.90(s, 1H), 3.94(m, 1H), 3.55(m, 1H), 2.13(m, 1H), 1.59(s, 3H), 1.05(dd, 6H) |
| 88 | 394.40 | CD$_3$CN: 10.11(s, 1H), 9.69(s, 1H), 8.82(s, 1H), 8.21(d, 1H), 8.10(d, 1H), 7.20(m, 1H), 6.42(d, 1H), 6.02(s, 1H), 3.85(m, 1H), 3.77(m, 1H), 1.92(m, 2H), 1.58(s, 3H), 0.91(t, 3H) |
| 89 | 426.25 | methanol-d$_4$: 9.84(s, 1H), 9.11(s, 1H), 8.57(bt, 1H), 8.45(d, J = 3.0 Hz, 1H), 8.22(d, J = 3.7 Hz, 1H), 3.82(m, 2H), 2.32(m, 2H), 2.09(m, 2H), 0.86(t, J = 7.5 Hz, 6H) |
| 90 | 408.21 | |
| 91 | 381.20 | DMSO-d$_6$: 13.1(m, 1H); 9.90(s, 0.5H); 9.60(s, 0.5H); 8.95(d, 1H); 8.80(m, 0.5H); 8.68(m, 0.5H); 8.55(m, 1.5H); 8.45(s, 0.5H); 8.25(m, 0.5H); 8.20(m, 0.5H); 4.50(m, 1H); 3.90(m, 2H); 1.80(m, 2H); 0.95(m, 3H) |
| 92 | 407.20 | |
| 93 | 426.40 | DMSO-d$_6$: 12.35(br s, 1H); 9.65(s, 1H); 9.1(s, 1H); 8.85(m, 1H); 8.35(m, 2H); 4.85(dd, 1H); 4.45(m, 1H); 4.1-3.7(m, 4H); 2.3(m, 1H); 1.95(m, 1H) |
| 94 | 408.40 | DMSO-d$_6$: 13.2(br s, 1H); 9.65(m, 2H); 9.05(m, 2H); 8.6(m, 1H); 8.35(d, 1H); 6.85(m, 0.7H); 6.25(m, 0.3H); 5.0(m, 1H); 4.5(m, 1H); 4.15-3.6(m, 4H); 2.3(m, 1H); 2.0(m, 1H) |
| 95 | 396.11 | |
| 96 | 392.40 | CD$_3$CN: 10.22(s, 1H), 8.84(s, 1H), 8.32(d, 1H), 8.20(s, 1H), 7.34(s, 1H), 6.53(d, 1H), 3.88(m, 2H), 3.30(s, 3H), 1.86(m, 1H), 1.58(m, 1H), 1.45(m, 1H), 1.17(m, 1H) |
| 97 | 442.40 | |
| 98 | 406.40 | methanol-d$_4$: 9.58(s, 1H), 8.96(s, 1H), 8.57(d, J = 16.6 Hz, 1H), 8.21(d, J = 6.7 Hz, 1H), 6.70(s, 1H), 3.78-3.75(m, 2H), 2.37(m, 2H), 2.09(m, 2H), 1.74(m, 4H), |
| 99 | 410.30 | CD$_3$CN: 10.20(s, 1H), 9.69(s, 1H), 8.85(s, 1H), 8.24(s, 1H), 8.12(m, 1H), 7.55(m, 1H), 3.92(m, 2H), 3.27(s, 3H), 1.72(m, 1H), 1.54(m, 1H), 1.36(m, 1H), 1.30(m, 1H) |
| 100 | 460.40 | CD$_3$CN: 10.25(s, 1H), 9.62(s, 1H), 8.82(s, 1H), 8.25(s, 1H), 8.11(m, 1H), 7.45(m, 1H), 6.44(m, 2H), 4.02(s, 3H), 3.08(m, 1H) |

TABLE 2-continued

| Compound No. | ESMS (M+H) | $^1$H NMR<br>NMR peaks given as δ values |
|---|---|---|
| 101 | 408.14 | methanol-d$_4$: 9.73(s, 1H), 9.06(s, 1H), 8.57(s, 1H), 8.21(d, J = 6.7 Hz, 1H), 6.74(d, J = 6.6 Hz, 1H), 4.42(d, J = 9.0 Hz, 1H), 4.14(d, J = 9.5 Hz, 1H), 4.05-4.02(m, 2H), 3.85-3.82(m, 2H), 2.83-2.77(m, 1H), 2.46-2.40(m, 1H), |
| 102 | 424.30 | |
| 103 | 380.20 | DMSO-d$_6$: 13.15(bs, 1H); 9.60(m, 1H); 9.40(bs, 1H); 8.90(s, 1H); 8.60(s, 1H); 8.18(m, 1H); 6.70(m, 1H); 5.35(m, 1H); 4.20(m, 2H); 3.3(s, 2.5H); 2.9(s, 0.5H); 1.42(m, 3H) |
| 104 | 398.16 | DMSO-d$_6$: 13.2(m, 1H); 9.62(m, 1H); 9.05(s, 1H); 8.32(m, 1H); 8.30(m, 1H); 7.98(m, 1H); 5.15(m, 1H); 4.15(m, 2H); 3.30(s, 2.5H); 2.90(s, 0.5H); 1.39(m, 3H) |
| 105 | 430.10 | methanol-d$_4$: 9.87(s, 1H), 9.04(s, 1H), 8.76(s, 1H), 8.55(m, 2H), 8.02(m, 1H), 7.91(m, 1H), 7.75(m, 1H), 3.80(m, 2H), 1.86(s, 6H). |
| 106 | 362.10 | DMSO-d$_6$: 12.49(s, 1H), 9.59(s, 1H), 8.82(s, 1H), 8.24(d, J = 3.9 Hz, 1H), 8.05(d, J = 2.5 Hz, 1H), 7.97(t, J = 5.7 Hz, 1H), 7.47(s, 1H), 7.08(t, J = 51.1 Hz, 1H), 4.23(t, J = 5.4 Hz, 1H), 4.14(t, J = 5.4 Hz, 1H), 3.29(q, J = 5.5 Hz, 1H), 3.24(q, J = 5.5 Hz, 1H), 1.56(s, 6H) |
| 107 | 380.10 | DMSO-d$_6$: 12.46(s, 1H), 9.57(s, 1H), 8.81(s, 1H), 8.25(d, J = 3.9 Hz, 1H), 8.17(t, J = 5.9 Hz, 1H), 8.02(d, J = 2.5 Hz, 1H), 7.53(s, 1H), 7.07(t, J = 51.1 Hz, 0.4H), 5.84-5.60(m, 1H), 3.39-3.32(m, 2H), 1.56(s, 6H), 0.00(TMS) |
| 108 | 404.95 | methanol-d$_4$: 9.9(s, 1H), 9.15(two s, 2H), 8.75(s, 1H), 8.65(s, 1H), 8.45(NH t, 1H), 7.7(d, 2H, p-toluenesulfonic acid, 33% salt), 7.2(d, 2H, p-toluenesulfonic acid, 33% salt), 3.85(m, 2H), 2.35(s, 3H, p-toluenesulfonic acid, 33% salt), 2(s, 6H) |
| 109 | 376.02 | DMSO-d$_6$: 13.12(br, 1H), 9.85(s, 1H), 9.10-9.04(m, 3H), 8.52(s, 1H), 7.61(d, J = 3.6 Hz, 1H), 6.69(d, J = 3.5 Hz, 1H), 5.17(s, 2H), 4.04-3.96(m, 2H) |
| 110 | 418.30 | methanol-d$_4$: 10.14(d, J = 1.0 Hz, 1H), 9.12(d, J = 1.0 Hz, 1H), 9.07(s, 1H), 8.67(s, 1H), 7.81(d, J = 3.7 Hz, 1H), 6.76(d, J = 3.7 Hz, 1H), 5.27(d, J = 10.3 Hz, 1H), 4.05(m, 1H), 3.90(m, 1H), 2.75(m, 1H), 1.22(d, J = 6.6 Hz, 3H), 0.84(d, J = 6.7 Hz, 3H) |
| 111 | 390.30 | |
| 112 | 404.30 | |
| 113 | 405.50 | |

Although certain exemplary embodiments are depicted and described above and herein, it will be appreciated that compounds of the invention can be prepared according to the methods described generally above using appropriate starting materials by methods generally available to one of ordinary skill in the art.

Example 38

JAK3 Inhibition Assay

Compounds were screened for their ability to inhibit JAK3 using the assay shown below. Reactions were carried out in a kinase buffer containing 100 mM HEPES (pH 7.4), 1 mM DTT, 10 mM MgCl$_2$, 25 mM NaCl, and 0.01% BSA. Substrate concentrations in the assay were 5 μM ATP (200 uCi/μmole ATP) and 1 μM poly(Glu)$_4$Tyr. Reactions were carried out 25° C. and 1 nM JAK3.

To each well of a 96 well polycarbonate plate was added 1.5 μl of a candidate JAK3 inhibitor along with 50 μl of kinase buffer containing 2 μM poly(Glu)$_4$Tyr and 10 μM ATP. This was then mixed and 50 μl of kinase buffer containing 2 nM JAK3 enzyme was added to start the reaction. After 20 minutes at room temperature (25° C.), the reaction was stopped with 50 μl of 20% trichloroacetic acid (TCA) that also contained 0.4 mM ATP. The entire contents of each well were then transferred to a 96 well glass fiber filter plate using a TomTek Cell Harvester. After washing, 60 μl of scintillation fluid was added and $^{33}$P incorporation detected on a Perkin Elmer TopCount.

Example 39

JAK2 Inhibition Assay

The assays were as described above in Example 36 except that JAK-2 enzyme was used, the final poly(Glu)$_4$Tyr concentration was 15 μM, and final ATP concentration was 12 μM.

Table 3 depicts enzyme inhibition data ($K_i$) for certain exemplary compounds. Compound numbers in Table 3 corresponds to those compounds depicted in Table 1. In Table 3, "A" represents a $K_i$ of less than 0.5 μM, "B" represents a $K_i$ of between 0.5 and 5.0 μM, and "C" represents a $K_i$ greater than 5.0 μM for the indicated enzyme.

TABLE 3

| Cmpd No. | JAK2 | JAK3 |
|---|---|---|
| 1 | A | A |
| 2 | C | B |
| 3 | C | A |
| 4 | A | A |
| 5 | A | A |
| 6 | A | A |

TABLE 3-continued

| Cmpd No. | JAK2 | JAK3 |
|---|---|---|
| 7 | B | A |
| 8 | B | A |
| 9 | B | A |
| 10 | C | B |
| 11 | C | B |
| 12 | B | A |
| 13 | B | B |
| 14 | B | A |
| 15 | B | B |
| 16 | B | B |
| 17 | B | B |
| 18 | B | A |
| 19 | B | A |
| 20 | B | A |
| 21 | B | B |
| 22 | B | B |
| 23 | B | B |
| 24 | B | B |
| 25 | B | B |
| 26 | C | B |
| 27 | A | A |
| 28 | B | B |
| 29 | B | B |
| 30 | A | A |
| 31 | C | B |
| 32 | C | C |
| 33 | C | C |
| 34 | B | A |
| 35 | C | B |
| 36 | C | C |
| 37 | C | C |
| 38 | A | A |
| 39 | A | A |
| 40 | A | A |
| 41 | B | A |
| 42 | B | A |
| 43 | B | B |
| 44 | B | B |
| 45 | A | A |
| 46 | B | A |
| 47 | C | B |
| 48 | C | B |
| 49 | C | B |
| 50 | B | A |
| 51 | C | C |
| 52 | B | B |
| 53 | C | B |
| 54 | A | A |
| 55 | B | B |
| 56 | A | A |
| 57 | A | A |
| 58 | A | A |
| 59 | A | A |
| 60 | B | A |
| 61 | B | A |
| 62 | A | A |
| 63 | A | A |
| 64 | A | A |
| 65 | A | A |
| 66 | A | A |
| 67 | B | B |
| 68 | A | A |
| 69 | A | A |
| 70 | B | A |
| 71 | A | A |
| 72 | A | A |
| 73 | A | A |
| 74 | A | A |
| 75 | B | A |
| 76 | A | A |
| 77 | B | A |
| 78 | B | A |
| 79 | B | A |
| 80 | A | A |
| 81 | A | A |
| 82 | A | A |
| 83 | A | A |
| 84 | A | A |
| 85 | A | A |
| 86 | B | A |
| 87 | A | A |
| 88 | A | A |
| 89 | A | A |
| 90 | A | A |
| 91 | A | A |
| 92 | A | A |
| 93 | B | A |
| 94 | A | A |
| 95 | C | C |
| 96 | A | A |
| 97 | B | A |
| 98 | A | A |
| 99 | B | A |
| 100 | B | A |
| 101 | A | A |
| 102 | A | A |
| 103 | B | A |
| 104 | B | A |
| 105 | A | A |
| 106 | A | A |
| 107 | A | A |
| 108 | A | A |
| 109 | A | A |
| 110 | A | A |
| 111 | A | A |
| 112 | A | A |
| 113 | A | A |

What is claimed is:

1. A compound having the formula:

(I)

or a pharmaceutically acceptable salt thereof
wherein
$R^1$ is —H;
$R^2$ is —H;
Q is a 6 membered heteroaryl ring selected from pyridyl, pyrimidyl, pyrazinyl, triazinyl or pyridazinyl optionally substituted with 1-3 $J^Q$ groups; or the compound has the formula:

(II-b)

wherein each of $Z^1$, $Z^2$, and $Z^4$ is, independently, CH or N, wherein at least one of $Z^1$ or $Z^2$ is N $J^Q$ is halogen, $OCF_3$, —$(V)_m$—R'', —$(V)_m$—CN, —$(V)_m$—$NO_2$ or —$(V)_m$—($C_{1-4}$ haloaliphatic), or two $J^Q$ groups, taken together with the atoms to which they are attached, form a 3-8 membered saturated, partially saturated, or unsaturated ring with 0-3 heteroatoms selected from O, N, or S, wherein said ring is optionally substituted with 0-4 occurrences of $J^U$;

V is a $C_{1-10}$ aliphatic, wherein up to three methylene units are replaced by $G^V$, wherein $G^V$ is selected from —NH—, —NR—, —O—, —S—, —C(O)O—, —OC(O)—, —C(O)C(O)—, —C(O)—, —C(O)NH—, —C(O)NR—, —C(=N—CN), —NHC(O)—, —NRC(O)—, —NHC(O)O—, —NRC(O)O—, —S(O)$_2$NH—, —S(O)$_2$NR—, —NHS(O)$_2$—, —NRS(O)$_2$—, —NHC(O)NH—, —NRC(O)NH—, —NHC(O)NR—, —NRC(O)NR, —OC(O)NH—, —OC(O)NR—, —NHS(O)$_2$NH—, —NRS(O)$_2$NH—, —NHS(O)$_2$NR—, —NRS(O)$_2$NR—, —S(O)—, or —S(O)$_2$—; and wherein V is optionally substituted with 1-6 occurrences of $J^V$;

R'' is H or an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R'' groups, or an R'' group and an R group, on the same substituent or different substituents, together with the atom(s) to which they are attached, form an optionally substituted 3-8 membered heterocyclyl; wherein each optionally substituted R'' group is independently and optionally substituted with 1-6 occurrences of $J^R$;

R is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of $J^X$;

each $J^V$, $J^U$, $J^X$, and $J^R$ are each independently selected from halogen, L, -(L)$_n$-R', -(L)$_n$-N(R')$_2$, -(L)$_n$-SR', -(L)$_n$-OR', -(L)$_n$-($C_{3-10}$ cycloaliphatic), -(L)$_n$-($C_{6-10}$ aryl), -(L)$_n$-(5-10 membered heteroaryl), -(L)$_n$-(5-10 membered heterocyclyl), oxo, $C_{1-4}$-haloalkoxy, $C_{1-4}$-haloalkyl, -(L)$_n$-$NO_2$, -(L)$_n$-CN, -(L)$_n$OH, -(L)$_n$-$CF_3$, —C(O)OR', —C(O)OH, —C(O)R', —C(O)H, —OC(O)R', or —NHC(O)R'; or any two $J^V$, $J^U$, $J^X$, or $J^R$ groups, on the same substituent or different substituents, together with the atom(s) to which each $J^V$, $J^U$, $J^X$, and $J^R$ group is bound, form a 5-7 membered saturated, unsaturated, or partially saturated ring;

R' is H or $C_{1-6}$ aliphatic; or two R' groups, or an R' group and an R group, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —$NO_2$, —$CF_3$, —CN, —C(O)OR*, —C(O)R*, OC(O)R*, or NHC(O)R*, wherein R* is H or an unsubstituted $C_{1-6}$ aliphatic;

L is a $C_{1-6}$ aliphatic wherein up to three methylene units are replaced by —NH—, —NR$^6$—, —O—, —S—, —C(O)O—, —OC(O)—, —C(O)C(O)—, —C(O)—, —C(O)NH—, —C(O)NR$^6$—, —C(=N—CN), —NHC(O)—, —NR$^6$C(O)—, —NHC(O)O—, —NR$^6$C(O)O—, —S(O)$_2$NH—, —S(O)$_2$NR$^6$—, —NHS(O)$_2$—, —NR$^6$S(O)$_2$—, —NHC(O)NH—, —NR$^6$C(O)NH—, —NHC(O)NR$^6$—, —NR$^6$C(O)NR$^6$, —OC(O)NH—, —OC(O)NR$^6$—, —NHS(O)$_2$NH—, —NR$^6$S(O)$_2$NH—, —NHS(O)$_2$NR$^6$—, —NR$^6$S(O)$_2$NR$^6$—, —S(O)—, or —S(O)$_2$—;

$R^6$ is selected from $C_{1-6}$ aliphatic, $C_{3-10}$ cycloaliphatic, $C_{6-10}$ aryl, 5-10 membered heteroaryl, or 5-10 membered heterocyclyl; or two $R^6$ groups, on the same substituent or different substituents, together with the atom(s) to which each $R^6$ group is bound, form a 3-8 membered heterocyclyl;

each of m and n is, independently, 0 or 1.

2. The compound according to claim 1, wherein $J^Q$ is

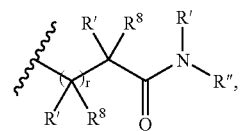

wherein each $R^8$ is H, $C_{1-6}$ alkyl, $CF_3$, $CH_2CF_3$, $CH_2CN$, or $CH_2OR'$ independently, optionally substituted with up to two occurrences of $J^V$; and r is 0 or 1.

3. The compound according to claim 2, wherein $J^Q$ is

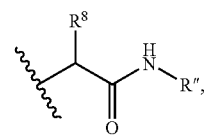

wherein $R^8$ is optionally substituted with up to two occurrences of $J^V$.

4. The compound according to claim 3, wherein $R^8$ is selected from

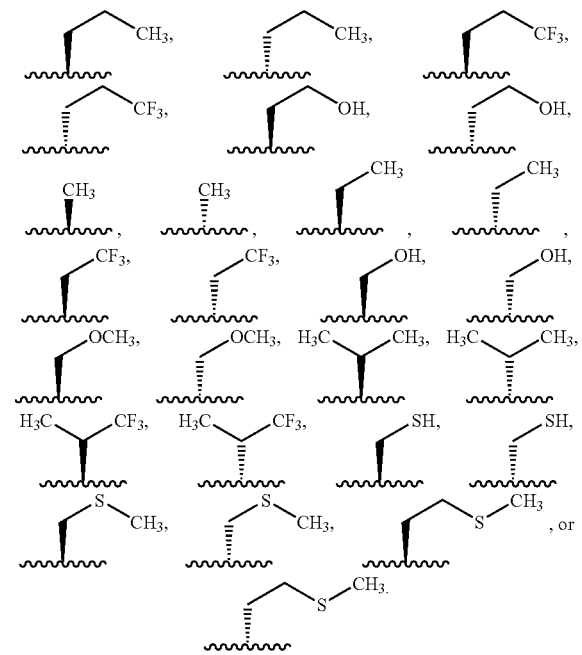

5. The compound according to claim 2, wherein r is 0 and R', $R^8$, and the intervening carbon together are 6. The compound according to claim 2, wherein each of $Z^1$ and $Z^2$ is N.

7. The compound according to claim 2, wherein R" is $CF_3$, $CH_2CF_3$ or $CH_2CH_2CF_3$.

8. The compound according to claim 1 having the formula:

(III)

wherein
$Z^2$ is CH or N;
$Z^3$ is C-$J^{Q3}$ or N;
$J^{Q1}$ is —N(R')R", —$CH_2$N(R')R", —NR'C(O)R", —NR'C(O)$R^9$R", —NR'C(O)OR", —NR'C(O)O$R^9$R", —NR'C(R')($R^8$)R", —NR'C(R')($R^8$)C(O)OR", —N(R')$R^9$R", —N(R')$R^9$N(R')R", —N(R')$R^9$OR", —NR'C(R')($R^8$)R", —NR'$CH_2$C(O)N(R')R", or —NR'CR'($R^8$)C(O)N(R')R";
$J^{Q2}$ is hydrogen, —C(O)OH, —C(O)OR", —C(O)O$R^9$R", —C(O)R", —C(O)$R^9$R", —C(O)NHR", —C(O)N(R)R", —C(O)NHR$^9$OR", —C(O)NHR$^9$R", —C(O)N(R)R$^9$R", —OH, —OR", —CN, or —R";
wherein
 a) $R^8$ is H, $C_{1-6}$ alkyl, $CF_3$, $CH_2CF_3$, $CH_2CN$, or $CH_2$OR'; and
 b) $R^9$ is $C_{1-6}$ aliphatic, wherein $R^9$ is optionally substituted with 0-4 occurrences of $J^V$; and
$J^{Q3}$ is hydrogen, halo, or $NO_2$.

9. The compound according to claim 8, wherein $Z^2$ is CH.

10. The compound according to claim 8, wherein $Z^2$ is N.

11. The compound according to claim 8, wherein $Z^3$ is C-$J^{Q3}$.

12. The compound according to claim 11, wherein $J^{Q3}$ is F.

13. The compound according to claim 11, wherein $J^{Q3}$ is H.

14. The compound according to claim 8, wherein $Z^3$ is N.

15. The compound according to claim 14, wherein $Z^2$ is N.

16. The compound according to claim 8, wherein $J^{Q2}$ is hydrogen.

17. The compound according to claim 8, wherein $J^{Q2}$ is —C(O)OH, —C(O)OR", —C(O)R", —C(O)NHR", —C(O)N(R)R", —C(O)N(R)R$^9$R", —CN, or —R", wherein $J^{Q2}$ is optionally substituted with up to two occurrences of $J^V$.

18. The compound according to claim 8, wherein $J^{Q1}$ is wherein
$R^8$ is optionally substituted with up to two occurrences of $J^V$.

19. The compound according to claim 18, wherein $J^{Q1}$ is wherein
$R^8$ is optionally substituted with up to two occurrences of $J^V$.

20. The compound according to claim 19, wherein $R^8$ is selected from

21. The compound according to claim 18, wherein $J^{Q1}$ is wherein
ring A is optionally substituted with up to four occurrences of $J^V$.

22. The compound according to claim 18, wherein $J^{Q1}$ is
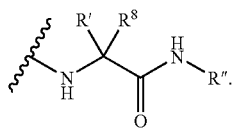
23. The compound according to claim 22, wherein R', $R^8$, and the intervening carbon together are
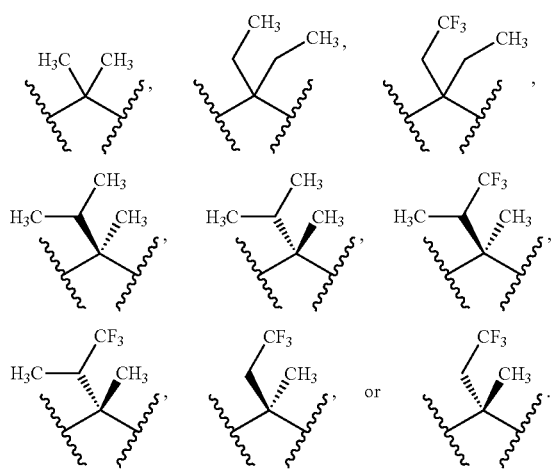
24. The compound according to claim 18, wherein R" is $CF_3$, $CH_2CF_3$, or $CH_2CH_2CF_3$.
25. The compound according to claim 1, wherein said compound is selected from:
1
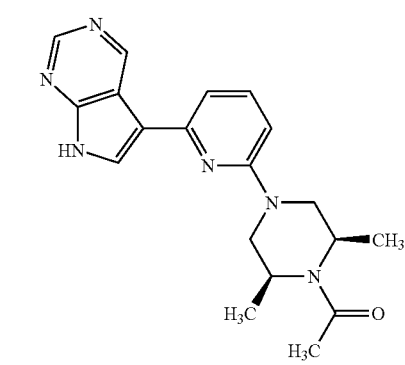
2
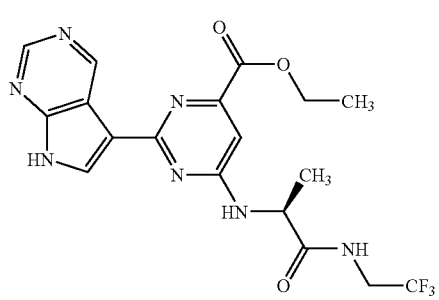
3
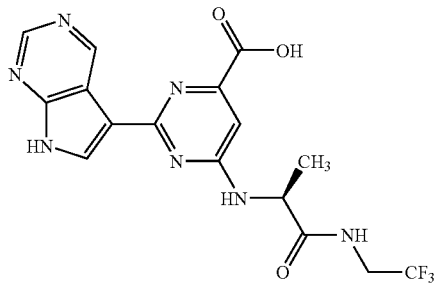
4
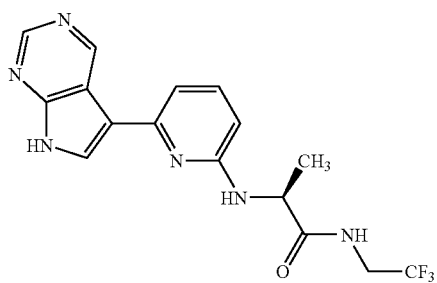
5
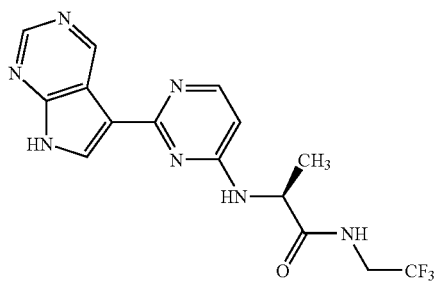
6
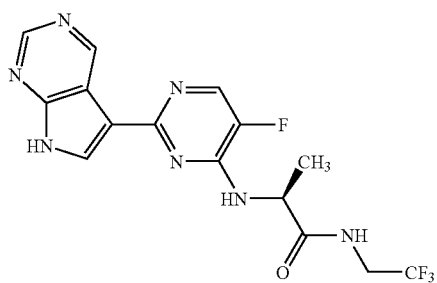
7
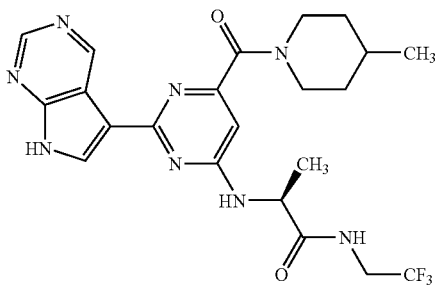

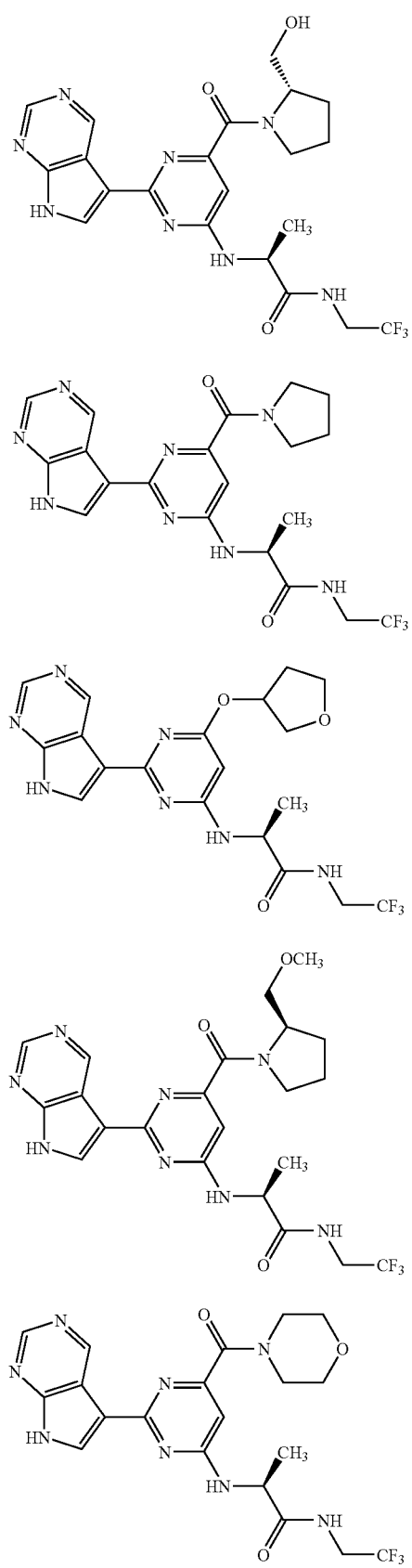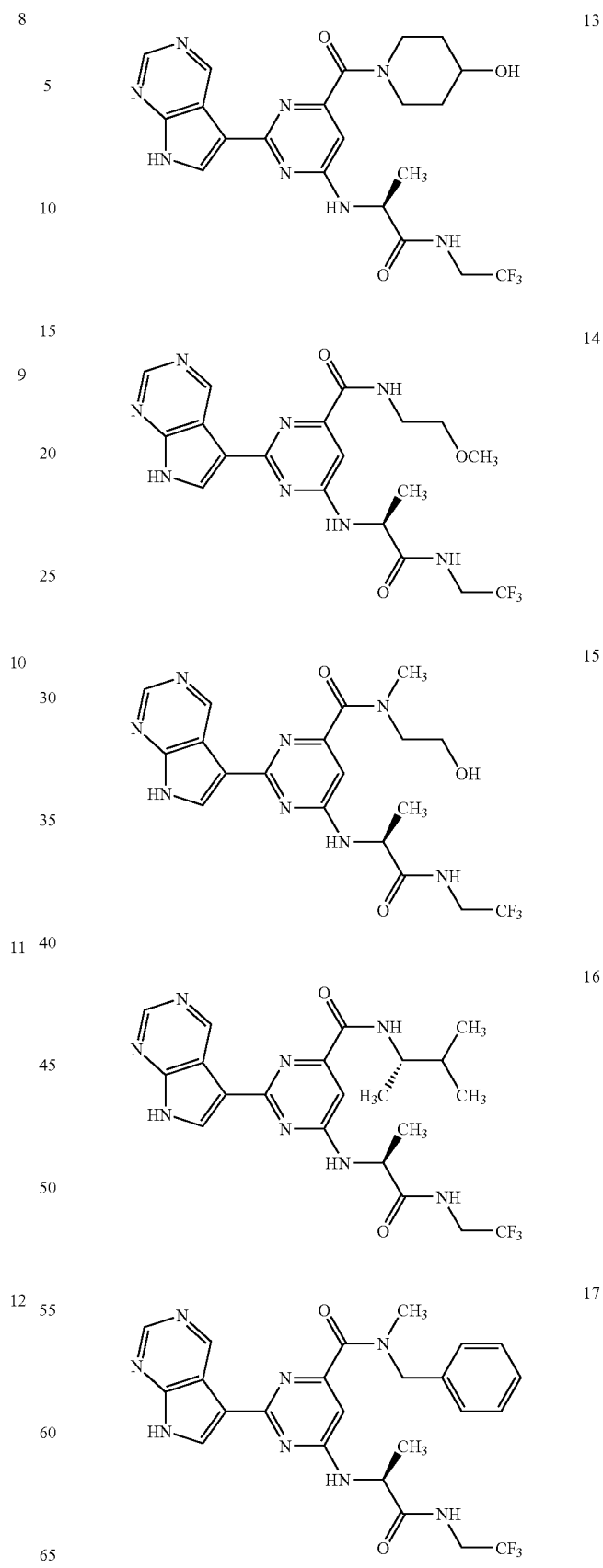

-continued
18
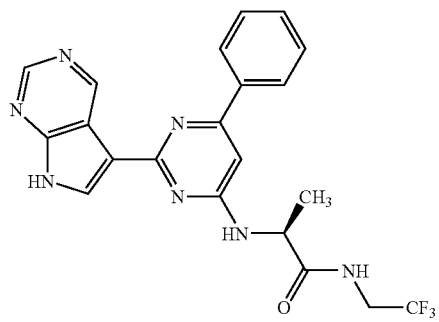
19
20
21
22
-continued
23
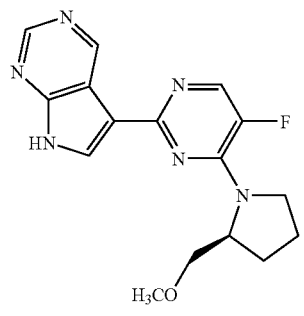
24
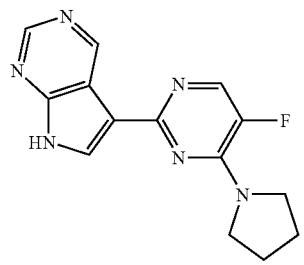
25
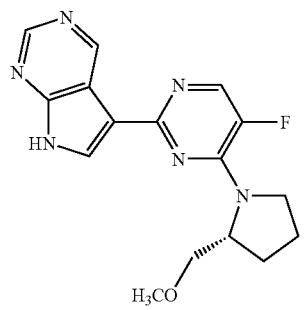
26
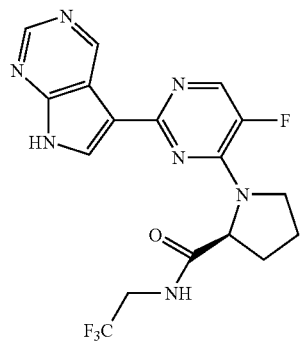
27
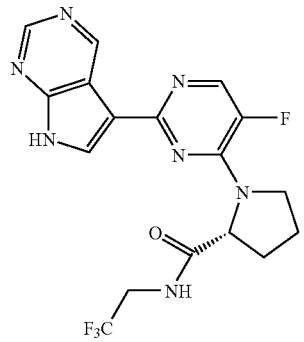

-continued
28
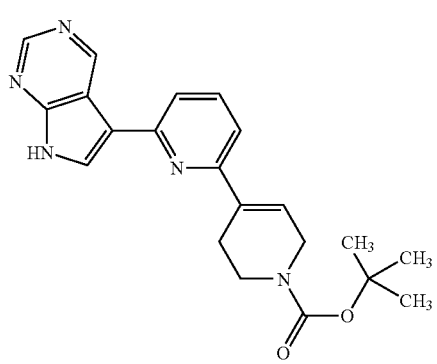
29
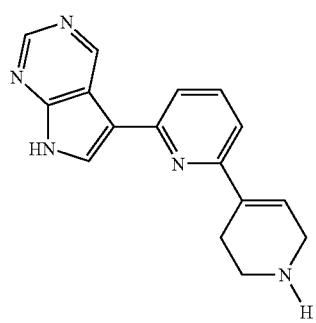
30
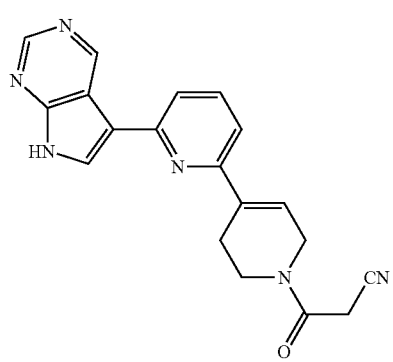
31
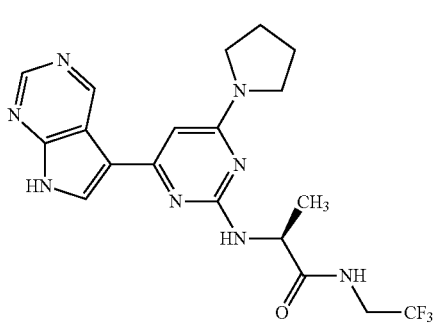
32
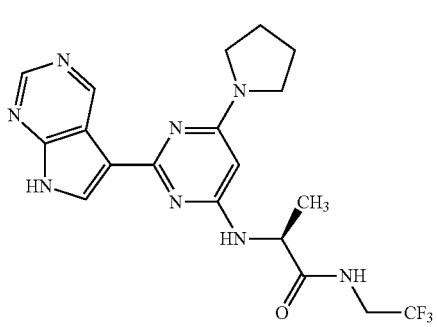
-continued
33
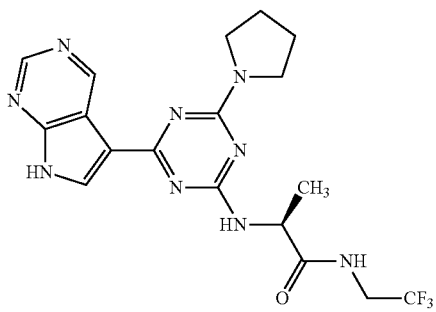
35
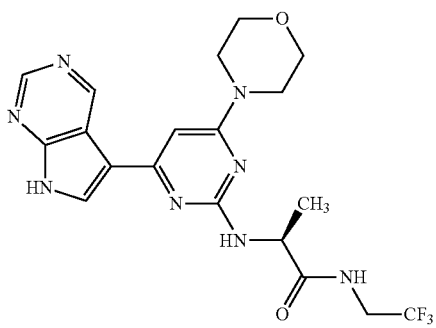
36
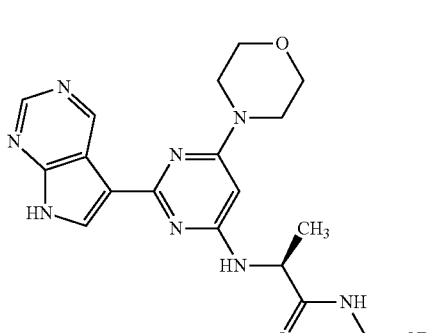
37
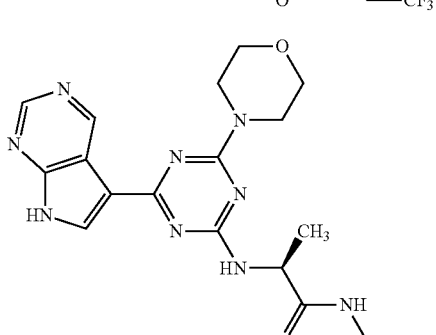
39
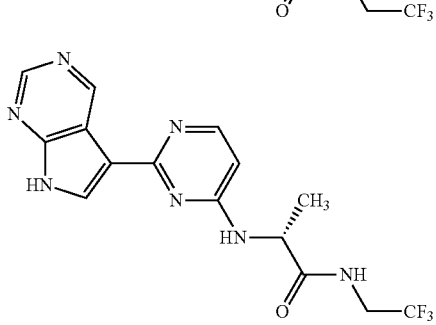

-continued
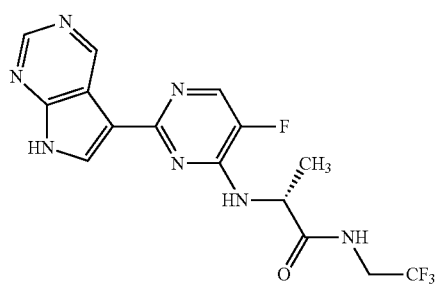
40
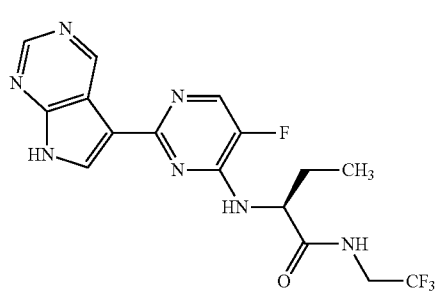
41
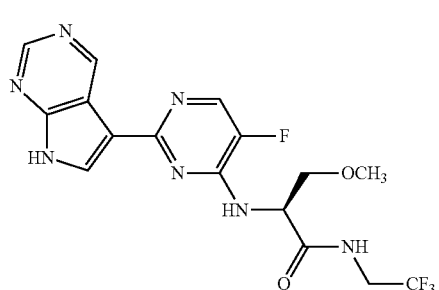
42
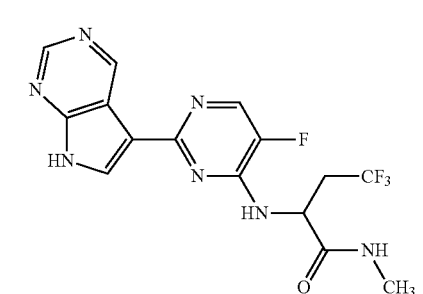
43
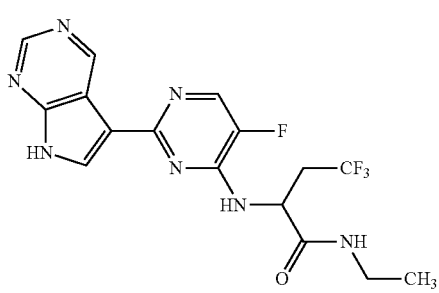
44
-continued
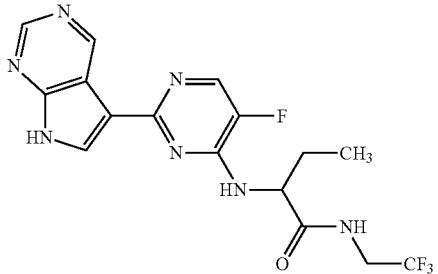
45
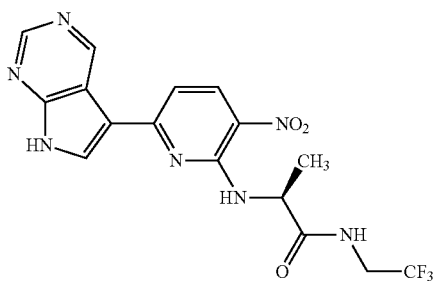
46
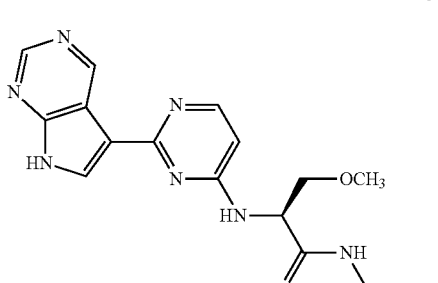
48
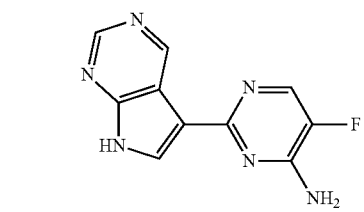
49
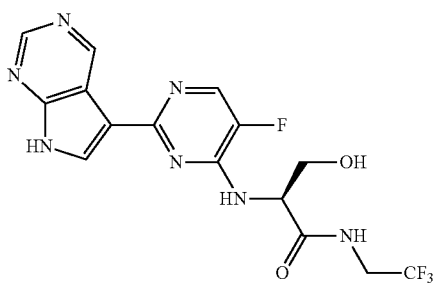
50
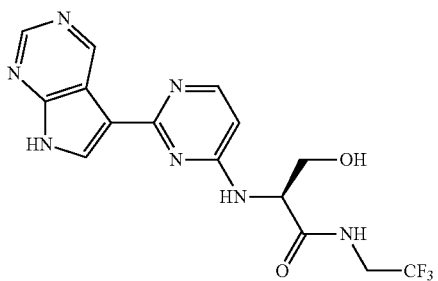
51

93
-continued
52
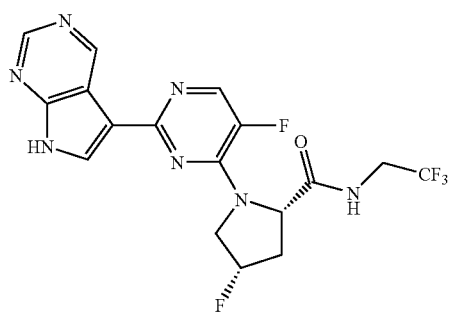
53
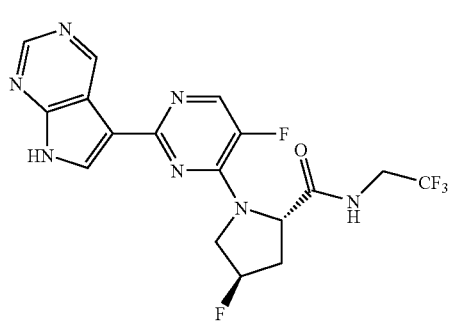
54
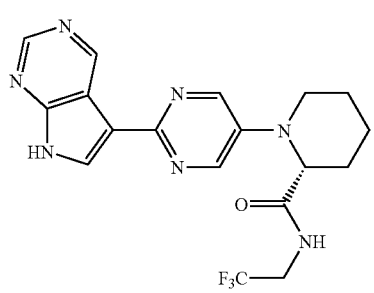
55
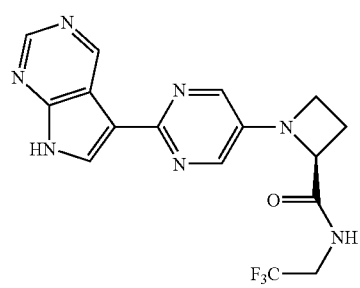
56
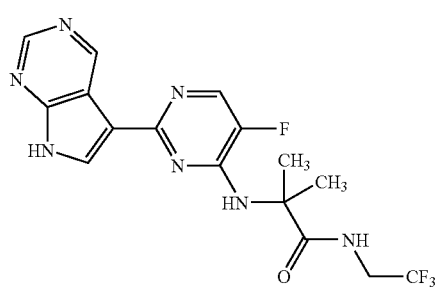
94
-continued
58
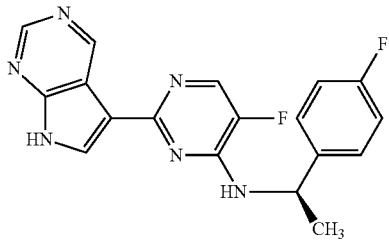
59
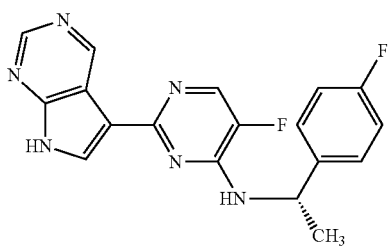
60
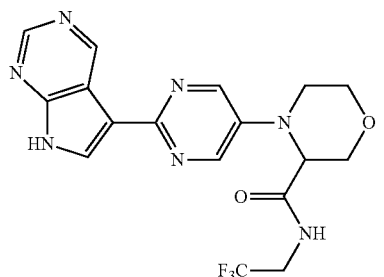
61
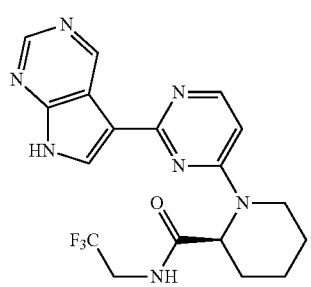
62
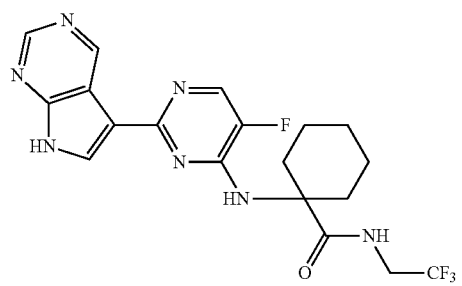
63
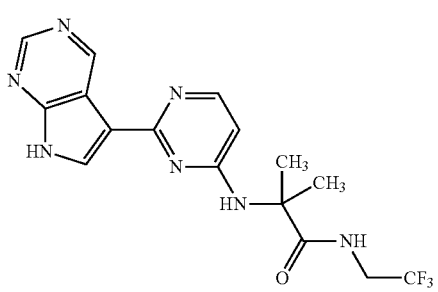

65
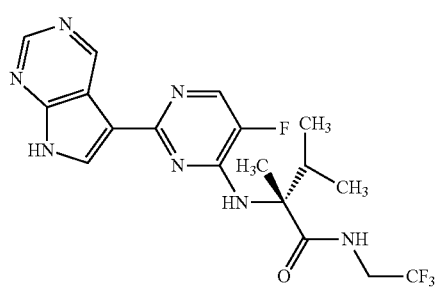
66
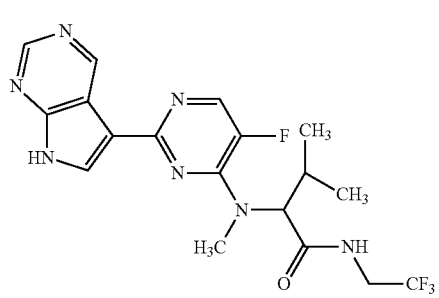
67
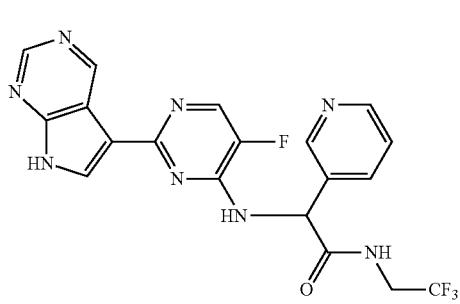
68
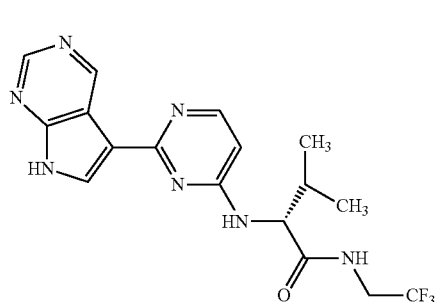
69
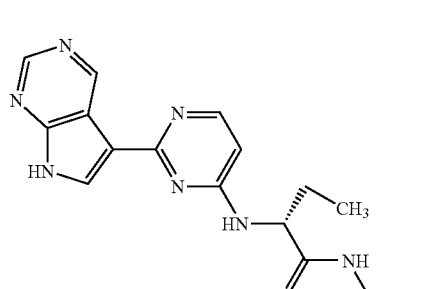
70
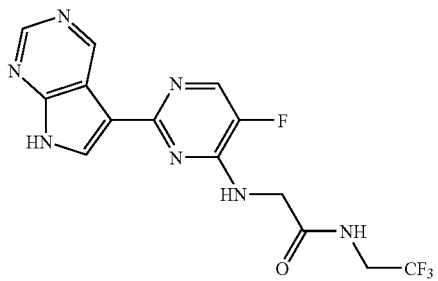
71
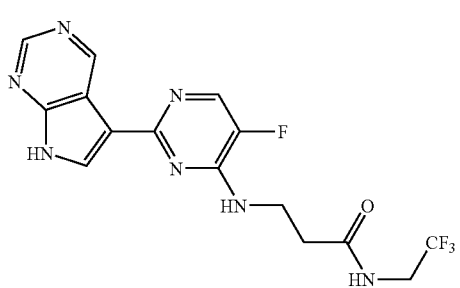
72
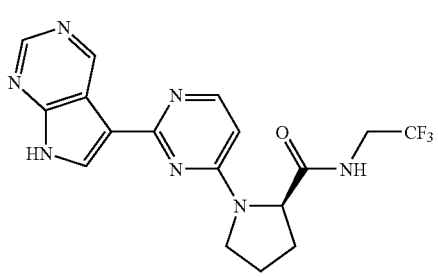
73
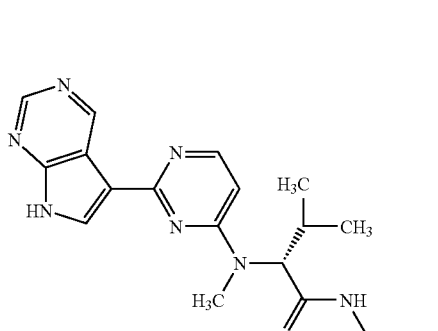
74
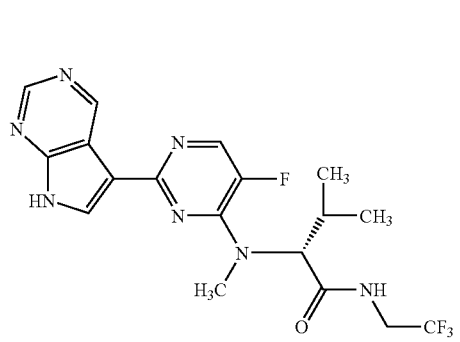

75
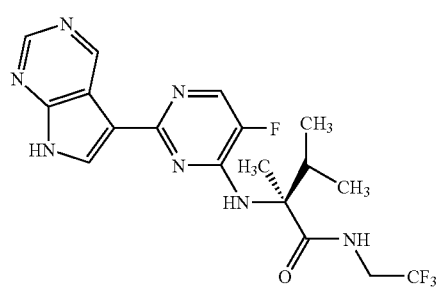
76
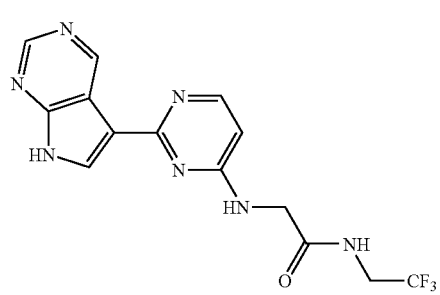
77
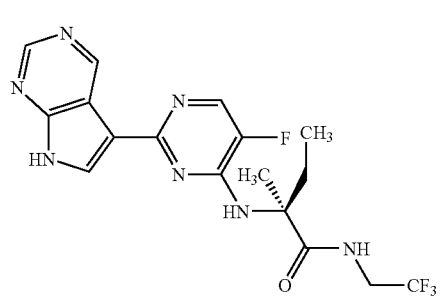
78
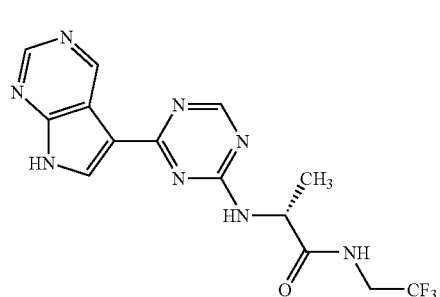
79
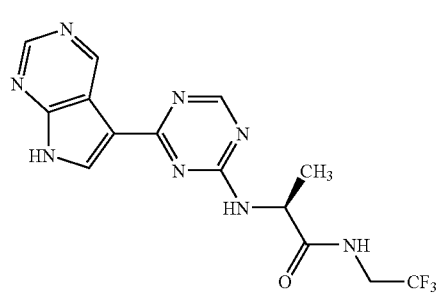
80
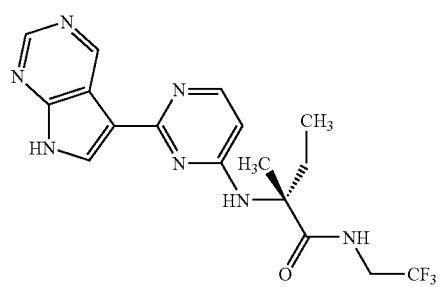
81
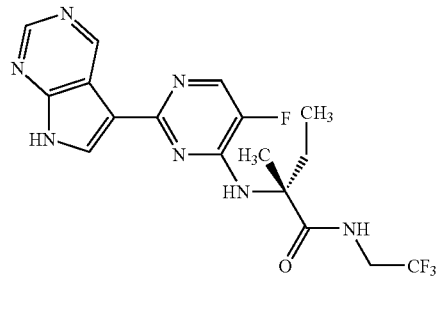
82
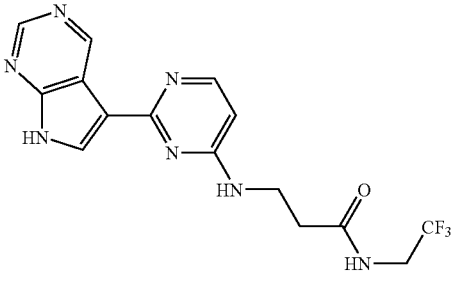
83
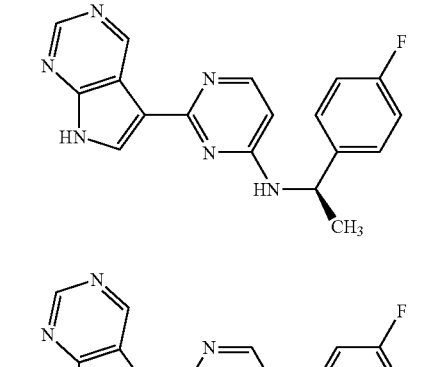
84
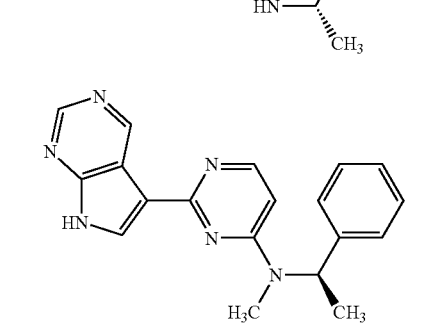
85
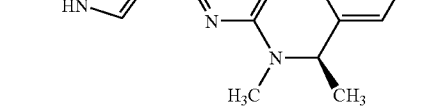

86
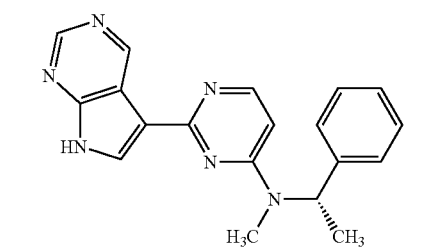
87
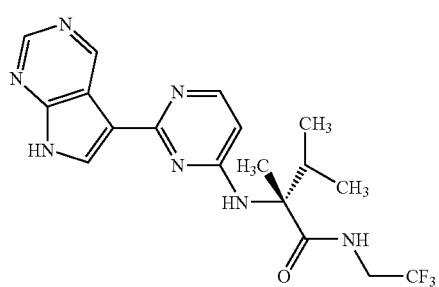
88
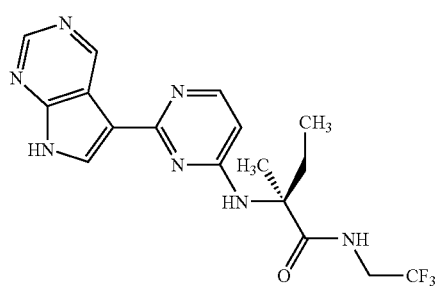
89
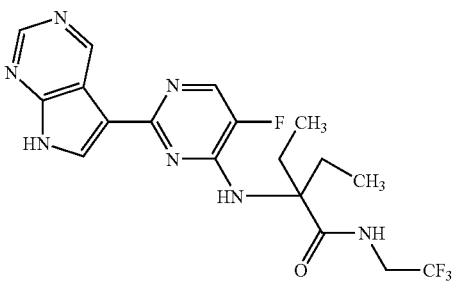
90
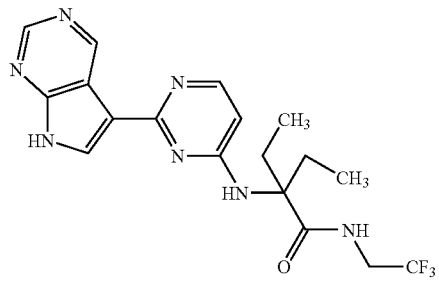
91
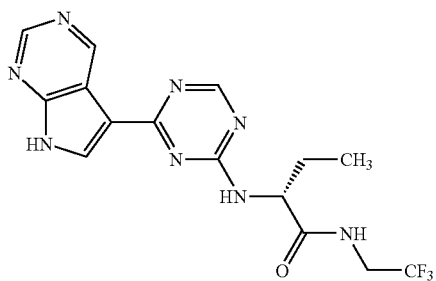
92
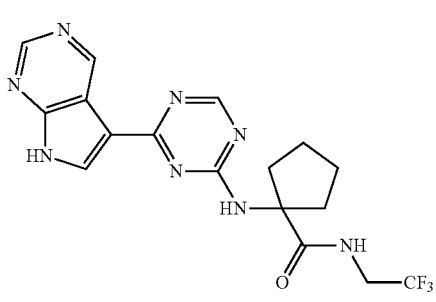
93
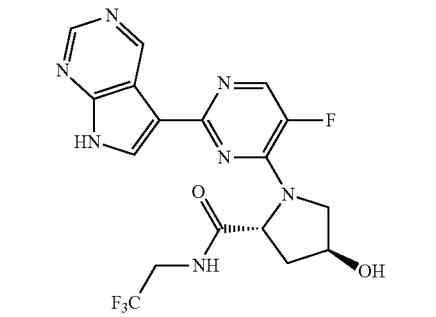
94
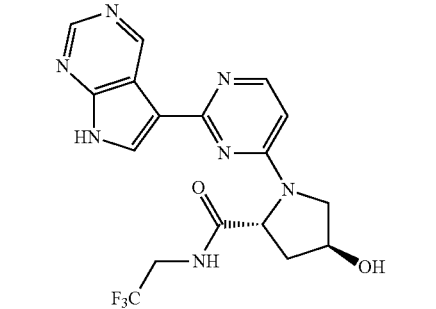
95
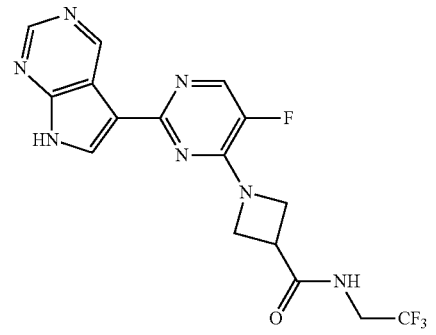

97
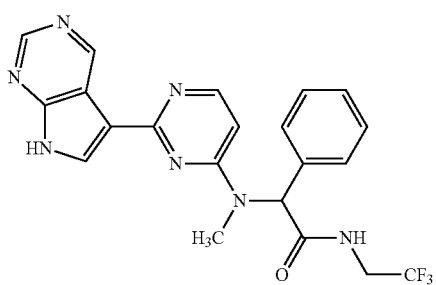
98
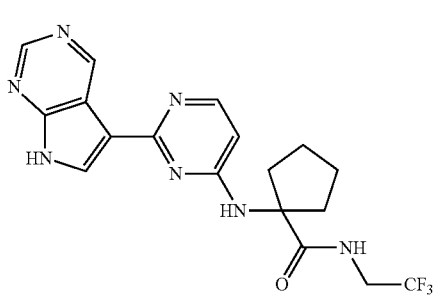
100
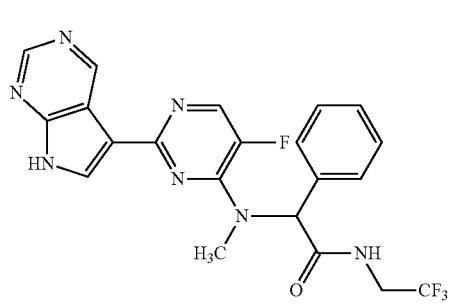
101
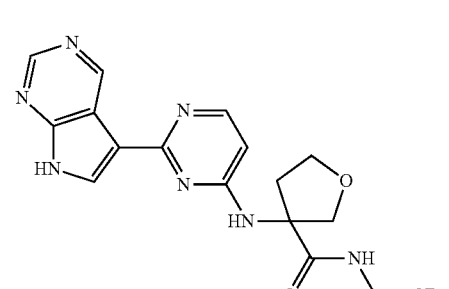
102
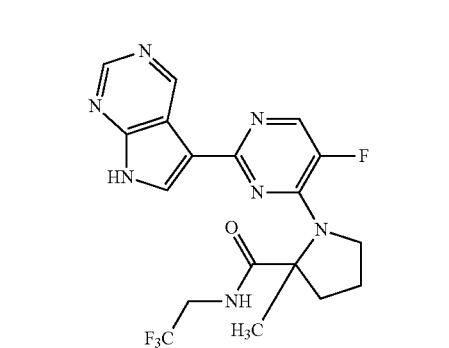
103
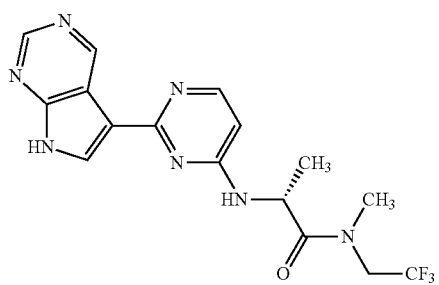
104
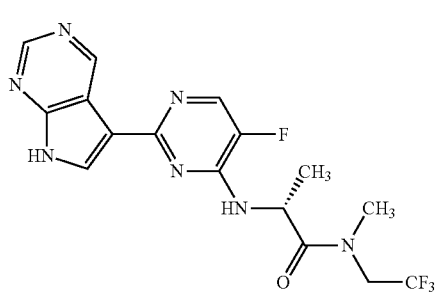
106
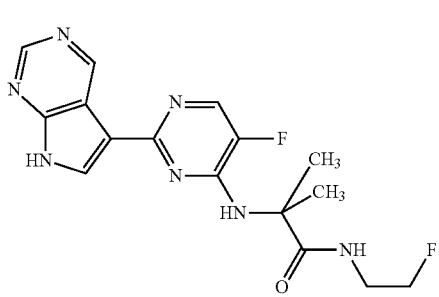
107
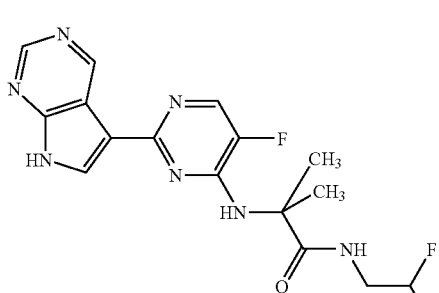
108
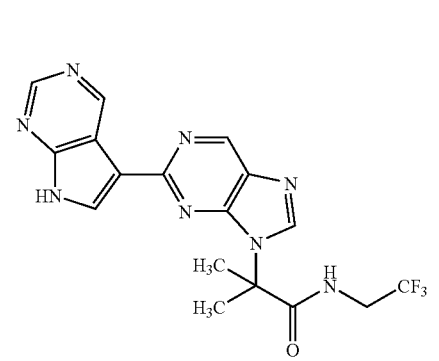

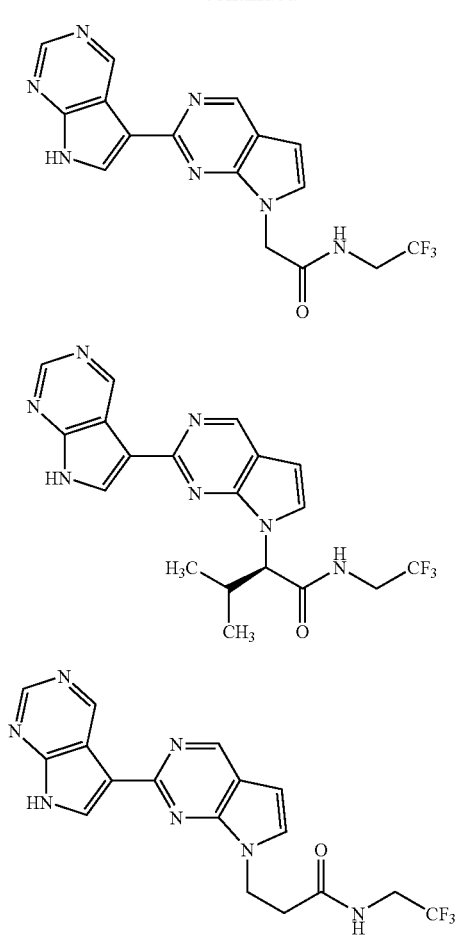
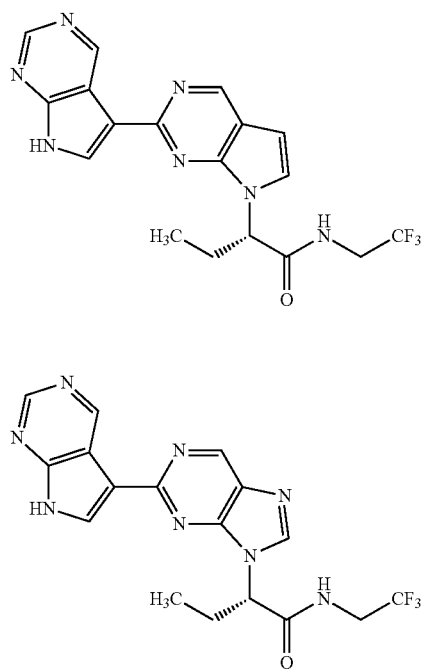
26. A pharmaceutical composition comprising a compound according to claim 1 and a pharmaceutically acceptable carrier, adjuvant, or vehicle.
* * * * *